(12) United States Patent
Mitsky et al.

(10) Patent No.: US 6,448,473 B1
(45) Date of Patent: Sep. 10, 2002

(54) MULTIGENE EXPRESSION VECTORS FOR THE BIOSYNTHESIS OF PRODUCTS VIA MULTIENZYME BIOLOGICAL PATHWAYS

(75) Inventors: Timothy A. Mitsky, Maryland Heights, MO (US); Steven C. Slater, Acton, MA (US); Steven E. Reiser; Ming Hao, both of St. Louis, MO (US); Kathryn L. Houmiel, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/517,978

(22) Filed: Mar. 3, 2000

Related U.S. Application Data

(60) Provisional application No. 60/123,015, filed on Mar. 5, 1999.

(51) Int. Cl.[7] .............................. A01H 1/00; A01H 5/00; C12N 15/82; C12N 15/87; C12Q 1/68
(52) U.S. Cl. ...................... 800/278; 800/287; 800/298; 435/6; 435/183; 435/320.1; 435/419
(58) Field of Search .................... 435/6, 320.1, 419, 435/183, 103; 800/287, 298, 278

(56) References Cited

U.S. PATENT DOCUMENTS

| | | | | |
|---|---|---|---|---|
| 5,569,595 A | * | 10/1996 | Dennis et al. | 435/135 |
| 5,891,686 A | * | 4/1999 | Dennis et al. | 435/135 |
| 5,942,660 A | * | 8/1999 | Gruys et al. | 800/298 |
| 5,965,793 A | * | 10/1999 | Broun et al. | 800/287 |

FOREIGN PATENT DOCUMENTS

| | | |
|---|---|---|
| EP | 0870837 A1 | 10/1998 |
| WO | WO 92/19747 | 11/1992 |
| WO | WO 93/06225 | 4/1993 |
| WO | WO 95/05472 | 2/1995 |
| WO | WO 98/00557 | 1/1998 |
| WO | WO 98/33931 | 8/1998 |
| WO | WO 98/36078 | 8/1998 |
| WO | WO 98/39453 | 9/1998 |

OTHER PUBLICATIONS

Byrom, D. *Trends Biotechnol.* 5: 246–250, 1987.
Poirier, Y., Nawrath, C. & Somerville, C. *Bio/Technology* 13: 143–150, 1995.
Poirier, Y. et al., *Science* 256: 520–523, 1992.
Nawrath, C., et al., *Proc. Natl. Acad. Sci. U.S.A.* 91: 12760–12764, 1994.
Nawrath, C., et al. *Molecular Breeding* 1: 105–22, 1995.
Williams, M. D., et al., *Appl. Environ. Microbiol.* 62: 2540–2546, 1996.
Leaf, T. A., et al. *Microbiol.* 142:1169–1180, 1996.
Huijberts, G. N. M., et al. *Appl. Environ. Microbiol.* 58: 536–544, 1992.
Huijberts, G. N. M., et al., *J. Bacteriol.* 176: 1661–1666, 1994.
Chen et al., *Nature Biotech.*, 16: 1060–1064, 1998.
Broun, et al. *Plant Physiol.* 113: 933–942, 1997.
Poirier, et al., *Fems Microbiology Rev.*, 103:237–246, 1992.
Slater et al., Nature Biotechnol., 17, 1999, "Metabolic Engineering of Arabidopsis and Brassica for Poly(3–hydroxybutyrate–co–3–hydroxyvalerate) Copolymer Production."

(List continued on next page.)

*Primary Examiner*—Kenneth R. Horlick
*Assistant Examiner*—Teresa Strzelecka
(74) *Attorney, Agent, or Firm*—Gary M. Bond; Howrey Simon Arnold & White, LLP

(57) ABSTRACT

The use of multigene vectors for the preparation of transformed host cells and plants is disclosed. Multigene vectors reduce the number of transformations required, and leads to increased production of polyhydroxyalkanoate polymer in the resulting transformed host cells and plants.

39 Claims, 38 Drawing Sheets

OTHER PUBLICATIONS

Schubert et al., J. Bacteriol., 5837–5847, Dec. 1998, "Cloning of the Alcaligenes entrophus Genes for Synthesis of Poly–B–Hydorxybutyric Acid (PHB) and Synthesis of PHB in *Escherichia coli*."

Broun et al., Plant Physiol., 133:933–942, 1997, "Accumulation of Ricionoleic, Lesquerolic, and Densipolic Acids in Seeds of Transgenic Arabidopsis Plants That Express a Fatty Acyl Hydroxylase cDNA from Castor Bean."

Nawrath et al., Proc. Natl. Acad. Sci. USA, 91:12760–12764, 1994, "Targeting of the Polyhydroxybutyrate Biosynthetic Pathway to the Plastids of Arabidopsis Thaliana Results in High Levels of Polymer Accumulation."

Nawrath et al, Biodegradable Plastics and Polymers, 1994, pp. 136–149, "Plastid Targeting of the Enzymes Required for the Production of Polyhydroxybutyrate in Higher Plants."

* cited by examiner

MULTIGENE EXPRESSION VECTORS FOR THE BIOSYNTHESIS OF PRODUCTS VIA MULTIENZYME BIOLOGICAL PATHWAYS

This application is based on U.S. Provisional Application No. 60/123,015, filed Mar. 5, 1999.

FIELD OF THE INVENTION

The invention relates to the construction and use of multigene expression vectors useful to enhance production of materials by multienzyme pathways. In particular, the construction and use of multigene vectors encoding proteins in the polyhydroxyalkanoate biosynthetic pathway is disclosed.

BACKGROUND OF THE INVENTION

Metabolic engineering is a process by which the normal metabolism of an organism is altered to change the concentration of normal metabolites, or to create novel metabolites. This process often involves introduction or alteration of numerous enzymatic steps, and thus often requires introduction of multiple genes. An efficient system for introducing and expressing multiple genes is therefore desirable. In prokaryotes such as *Escherichia coli*, introduction of multiple genes is relatively straightforward in that operons can be constructed to express multiple open reading frames, or multiple complete genes can be expressed from a single plasmid. However, introduction of pathways into plants is more difficult due in part to the complexity of plant genes, the difficulty of constructing vectors harboring multiple genes for expression in plants, and the difficulty of introducing large vectors intact into plants.

Polyhydroxyalkanoates are bacterial polyesters that accumulate in a wide variety of bacteria. These polymers have properties ranging from stiff and brittle plastics to rubber-like materials, and are biodegradable. Because of these properties, polyhydroxyalkanoates are an attractive source of non-polluting plastics and elastomers.

Currently, there are approximately a dozen biodegradable plastics in commercial use that possess properties suitable for producing a number of specialty and commodity products (Lindsay, *Modern Plastics* 2: 62, 1992). One such biodegradable plastic in the polyhydroxyalkanoate (PHA) family that is commercially important is Biopol™, a random copolymer of 3-hydroxybutyrate (3HB) and 3-hydroxyvalerate (3HV). This bioplastic is used to produce biodegradable molded material (e.g., bottles), films, coatings, and in drug release applications. Biopol™ is produced via a fermentation process employing the bacterium *Ralstonia eutropha* (Byrom, D. *Trends Biotechnol.* 5: 246–250, 1987). (*R. eutropha* was formerly designated *Alcaligenes eutrophus* [Yabuuchi et al., *Microbiol. Immunol.* 39:897–904, 1995]). The current market price is $6–7/lb, and the annual production is 1,000 tons. By best estimates, this price can be reduced only about 2-fold via fermentation (Poirier, Y. et al., *Bio/Technology* 13: 142, 1995). Competitive synthetic plastics such as polypropylene and polyethylene cost about 35–45¢/lb (Layman, *Chem. & Eng News, p.* 10 (Oct. 31, 1994). The annual global demand for polyethylene alone is about 37 million metric tons (Poirier, Y. et al., *Int. J. Biol. Macromol.* 17: 7–12, 1995). It is therefore likely that the cost of producing P(31HB-co-3HV) by microbial fermentation will restrict its use to low-volume specialty applications.

Polyhydroxyalkanoate (PHA) is a family of polymers composed primarily of R-3-hydroxyalkanoic acids (Anderson. A. J. and Dawes, E. A. *Microbiol. Rev.* 54: 450–472, 1990; Steinbüchel, A. in *Novel Biomaterials from Biological Sources,* ed. Byrom, D. (MacMillan, New York), pp. 123–213, 1991); Poirier, Y., Nawrath, C. & Somerville, C. *Bio/Technology* 13: 143–150, 1995). Polyhydroxybutyrate (PHB) is the most well-characterized PHA. High molecular weight PHB is found as intracellular inclusions in a wide variety of bacteria (Steinbüchel, A. in *Novel Biomaterials from Biological Sources,* ed. Byrom, D.: (MacMillan, New York), pp. 123–213, 1991). In *Ralstonia eutropha,* PHB typically accumulates to 80% dry weight with inclusions being typically 0.2–1 $\mu$m in diameter. Small quantity of PHB oligomers of approximately 150 monomer units are also found associated with membranes of bacteria and eukaryotes, where they form channels permeable to calcium (Reusch, R. N., *Can. J. Microbiol.* 41 (Suppl. 1): 50–54, 1995). High molecular weight polyhydroxyalkanoates have the properties of thermoplastics and elastomers. Numerous bacteria and fungi can hydrolyze polyhydroxyalkanoates to monomers and oligomers, which are metabolized as a carbon source. Polyhydroxyalkanoates have accordingly attracted attention as a potential source of renewable arid biodegradable plastics and elastomers. PHB is a highly crystalline polymer with rather poor physical properties, being relatively stiff and brittle (de Koning, G., *Can. J. Microbiol.* 41 (Suppl. 1): 303–309, 1995). In contrast, PHA copolymers containing monomer units ranging from 3 to 5 carbons for short-chain-length PHA (SCL-PHA), or 6 to 1,4 carbons for medium-chain-length PHA (MCL-PHA), are less crystalline and more flexible polymers (de Koning, G., *Can. J. Microbiol.* 41 (Suppl. 1): 303–309, 1995).

PHB has been produced in the plant *Arabidopsis thaliana* expressing the *R. eutropha* PHB biosynthetic enzymes (Poirier, Y. et al., *Science* 256: 520–523, 1992; Nawrath, C., et al., *Proc. Natl. Acad. Sci. U.S.A.* 91: 12760–12764, 1994). In plants expressing the. PHB pathway in the plastids, leaves accumulated up to 14% PHB per gram dry weight (Nawrath, C., et al., *Proc. Natl. Acad Sci. U.S.A.* 91: 12760–12764, 1994). High-level synthesis of PHB in plants opened the possibility of utilizing agricultural crops as a suitable system for the production of polyhydroxyalkanoates on a large scale and at low cost (Poirier, Y. et al., *Bio/Technology* 13: 143–150, 1995; Poirier, Y. et al., *FEMS Microbiol. Rev.* 103: 237–246, 1992; Nawrath, C., et al. *Molecular Breeding* 1: 105–22, 1995). PHB was also shown to be synthesized in insect cells expressing a mutant fatty acid synthase (Williams, M. D., et al., *Appl. Environ. Microbiol.* 62: 2540–2546, 1996), and in yeast expressing the *R. eutropha* PHB synthase (Leaf, T. A., et al. *Microbiol.* 142: 1169–1180, 1996).

A number of pseudomonads, including *Pseudomonas putida* and *Pseudomonas aeruginosa,* accumulate MCL-PHAs when cells are grown on alkanoic acids (Anderson, A. J. & Dawes, E. A. *Microbiol. Rev.* 54: 450–472, 1990; Steinb üchel, A. in *Novel Biomaterials from Biological Sources,* ed. Byrom, D. (MacMillan, New York), pp. 123–213, 1991; Poirier, Y., Nawrath, C. & Somerville, C. *Bio/Technology* 13: 143–150, 1995). The nature of the PHA produced is related to the substrate used for growth and is typically composed of monomers which are 2n carbons shorter than the substrate. These studies indicate that MCL-PHAs are synthesized by the PHA synthase from 3-hydroxyacyl-CoA intermediates generated by the β-oxidation of alkanoic acids (Huijberts, G. N. M., et al. *Appl. Environ. Microbiol.* 58: 536–544, 1992; Huijberts, G. N. M., et al., *J. Bacteriol.* 176: 1661–1666, 1994).

Chen et al. (*Nature Biotech.,* 16: 1060–1064, 1998; reviewed by Gelvin, S. B., *Nature Biotech.,* 16: 1009–1010, 1998) describes the cobombardment of embryogenic rice tissues with a mixture of 14 different pUC based plasmids. Integration of multiple transgenes was observed to occur at one or two genetic loci.

Creating a transgenic host cell or plant that produces multiple enzymes within a biosynthetic pathway is often a daunting task. Individual vectors must be created for each enzyme. Transformation of the host cell or plant is typically accomplished by one of three general methods: serial transformation, parallel transformation followed by crossing, or batch transformation. Each method has serious practical drawbacks.

Serial transformation involves transforming a host cell or plant with the first vector, selecting and characterizing the transformed cell or plant, transforming with the second vector, and so on. This process can become quite laborious and time consuming.

Parallel transformation followed by crossing involves separately transforming cells with each of the individual vectors, and subsequently mating or crossbreeding the transformed cells or plants to obtain a final cell or plant which contains all of the individual sequences. This is a lengthy process, especially for the crossbreeding of plant lines.

Batch transformation involves a single transformation event involving all of the individual vectors. A wide array of cells are produced, each containing between none and all of the vectors. While only a single transformation is required, extensive characterization of the resulting cells is necessary. As the number of vectors increases, it is increasingly likely that no cells will be obtained containing all of the vectors. If no desired transformed cells are identified, the transformation must be repeated.

An additional concern with all three of these methods is that they do not allow any control over the relative copy numbers of the individual vectors in the transformed cell or plant. It would be desirable to have a transformation method that permits control of the relative copy numbers of the individual sequences in the transformed cell or plant, and also coordinates the positional effect of the insertion locus.

There exists a need for improved materials and methods for the preparation of transgenic organisms transformed with multiple nucleic acid sequences encoding members of a multi-enzyme biosynthetic pathway.

SUMMARY OF THE INVENTION

The invention involves the construction and use of nucleic acid segments and vectors containing multiple sequences encoding members of a biosynthetic pathway. The resulting vector allows a single transformation event to produce a transformed cell or plant containing all of the nucleic acid sequences. Furthermore, the researcher has total control over the number of copies of each coding sequence within the constructed vector. Single or multiple copies of each coding sequence may easily be designed into the vector.

An unexpected beneficial result of the invention is that organisms transformed with a multi-enzyme coding vector produce the biosynthetic product in higher yield than organisms produced by serial transformation, parallel transformation with crossing, or batch transformation methods.

DETAILED DESCRIPTION OF THE INVENTION

The invention is directed generally towards the construction and use of nucleic acid segments comprising sequences encoding multiple enzymes in a multi-enzyme biosynthetic pathway. The biosynthetic pathway may generally be any biosynthetic pathway. Examples of such multi-enzyme biosynthetic pathways are the TCA cycle, polyketide synthesis pathway, carotenoid synthesis, glycolysis, gluconeogenesis, starch synthesis, lignins and related compounds, production of small molecules that serve as pesticides, fungicides, or antibiotics, and polymer synthesis pathways. Preferably, the biosynthetic pathway is a polyhydroxyalkanoate biosynthesis pathway.

This disclosure describes multigene vectors designed to produce polyhydroxyalkanoate (PHA) in plants. Some of these vectors are designed to produce poly(β-hydroxybutyrate), and some are designed to produce poly (β-hydroxybutyrate-co-β-hydroxyvalerate) (Gruys et al., WO 98/00557, 1998). In general, the efficiency of PHA production was dramatically increased when all sequences necessary for a pathway were introduced on the same vector. Herein, construction of these multigene vectors, and their use for polyhydroxyalkanoate production in *Arabidopsis thaliana* and *Brassica napus,* and *Zea mays* is described.

An embodiment of the present invention is an isolated nucleic acid segment comprising multiple nucleic acid sequences, each encoding a different protein within the biosynthetic pathway. Preferably, the isolated nucleic acid segment comprises a first nucleic acid sequence encoding a polyhydroxyalkanoate synthase protein; a second nucleic acid sequence encoding a β-ketoacyl reductase protein; and a third nucleic acid sequence encoding a β-ketothiolase protein. The nucleic acid segment may further comprise additional nucleic acid sequences encoding additional proteins such as a threonine deaminase protein or a deregulated threonine deaminase protein.

An alternative embodiment of the invention is a recombinant vector comprising multiple nucleic acid sequences, each encoding a different protein within the biosynthetic pathway. The recombinant vector may be arranged with a single promoter producing a polycistronic RNA transcript from the multiple nucleic acid sequences, or with each nucleic acid sequence being under the control of its own promoter. The multiple promoters may be the same or different. It is also possible to have one or more nucleic acid sequence under the control of its own promoter, while other nucleic acid sequences may be jointly under the control of a single promoter producing a polycistronic RNA transcript.

A recombinant vector placing the biosynthetic pathway nucleic acid sequences under the control of a single promoter preferably comprises operatively linked in the 5' to 3' direction: a promoter that directs transcription of the first nucleic acid sequence, second nucleic acid sequence, and third nucleic acid sequence; a first nucleic acid sequence; a second nucleic acid sequence; a third nucleic acid sequence; a 3' transcription terminator; and a 3' polyadenylation signal sequence; wherein: the first nucleic acid sequence, second nucleic acid sequence, and third nucleic acid sequence encode different proteins; and the first nucleic acid sequence, second nucleic acid sequence, and third nucleic acid sequence are independently selected from the group consisting of a nucleic acid sequence encoding a polyhydroxyalkanoate synthase protein, a nucleic acid sequence encoding a β-ketoacyl reductase protein, and a nucleic acid sequence encoding a β-ketothiolase protein. The nucleic acid sequences encoding the biosynthetic pathway enzymes may be in any order relative to each other and the promoter. The promoter must be expressed in plastids. It may have either been derived from a plastid, or may have been derived from a bacterium or phage having promoters recognized by the plastid transcription enzymes, or be a synthetic promoter recognized by the plastid transcription enzymes.

A recombinant vector placing the biosynthetic pathway nucleic acid sequences under the control of multiple promoters preferably comprises a first element comprising operatively linked in the 5' to 3' direction: a first promoter that directs transcription of the first nucleic acid sequence; a first nucleic acid sequence encoding a polyhydroxyalkanoate synthase protein; a first 3' transcription terminator; a first 3' polyadenylation signal sequence; a second element comprising operatively linked in the 5' to 3' direction: a second promoter that directs transcription of the second nucleic acid sequence; a second nucleic acid sequence encoding a β-ketoacyl reductase protein; a second 3' transcription terminator; a second 3' polyadenylation signal sequence; and a third element comprising operatively linked in the 5' to 3' direction: a third promoter that directs transcription of the third nucleic acid sequence; a third nucleic acid sequence encoding a β-ketothiolase protein; a third 3' transcription terminator; and a third 3' polyadenylation signal sequence. The β-ketothiolase protein preferably condenses two molecules of acetyl-CoA to produce acetoacetyl-CoA; and condenses acetyl-CoA and propionyl-CoA to produce β-ketovaleryl-CoA. The β-ketoacyl reductase protein preferably reduces acetoacetyl-CoA to β-hydroxybutyryl-CoA; and reduces β-ketovaleryl-CoA to β-hydroxyvaleryl-CoA. The polyhydroxyalkanoate synthase protein is preferably selected from the group consisting of: a polyhydroxyalkanoate synthase protein that incorporates β-hydroxybutyryl-CoA into P(3HB) polymer; and a polyhydroxyalkanoate synthase protein that incorporates a β-hydroxybutyryl-CoA and a β-hydroxyvaleryl-CoA into P(3HB-co-3HV) copolymer. The β-ketothiolase protein may comprise a transit peptide sequence that directs transport of the β-ketothiolase protein to the plastid. The β-ketoacyl reductase protein may comprise a transit peptide sequence that directs transport of the β-ketoacyl reductase protein to the plastid. The polyhydroxyalkanoate synthase protein may comprise a transit peptide sequence that directs transport of the polyhydroxyalkanoate synthase protein to the plastid. The recombinant vector may further comprise a nucleic acid sequence encoding a threonine deaminase protein or a deregulated threonine deaminase protein. The first promoter, second promoter, and third promoter are preferably active in plants. The first promoter, second promoter, and third promoter are preferably viral promoters. The first promoter, second promoter, and third promoter are preferably independently selected from the group consisting of a CMV 35S promoter, an enhanced CMV 35S promoter, maize chlorophyll A/B binding protein promoter, and an FMV 35S promoter. More preferably, the first promoter, second promoter, and third promoter are the CMV 35S promoter. The first promoter: second promoter, and third promoter may be tissue specific promoters. The first promoter, second promoter, and third promoter may independently be the Lesquerella hydroxylase promoter or the 7S conglycinin promoter, and preferably each is the Lesquerella hydroxylase promoter.

An alternative embodiment is directed towards transformed host cells. Transformed host cells may contain a non-integrated recombinant vector or an integrated recombinant vector.

A transformed host cell may comprise a recombinant vector, wherein the recombinant vector comprises a first element comprising operatively linked in the 5' to 3' direction: a first promoter that directs transcription of the first nucleic acid sequence; a first nucleic acid sequence encoding a polyhydroxyalkanoate synthase protein; a first 3' transcription terminator; a first 3' polyadenylation signal sequence; a second element comprising operatively linked in the 5' to 3' direction: a second promoter that directs transcription of the second nucleic acid sequence; a second nucleic acid sequence encoding a β-ketoacyl reductase protein; a second 3' transcription terminator; a second 3' polyadenylation signal sequence; and a third element comprising operatively linked in the 5' to 3' direction a third promoter that directs transcription of the third nucleic acid sequence; a third nucleic acid sequence encoding a β-ketothiolase protein; a third 3' transcription terminator; and a third 3' polyadenylation signal sequence.

The transformed host cell may alternatively contain an integrated nucleic acid segment. Preferably, the transformed host cell may comprise a first element comprising operatively linked in the 5' to 3' direction: a first promoter that directs transcription of a first nucleic acid sequence; a first nucleic acid sequence encoding a polyhydroxyalkanoate synthase protein; a first 3' transcription terminator; a first 3' polyadenylation signal sequence; a second element comprising operatively linked in the 5' to 3' direction: a second promoter that directs transcription of a second nucleic acid sequence; a second nucleic acid sequence encoding a β-ketoacyl reductase protein; a second 3' transcription terminator; a second 3' polyadenylation signal sequence; and a third element comprising operatively linked in the 5' to 3' direction: a third promoter that directs transcription of a third nucleic acid sequence; a third nucleic acid sequence encoding a β-ketothiolase protein; a third 3' transcription terminator; and a third 3' polyadenylation signal sequence. The first element, second element, and third element may be cointegrated within a continuous 10 Mb segment of genomic DNA, more preferably within a continuous 5 Mb, 2.5 Mb, 2 Mb, 1.5 Mb, 1 Mb, 500 kb, 250 kb, 100 kb, 50 kb, or 20 kb segment of genomic DNA. Alternatively, the first element, second element, and third element may be cointegrated between a left Ti border sequence and a right Ti border sequence. While it is preferable that a recombinant vector contain a single left Ti border sequence and a single right Ti border sequence, the invention encompasses recombinant vectors containing multiple left and/or right Ti border sequences, and the use thereof FIG. 2C.

Alternatively, the host cell may comprise a nucleic acid segment containing nucleic acid sequences encoding enzymes in a biosynthetic pathway, where a single promoter directs transcription of the nucleic acid sequences.

The transformed host cell may generally be any host cell, and preferably is a bacterial, fungal, or plant cell. The bacterial cell is preferably an *Escherichia coli* cell. The fungal cell is preferably a yeast, *Saccharomyces cerevisiae*, or *Schizosaccharomyces pombe* cell. The plant cell may be a monocot plant cell, a dicot plant cell, an algae cell, or a conifer plant cell. The plant cell is preferably a tobacco, wheat, potato, Arabidopsis, corn, soybean, canola, sugar beet, oil seed rape, sunflower, flax, peanut, sugarcane, switchgrass, or alfalfa cell.

The promoters may be any of the promoters discussed earlier. The transformed host cells preferably produce polyhydroxyalkanoate polymer.

The invention also encompasses transformed plants. The transformed plant may contain an integrated set of nucleic acid sequences, or may contain the same set of nucleic acid sequences on a non-integrated vector. A preferred embodiment is directed towards a transformed plant comprising a first element comprising operatively linked in the 5' to 3' direction: a first promoter that directs transcription of a first nucleic acid sequence; a first nucleic acid sequence encoding a polyhydroxyalkanoate synthase protein; a first 3' transcription terminator; a first 3' polyadenylation signal sequence; a second element comprising operatively linked in the 5' to 3' direction: a second promoter that directs transcription of a second nucleic acid sequence; a second nucleic acid sequence encoding a β-ketoacyl reductase protein; a second 3' transcription terminator; a second 3' polyadenylation signal sequence; and a third element comprising operatively linked in the 5' to 3' direction: a third promoter that directs transcription of a third nucleic acid sequence; a third nucleic acid sequence encoding a β-ketothiolase protein; a third 3' transcription terminator; and a third 3' polyadenylation signal sequence. The first element, second element, and third element may be cointegrated within a continuous 10 Mb segment of genomic DNA, more preferably within a continuous 5 Mb, 2.5 Mb, 2 Mb, 1.5 Mb, 1 Mb, 500 kb, 250 kb, 100 kb, 50 kb, or 20 kb segment of genomic DNA. Alternatively, the first element, second element, and third element may be cointegrated between a left Ti border sequence and a right Ti border sequence FIG. 2C.

Alternatively, the transformed plant may comprise a nucleic acid segment containing nucleic acid sequences encoding enzymes in a biosynthetic pathway, where a single promoter directs transcription of the nucleic acid sequences.

The transformed plant may generally be any type of plant, and preferably is a tobacco, wheat, potato, Arabidopsis, corn, soybean, canola, oil seed rape, sunflower, flax, peanut, sugarcane, switchgrass, or alfalfa plant.

The promoters may be any of the promoters discussed earlier. The transformed plant preferably produces polyhydroxyalkanoate polymer.

The invention also encompasses methods of preparing transformed host cells. The methods may produce a transformed host cell having nucleic acid sequences under the control of multiple promoters or under the control of a single promoter. The method preferably comprises the steps of selecting a host cell; transforming the selected host cell with a recombinant vector comprising: a first element comprising operatively linked in the 5' to 3' direction: a first promoter that directs transcription of the first nucleic acid sequence; a first nucleic acid sequence encoding a polyhydroxyalkanoate synthase protein; a first 3' transcription terminator; a first 3' polyadenylation signal sequence; a second element comprising operatively linked in the 5' to 3' direction: a second promoter that directs transcription of the second nucleic acid sequence; a second nucleic acid sequence encoding a β-ketoacyl reductase protein; a second 3' transcription terminator; a second 3' polyadenylation signal sequence; and a third element comprising operatively linked in the 5' to 3' direction: a third promoter that directs transcription of the third nucleic acid sequence; a third nucleic acid sequence encoding a β-ketothiolase protein; a third 3' transcription terminator; and a third 3' polyadenylation signal sequence; and obtaining transformed host cells; wherein the transformed host cells produce polyhydroxyalkanoate polymer.

Alternatively, the method of preparing transformed host cells may comprise the steps of selecting a host cell: transforming the selected host cell with a recombinant vector comprising operatively linked in the 5' to 3' direction: a promoter that directs transcription of a first nucleic acid sequence, second nucleic acid sequence, and third nucleic acid sequence; a first nucleic acid sequence; a second nucleic acid sequence; a third nucleic acid sequence; a 3' transcription terminator; and a 3' polyadenylation signal sequence; and obtaining transformed host cells; wherein: the first nucleic acid sequence, second nucleic acid sequence, and third nucleic acid sequence encode different proteins; the first nucleic acid sequence, second nucleic acid sequence, and third nucleic acid sequence are independently selected from the group consisting of a nucleic acid sequence encoding a polyhydroxyalkanoate synthase protein, a nucleic acid sequence encoding a β-ketoacyl reductase protein, and a nucleic acid sequence encoding a β-ketothiolase protein; and the transformed host cells produce polyhydroxyalkanoate polymer.

The promoters may be any of the promoters discussed earlier.

Also disclosed are methods for preparing transformed plants. The methods may produce a transformed plant having nucleic acid sequences under the control of multiple promoters or under the control of a single promoter. The method preferably comprises the steps of selecting a host plant cell; transforming the selected host plant cell with a recombinant vector comprising: a first element comprising operatively linked in the 5' to 3' direction: a first promoter that directs transcription of a first nucleic acid sequence; a first nucleic acid sequence encoding a polyhydroxyalkanoate synthase protein; a first 3' transcription terminator; and a first 3' polyadenylation signal sequence; a second element comprising operatively linked in the 5' to 3' direction: a second promoter that directs transcription of a second nucleic acid sequence; a second nucleic acid sequence encoding a β-ketoacyl reductase protein; a second 3' transcription terminator; and a second 3' polyadenylation signal sequence; and a third element comprising operatively linked in the 5' to 3' direction: a third promoter that directs transcription of a third nucleic acid sequence; a third nucleic acid sequence encoding a β-ketothiolase protein; a third 3' transcription terminator; and a third 3' polyadenylation signal sequence; obtaining transformed host plant cells; and regenerating the transformed host plant cells to produce transformed plants, wherein the transformed plants produce polyhydroxyalkanoate polymer.

Alternatively, the method of preparing a transformed plant may comprise the steps of selecting a host plant cell; transforming the selected host plant cell with a recombinant vector comprising operatively linked in the 5' to 3' direction: a promoter that directs transcription of a first nucleic acid sequence, second nucleic acid sequence, and third nucleic acid sequence; a first nucleic acid sequence; a second nucleic acid sequence; a third nucleic acid sequence; a 3' transcription terminator; and a 3' polyadenylation signal sequence; obtaining transformed host plant cells; and regenerating the transformed host plant cells to produce transformed plants; wherein: the first nucleic acid sequence, second nucleic acid sequence, and third nucleic acid sequence encode different proteins; the first nucleic acid sequence, second nucleic acid sequence, and third nucleic acid sequence are independently selected from the group consisting of a nucleic acid sequence encoding a polyhydroxyalkanoate synthase protein, a nucleic acid sequence encoding a β-ketoacyl reductase protein, and a nucleic acid sequence encoding a β-ketothiolase protein; and the transformed plants produce polyhydroxyalkanoate polymer.

The promoters may be any of the promoters discussed earlier.

The invention is also directed towards methods of producing biomolecules of interest. The imultiple enzymes in the biosynthetic pathway may lead to the production of materials of commercial and scientific interest. Preferably, the biomolecules are polymers, and more preferably are polyhydroxyalkanoate polymers. The methods may comprise obtaining any of the above described transformed host cells or transformed plants, culturing or growing the transformed host cells or transformed plants under conditions suitable for the production of polyhydroxyalkanoate polymer, and recovering polyhydroxyalkanoate polymer. The methods may further comprise the addition of nutrients, substrates, or other chemical additives to the growth media or soil to facilitate production of polyhydroxyalkanoate polymer. In a preferred embodiment, it is possible to extract the polyhydroxyalkanoate from the transformed host cells or transformed plants without killing the host cells or plants. This may be accomplished, for example, by various solvent extraction methods or by engineering the host cells or plants to secrete the polyhydroxyalkanoate polymer, or by directing production to tissues such as leaves or seeds which may be removed without causing serious injury to the plant. The polyhydroxyalkanoate polymer produced is preferably poly (3-hydroxybutyrate), poly(3-hydroxybutyrate-co-3-hydroxyvalerate), poly(4-hydroxybutyrate), or poly(3-hydroxybutyrate-co-4-hydroxybutyrate).

If repetitive sequences are used in a multi-gene plasmid system, there exists the possibility for gene silencing in subsequent generations of plants. If expression levels are high gene silencing could also occur and would be independent of repetitive elements. Repetitive sequences may include the use of the same promoters, chloroplast peptide encoding sequences, and other genetic elements for each of the multi-gene coding sequences. Gene silencing often manifests itself as a gradual reduction in protein levels, mRNA levels, or biosynthesis product concentrations in subsequent generations of related plants. If gene silencing is observed, changing the repetitive sequences through the use of diverse genetic elements such as different promoters, leaders, introns, transit peptide sequences, etc., different designed nucleotide sequence, or through mutagenesis of the existing sequence, may be successful in reducing or eliminating the gene silencing effects.

DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

DEFINITIONS

Figure 1:
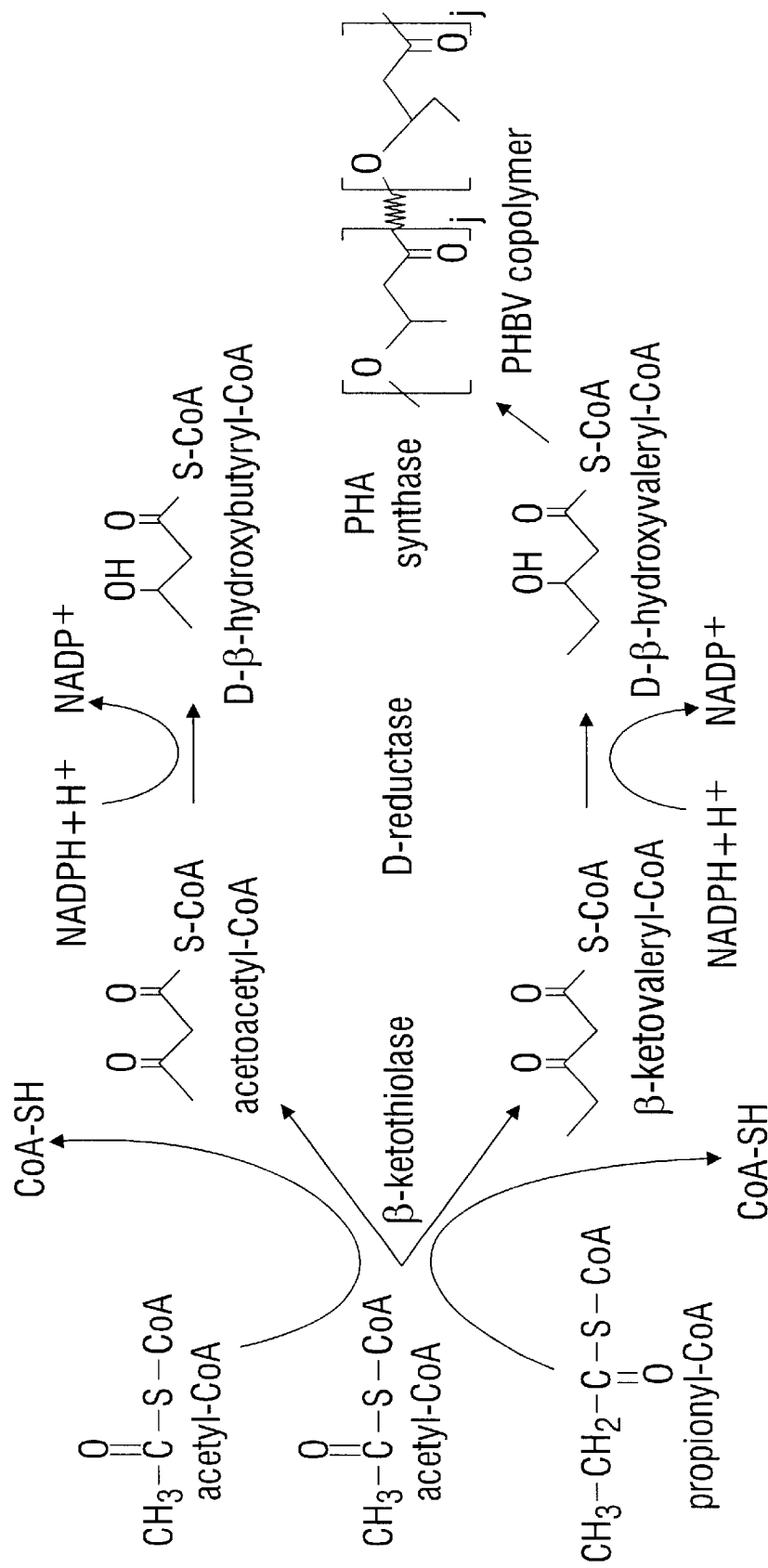
FIG. 1: Biosynthesis of poly(β-hydroxybutyrate-co-β-hydroxyvalerate) (poly(3HB-co-3HV), PHBV) in *Ralstonia eutropha*.

The following definitions are provided in order to aid those skilled in the art in understanding the detailed description of the present invention.

"Acyl-ACP thioesterase" refers to proteins which catalyze the hydrolysis of acyl-ACP thioesters.

"C-terminal region" refers to the region of a peptide, polypeptide, or protein chain from the middle thereof to the end that carries the amino acid having a free a carboxyl group (the C-terminus).

"CoA" refers to coenzyme A.

The phrases "coding sequence", "open reading frame", and "structural sequence" refer to the region of continuous sequential nucleic acid triplets encoding a protein, polypeptide, or peptide sequence.

The term "encoding DNA" or "encoding nucleic acid" refers to chromosomal nucleic acid, plasmid nucleic acid, cDNA, or synthetic nucleic acid which codes on expression for any of the proteins or fusion proteins discussed herein.

"Fatty acyl hydroxylase" refers to proteins which catalyze the conversion of fatty acids to hydroxylated fatty acids.

The term "genome" as it applies to bacteria encompasses both the chromosome and plasmids within a bacterial host cell. Encoding nucleic acids of the present invention introduced into bacterial host cells can therefore be either chromosomally-integrated or plasmid-localized. The term "genome" as it applies to plant cells encompasses not only chromosomal DNA found within the nucleus, but organelle DNA found within subcellular components of the cell. Nucleic acids of the present invention introduced into plant cells can therefore be either chromosomally-integrated or organelle-localized.

"Identity" refers to the degree of similarity between two nucleic acid or protein sequences. An alignment of the two sequences is performed by a suitable computer program. A widely used and accepted computer program for performing sequence alignments is CLUSTALW v1.6 (Thompson, et al. *Nucl. Acids Res.*, 22: 4673–4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between 200 and a 400 amino acid proteins, they are 50 percent identical with respect to the shorter sequence. If the shorter sequence is less than 150 bases or 50 amino acids in length, the number of matches are divided by 150 (for nucleic acids) or 50 (for proteins); and multiplied by 100 to obtain a percent identity.

The terms "microbe" or "microorganism" refer to algae, bacteria, fungi, and protozoa.

"N-terminal region" refers to the region of a peptide, polypeptide, or protein chain from the amino acid having a free a amino group to the middle of the chain.

"Nucleic acid" refers to ribonucleic acid (RNA) and deoxyribonucleic acid (DNA).

A "nucleic acid segment" is a nucleic acid molecule that has been isolated free of total genomic DNA of a particular species, or that has been synthesized. Included with the term "nucleic acid segment" are DNA segments, recombinant vectors, plasmids, cosmids, phagemids, phage, viruses, etcetera.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

The term "plastid" refers to the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and whichusually contains an inverted repeat region (Fosket, Plant growth and Development, Academic Press, Inc., San Diego, Calif., p. 132, 1994).

"Polyadenylation signal" or "polyA signal" refers to a nucleic acid sequence located 3' to a coding region that directs the addition of adenylate nucleotides to the 3' end of the mRNA transcribed from the coding region.

The term "polyhydroxyalkanoate (or PHA) synthase" refers to enzymes that convert hydroxyacyl-CoAs to polyhydroxyalkanoates and free CoA.

The term "promoter" or "promoter region" refers to a nucleic acid sequence, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

"Regeneration" refers to the process of growing a plant from a plant cell (e.g., plant protoplast or explant).

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

A "transformed cell" is a cell whose nucleic acid has been altered by the introduction of an exogenous nucleic acid molecule into that cell.

A "transformed plant" or "transgenic plant" is a plant whose nucleic acid has been altered by the introduction of an exogenous nucleic acid molecule into that plant, or by the introduction of an exogenous nucleic acid molecule into a plant cell from which the plant was regenerated or derived.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Sources of Nucleic Acid Sequences

Nucleic, acid sequences encoding the polyhydroxyalkanoate biosynthetic pathway include: phbA and phbB (GenBank accession number J04987), phbC (GenBank accession number J05003), and bktB (GenBank accession number AF026544). Production of PHBV copolymer can be accomplished by also expressing E. coli ilvA (GenBank accession number U00096, overlapping base 3953951:Gruys et al. WO 98/00557). The Ti DNA left border sequence is described in Baker, R. F., et al. (*Plant Mol. Biol.,* 2: 335–350, 1983). The Ti DNA right border sequence is described in Depicker et. al. (*J. Mol. App. Genet.* 1: 561, 1982).

Example 2

Analysis of Nawrath Arabidopsis Plants

Figure 2A:
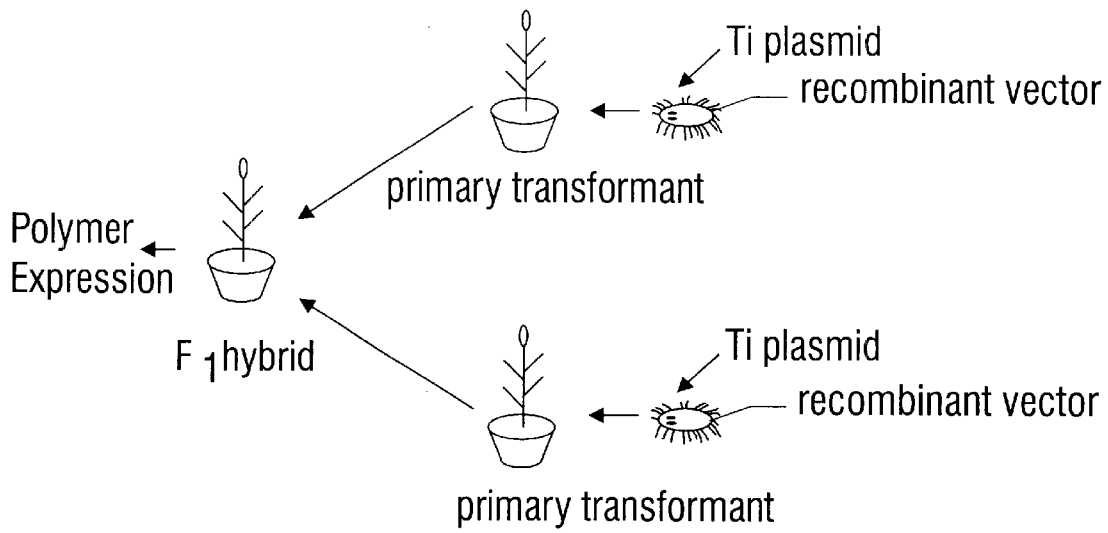
FIG. 2A: Polymer expression in plants using a single vector and cross-hybridization strategy.

Polyhydroxyalkanoates are a form of polyester accumulated by numerous bacterial species as a carbon and energy repository. This class of polymer also has useful thermoplastic properties, and is therefore of interest as a biodegradable plastic. Poly(β-hydroxybutyrate-co-β-hydroxyvalerate) (poly(3HB-co-3HV), PHBV), a form of PHA, is commercially produced via fermentation of *Ralstonia eutropha* (FIG. 1). However, it is expected that the cost of production could be dramatically decreased if PHA could be produced in transgenic plants. The first attempts at PHA production in plants utilized transgenic Arabidopsis expressing the three genes required for the homopolymer poly-β-hydroxybutyrate (PHB) (Nawrath, C. et al., *Proc. Natl. Acad Sci. USA.* 91: 12760–12764, 1994). In this work, the authors transformed Arabidopsis plants with three independent gene cassettes and crossed the plants using traditional breeding methods (FIG. 2A). They reported PHB production up to 14% of the cell dry weight. However, this method took a significant amount of time before the three gene pathway could be assembled. In addition, the plants did not maintain a stable phb⁻ phenotype, as determined by our analysis of the progeny of these original plants (Table 1). This problem may be due to co- suppression (Finnegan, J., and D. McElroy. *Bio/Technology.* 12: 883–888, 1994), or to segregation of high-producing insertions in the progeny. The plants produced by Nawrath et al. were not fully characterized genetically, although it is known that all contained multiple insertions of the transgenes.

TABLE 1

Enzyme activity and polymer data of progeny of Nawrath *Arabidopsis* lines.

| plant line number | [protein] (mg/mL) | Specific activities | | Western results | | | % polymer (C4) |
|---|---|---|---|---|---|---|---|
| | | thiolase (u/mg) | reductase (u/mg) | PhbA thiolase | PhbB reductase | PhbC synthase | |
| 134 | 0.158 | 0.027 | 0.069 | + | + | − | 0.041% |
| 140 | 0.189 | 0.026 | 0.019 | + | + | − | 0.068% |
| 151 | 0.377 | 0.042 | 0.045 | + | + | + | 0.038% |
| 159 | 0.127 | 0.025 | 0.009 | − | − | + | 0.053% |
| 168 | 0.216 | 0.018 | 0.034 | + | + | + | 0.070% |
| 175 | 0.186 | 0.010 | 0.028 | + | − | − | 0.043% |
| 177 | 0.166 | 0.026 | 0.000 | + | − | − | 0.043% |
| 203 | 0.144 | 0.030 | 0.043 | − | + | + | 0.034% |
| 228 | 0.250 | 0.038 | 0.021 | + | + | + | 0.048% |
| 240 | 0.192 | 0.023 | 0.010 | NA | NA | NA | 0.045% |

Example 3
Use of Multiple Vectors to Introduce PHA Biosynthesis Sequences into Arabidopsis One vector was constructed containing sequences encoding both acetoacetyl-CoA reductase and PHB synthase proteins. A second vector was constructed containing a sequence encoding a β-ketothiolase protein. Two independent transformation events were obtained corresponding to each of these vectors. The complete pathway was assembled into a single plant using traditional cross-breeding methods. In all cases, plants exhibiting Mendelian segregation consistent with transgene insertion at a single locus were chosen. The results of these experiments are shown in Table 2.

Figure 2B:
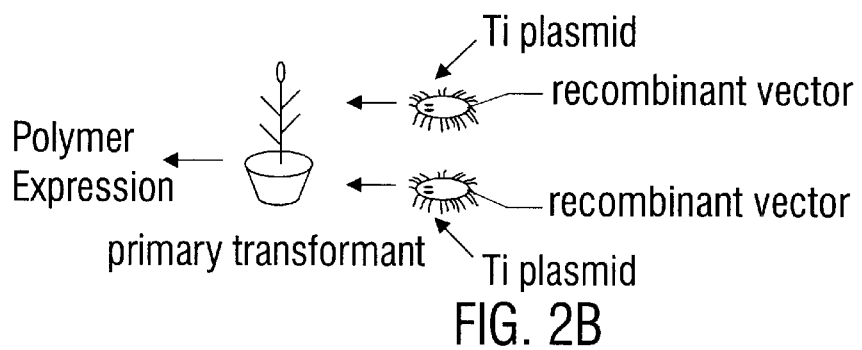
FIG. 2B: Polymer expression in plants using a multiple vector strategy.
Figure 2C:
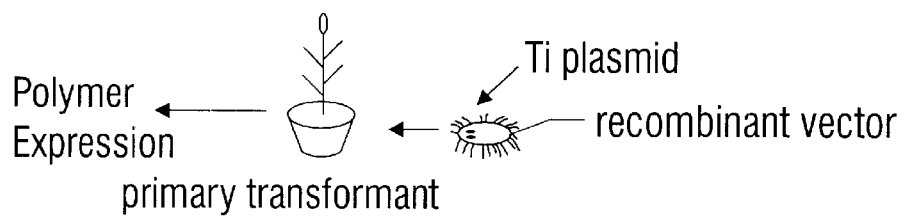
FIG. 2C: Polymer expression in plant using a single multigene vector strategy.

The second strategy pursued was to simultaneously co-transform both plasmids into a single plant (simultaneous co-transformation) and assay the primary transformant for polymer accumulation, or to re-transform plants that already harbored a single vector (serial co- transformation) (FIG. 2B). The results of these experiments are summarized in Table 3. Although the activity of enzymes expressed from the encoding sequences was comparable to that reported by Nawrath et al., none of the plants generated reached the polymer levels reportedly achieved in their study. Neither their experiments nor these results correlate enzyme activity with the intracellular concentration of PHA polymer (Nawrath, C. et al., *Proc. Natl. Acad. Sci. U.S.A.* 91: 12760–12764, 1994).

TABLE 2

Polymer data for Arabidopsis crosses.

| Vector Number | Plant construct description | # of lines assayed | # of lines positive | C4 polymer (% cell dry wt.) |
|---|---|---|---|---|
| 25640 | e35s ctpl phbA | | | 0.01–1.55% |
| 25665 | e35s ctpl phbC e35s ctpl phbB | 11 | 10 | AVE: 0.651% SD: 0.596% |
| 25640 | e35s ctpl phbA | | | 0.03–0.047% |
| 25739 | e35s ctpl phbB e35s ctpl nocC | 20 | 12 | AVE: 0.178% SD: 0.163% |
| 25785 | e35s ctpl bktB | | | 0.04–0.88% |
| 25665 | e35s ctpl phbC e35s ctpl phbB | 11 | 11 | AVE: 0.354% SD: 0.199% |
| 25785 | e35s ctpl bktB | | | 0.03–0.21% |
| 25739 | e35s ctpl phbB e35s ctpl nocC | 24 | 9 | AVE: 0.065% SD: 0.053% |
| 25801 | e35s ctpl bktB e35s ctpl ilvA466 | 8 | 3 | 0.02–0.04% AVE: 0.029% SD: 0.0095% |
| 25665 | e35s ctpl phbC | | | |

TABLE 2-continued

Polymer data for Arabidopsis crosses.

| Vector Number | Plant construct description | # of lines assayed | # of lines positive | C4 polymer (% cell dry wt.) |
|---|---|---|---|---|
| 25801 | e35s ctpl phbB e35s ctpl bktB e35s ctpl ilvA466 | 17 | 9 | 0.03–0.091% AVE: 0.044% SD: 0.022% |
| 25739 | e35s ctpl phbB e35s ctpl nocC | | | |
| 25812 | e35s ctpl bktB e35s ctpl ilvA w.t. | 3 | 3 | 0.03–0.102% AVE: 0.073% SD: 0.035% |
| 25665 | e35s ctpl phbC e35s ctpl phbB | | | |
| 25812 | e35s ctpl bktB e35s ctpl ilvA w.t. | 10 | 7 | 0.02–0.11% AVE: 0.064% SD: 0.031% |
| 25739 | e35s ctpl phbB e35s ctpl nocC | | | |

64/104 plants positive; AVE = average; SD = standard deviation.

TABLE 3

Polymer data for re-transformed and co-transformed Arabidopsis.

| Vector number | Plant construct description | # of lines assayed | # of lines positive | C4 polymer (% cell dry wt.) |
|---|---|---|---|---|
| 25665 | e35s ctpl phbC e35s ctpl phbB | 14 | 6 | 0.03–0.81% AVE: 0.25% SD: 0.29% |
| RE/25880 | e35s ctpl bktB e35s ctpl ilvA w.t. | | | |
| 25665 | e35s ctpl phbC e35s ctpl phbB | 5 | 0 | NA |
| RE/25881 | e35s ctpl bktB e35s ctpl ilvA219 | | | |
| 25665 | e35s ctpl phbC e35s ctpl phbB | 23 | 4 | 0.02–0.33% AVE: 0.16% SD: 1.3% |
| RE/25882 | e35s ctpl bktB e35s ctpl ilvA466 | | | |
| 25785 | e35s ctpl bktB | | | 0.02–1.67% |
| 25678 | e35s ctpl phbB e35s ctpl phbC | 21 | 8 | AVE: 0.50% SD: 0.64% |
| 25785 | e35s ctpl bktB | | | 0.01–0.72% |
| 25740 | e35s ctpl phbB e35s ctpl nocC | 27 | 18 | AVE: 0.11 SD: 0.15 |
| 25801 | e35s ctpl bktB e35s ctpl ilvA466 | 2 | 1 | 0.646–0.715% AVE: 0.681 |
| 25678 | e35s ctpl phbB e35s ctpl phbC | | | SD: 0.049% |
| 25801 | e35s ctpl bktB e35s ctpl ilvA466 | 28 | 16 | 0.02–0.17% AVE: 0.083% SD: 0.050% |
| 25740 | e35s ctpl phbB e35s ctpl nocC | | | |

TABLE 3-continued

Polymer data for re-transformed and co-transformed Arabidopsis.

| Vector number | Plant construct description | # of lines assayed | # of lines positive | C4 polymer (% cell dry wt.) |
|---|---|---|---|---|
| 25812 | e35s ctpl bktB e35s ctpl ilvA w.t. | 3 | 3 * | 0.63–1.65% AVE: 1.191% |
| 25678 | e35s ctpl phbB e35s ctpl phbC | | | SD: 0.463% |
| 25812 | e35s ctpl bktB e35s ctpl ilvA w.t. | 30 | 9 | 0.02–0.20% AVE: 0.112% |
| 25740 | e35s ctpl phbB e35s ctpl nocC | | | SD: 0.053% |

64/145 plants positive.
RE indicates that this vector was used to re-transform a plant line.
AVE = average.
SD = standard deviation.

Figure 4:
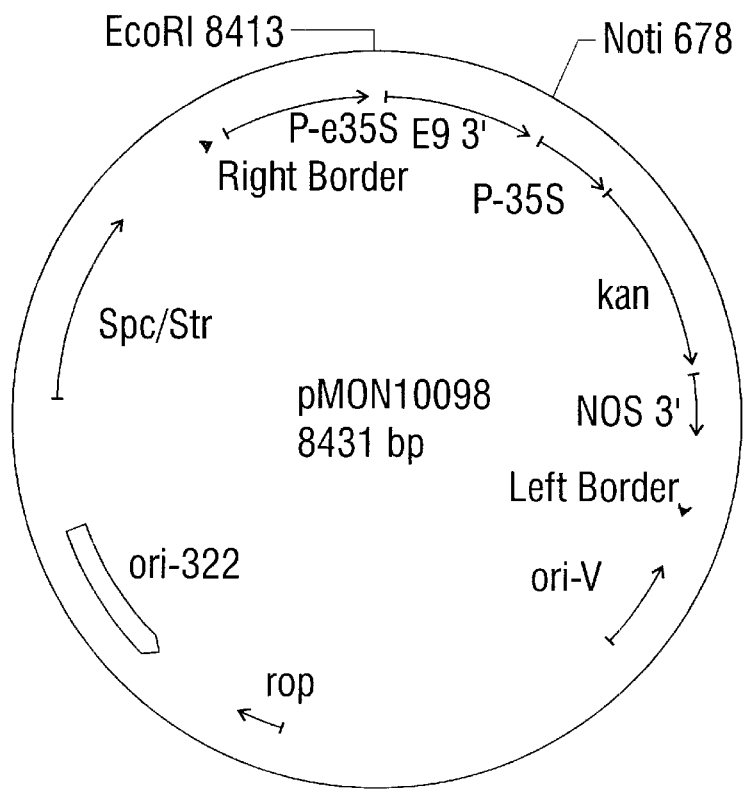
FIG. 4: Plasmid map of pMON10098. A list of the restriction enzyme cutting sites for pMON10098 is provided in Table 11.
Figure 5:
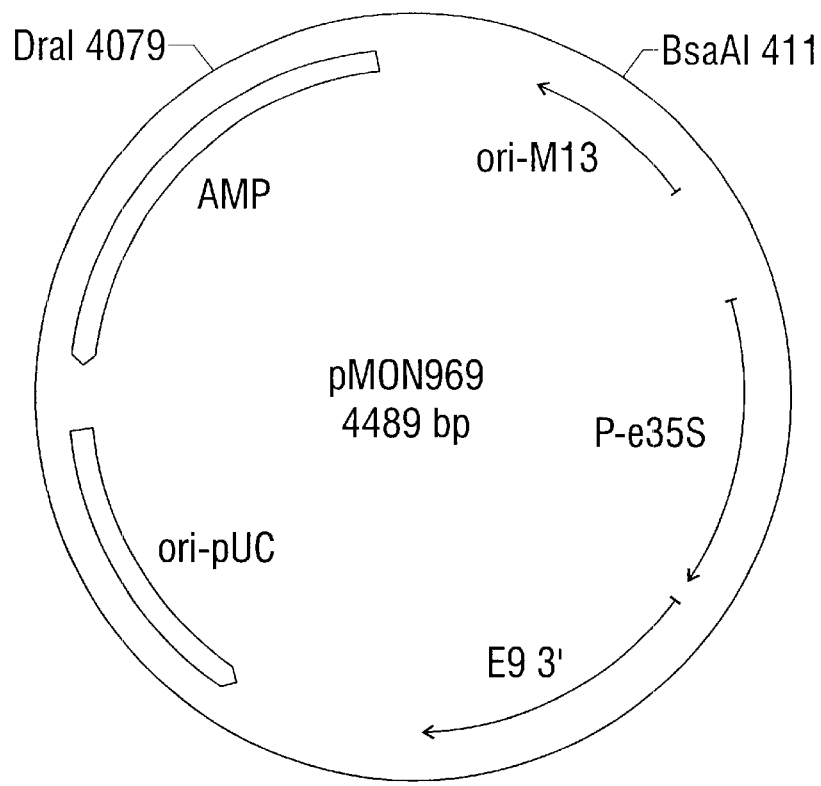
FIG. 5: Plasmid map of pMON969. A list of the restriction enzyme cutting sites for pMON969 is provided in Table 12.
Figure 6:
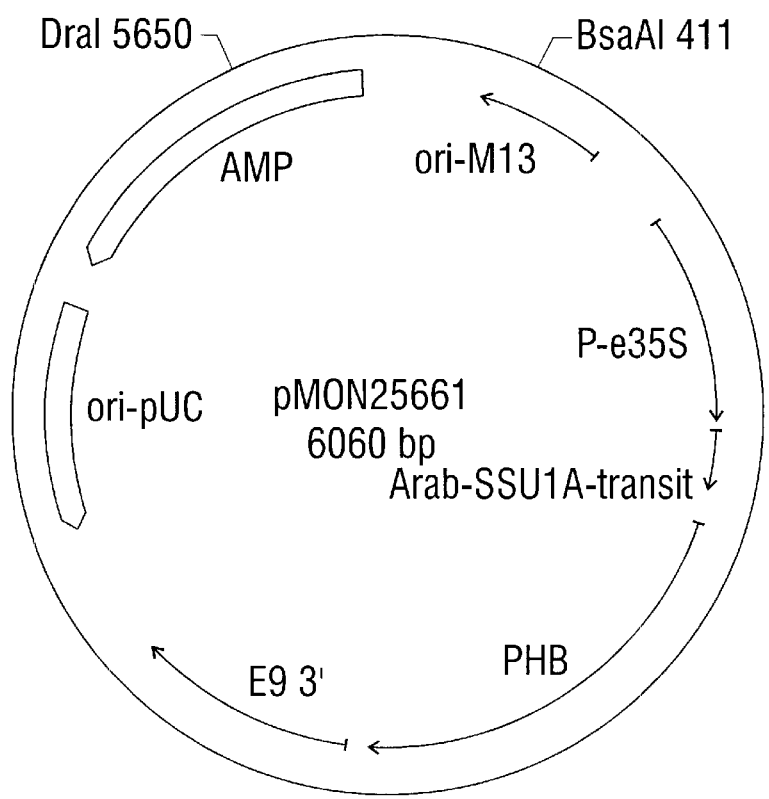
FIG. 6: Plasmid map of pMON25661. A list of the restriction enzyme cutting sites for pMON25661 is provided in Table 13.
Figure 7:
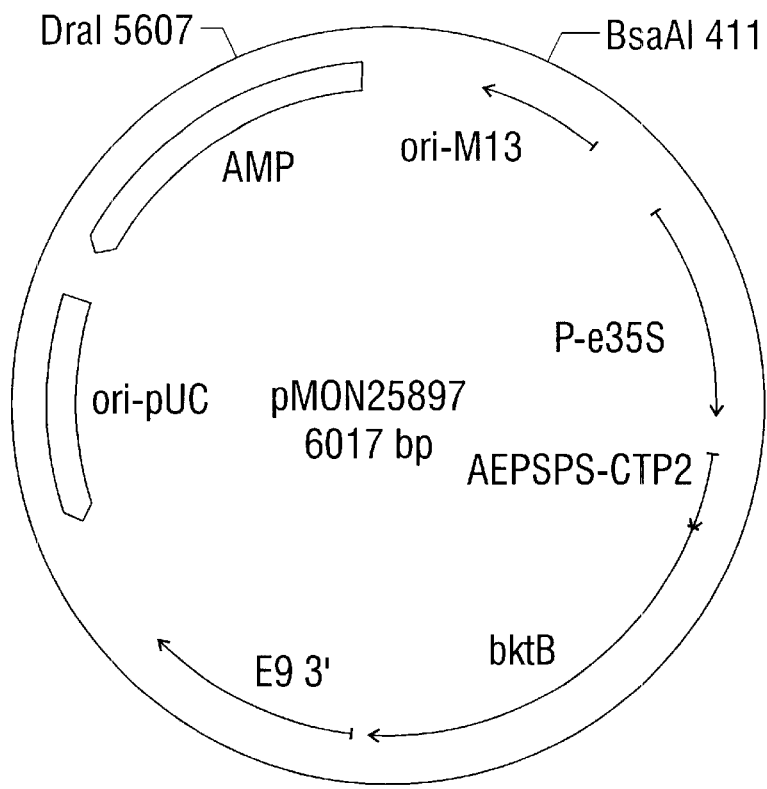
FIG. 7: Plasmid map of pMON25897. A list of the restriction enzyme cutting sites for pMON25897 is provided in Table 14.
Figure 8:
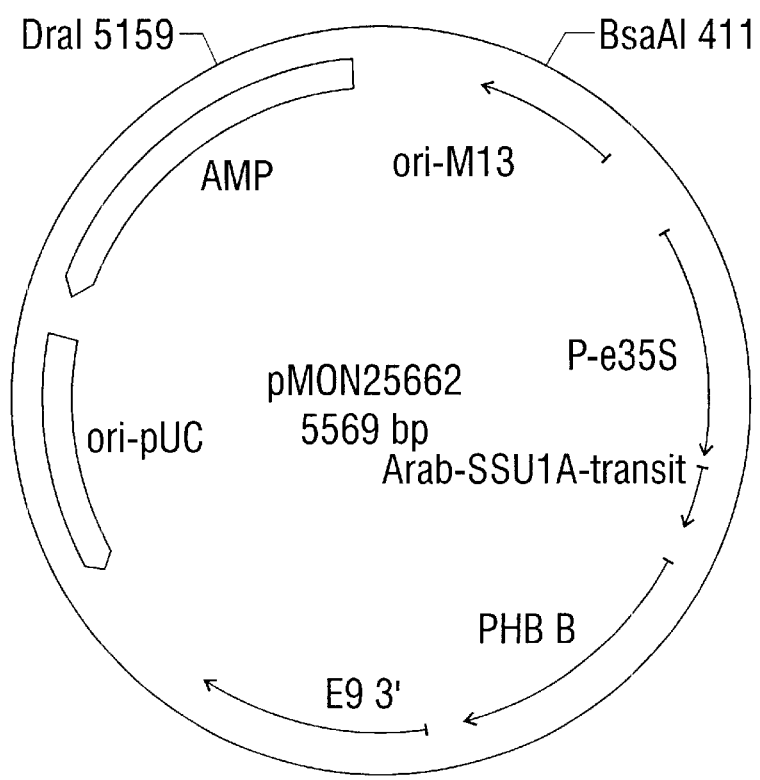
FIG. 8: Plasmid map of pMON25662. A list of the restriction enzyme cutting sites for pMON25662 is provided in Table 15.
Figure 9:
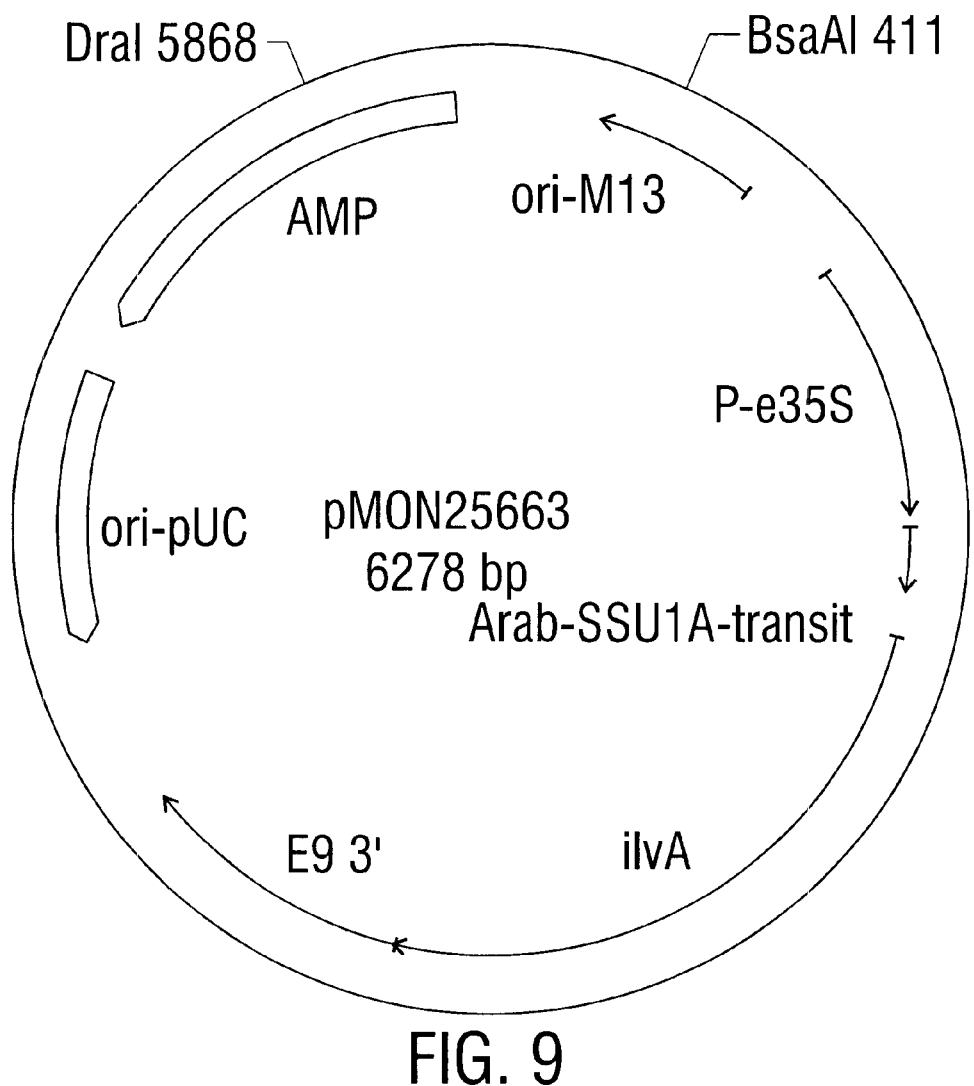
FIG. 9: Plasmid map of pMON25663. A list of the restriction enzyme cutting sites for pMON25663 is provided in Table 16.
Figure 10:
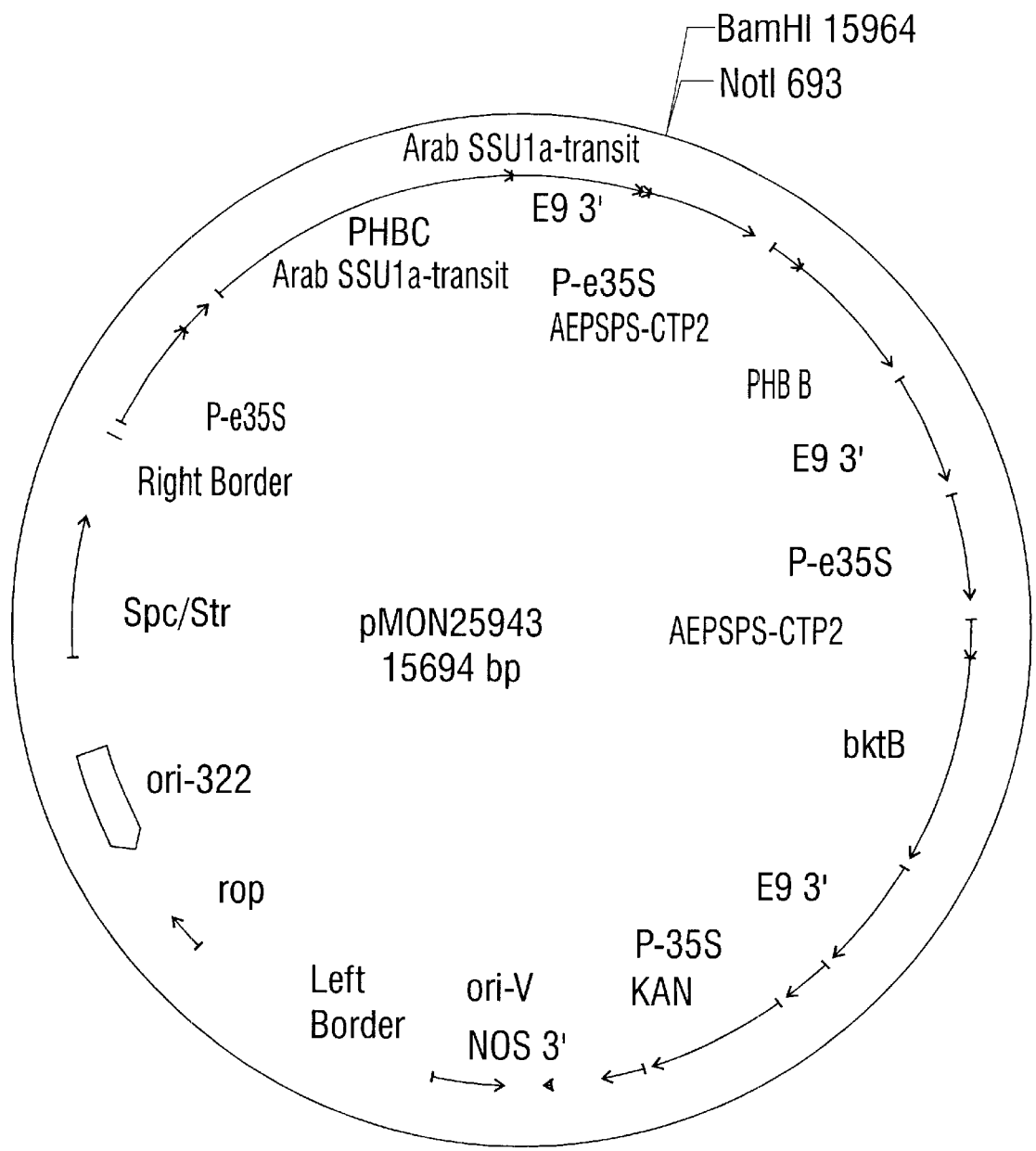
FIG. 10: Plasmid map of pMON25943. A list of the restriction enzyme cutting sites for pMON25943 is provided in Table 17.
Figure 11:
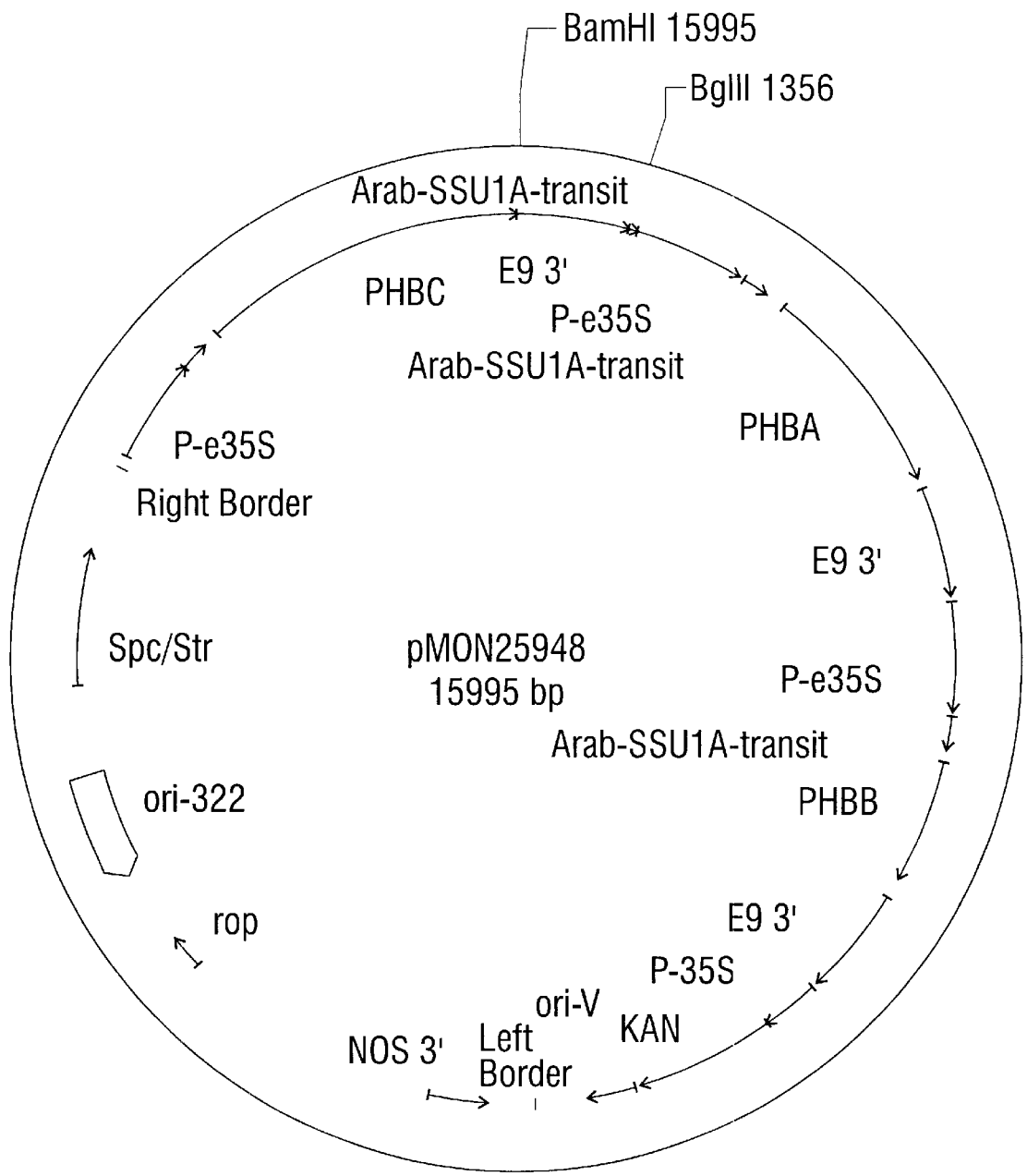
FIG. 11: Plasmid map of pMON25948. A list of the restriction enzyme cutting sites for pMON25948 is provided in Table 18.
Figure 12:
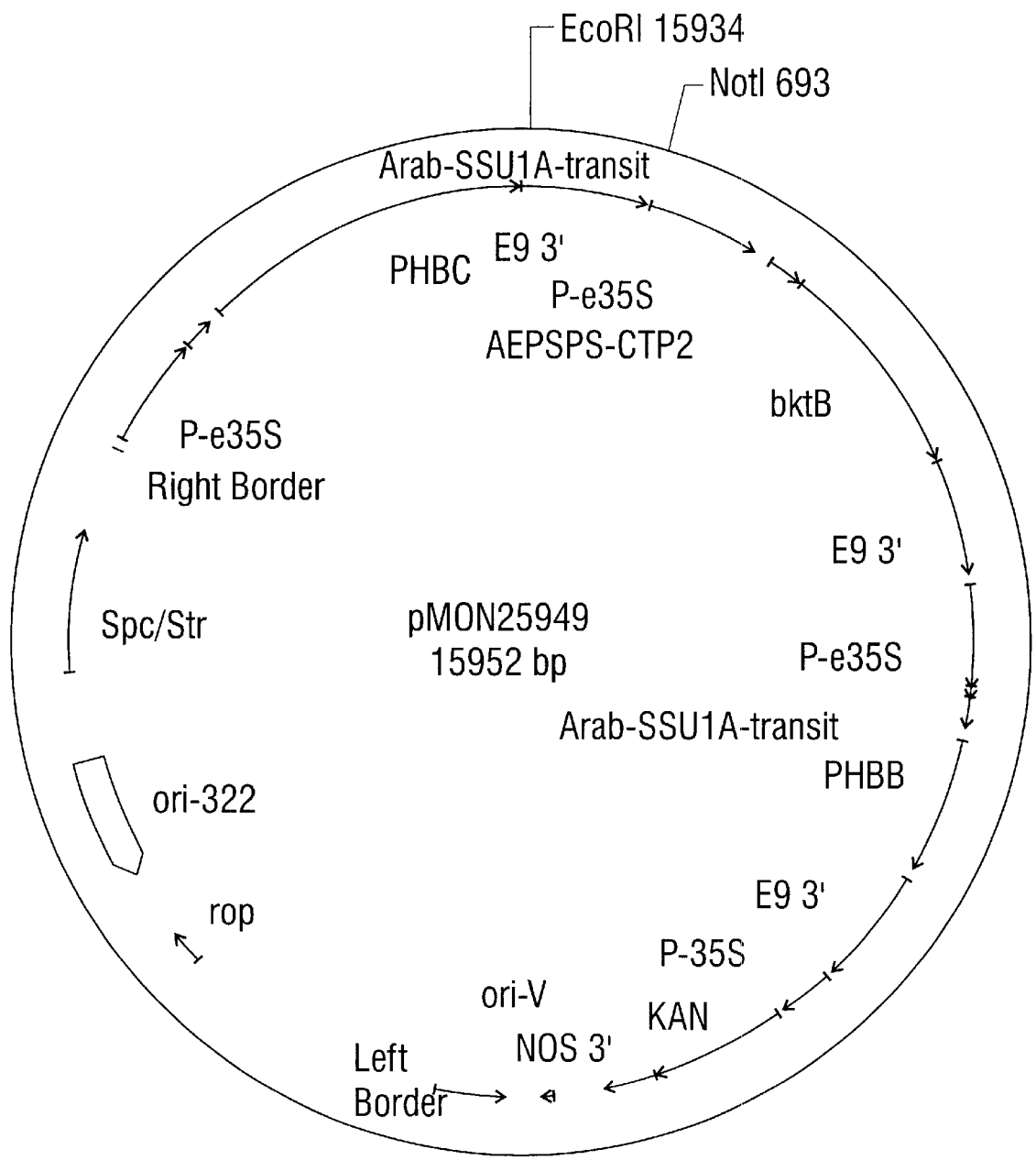
FIG. 12: Plasmid map of pMON25949. A list of the restriction enzyme cutting sites for pMON25949 is provided in Table 19.
Figure 13:
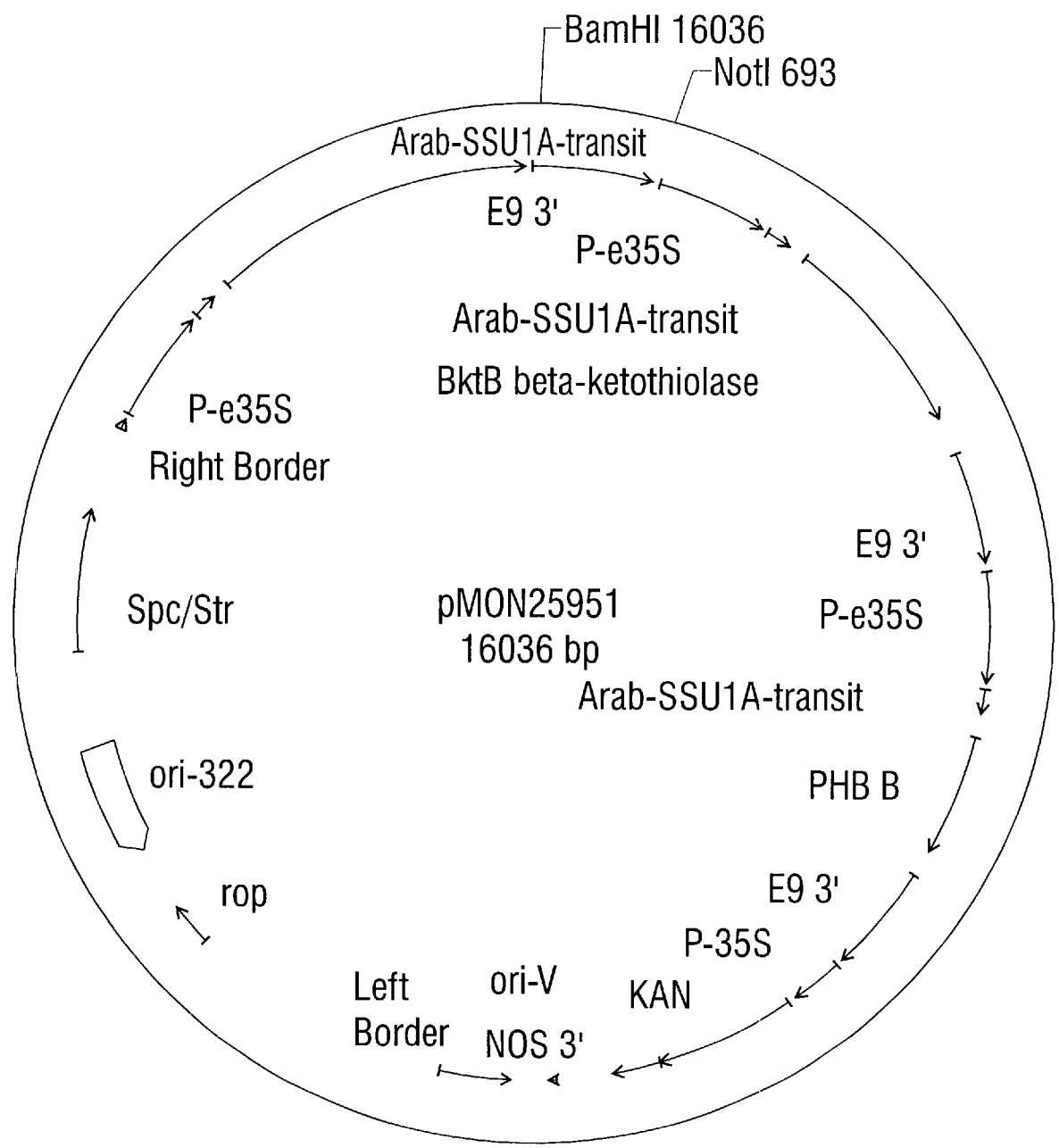
FIG. 13: Plasmid map of pMON25951. A list of the restriction enzyme cutting sites for pMON25951 is provided in Table 20.
Figure 14:
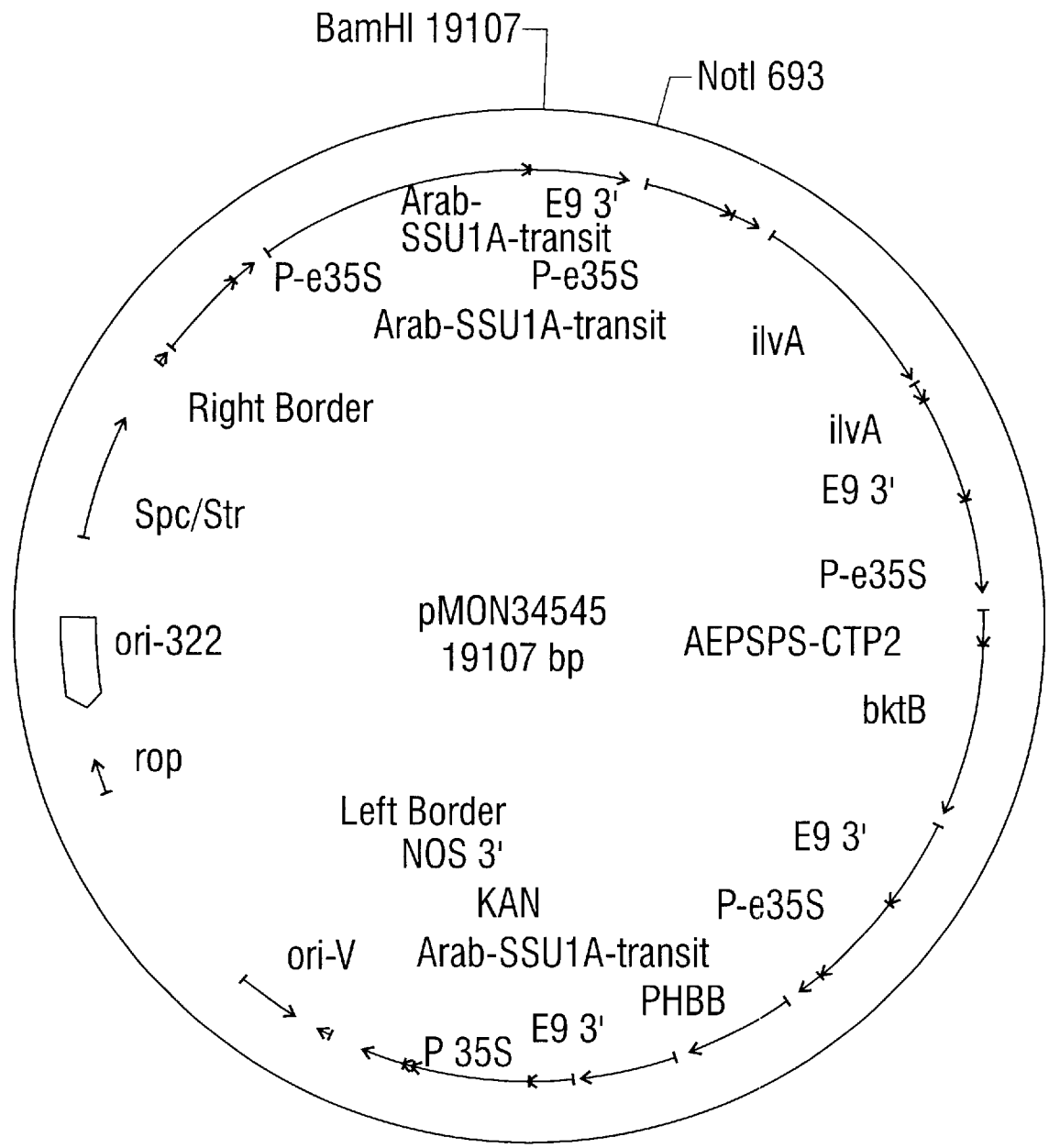
FIG. 14: Plasmid map of pMON34545. A list of the restriction enzyme cutting sites for pMON34545 is provided in Table 21.
Figure 15:
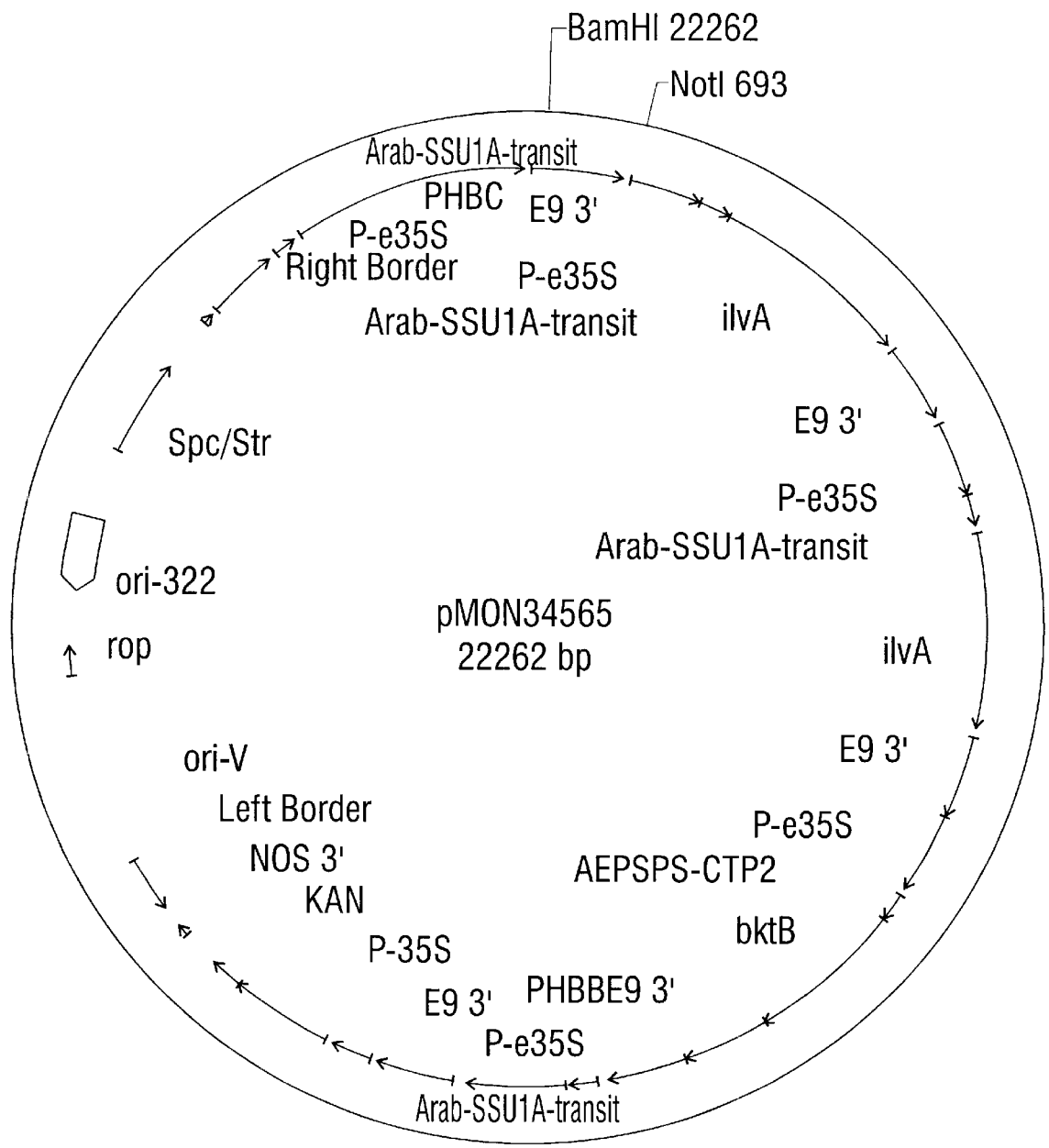
FIG. 15: Plasmid map of pMON34565. A list of the restriction enzyme cutting sites for pMON34565 is provided in Table 22.

Example 4
Construction of Multigene Vectors for Transformation of Arabidopsis In an attempt to increase the speed and simplicity of genetic analysis, multigene vectors were constructed containing the entire PHB biosynthetic pathway on a single plasmid. Multigene vectors for PHA production in Arabidopsis were constructed from a series of base vectors, each with the desired open reading frame under control of the e35s promoter (Odell, J. T., et al, *Nature*, 313: 810–812, 1985) and the E9 3' region (Coruzzi, *EMBO J.* 3:1671–1679, 1984). The first vector in this series, pMON25642 (FIG. 3), harbors phbC under control of the e35s promoter in pMON10098 (FIG. 4), a vector designed for Agrobacterium-mediated transformation of plants. The remaining intermediate vectors are all derived from pMON969 (FIG. 5), a high copy-number vector harboring the e35s promoter and the E9 3' region. Constructs derived from pMON969 include those encoding phbA (pMON25661; FIG. 6), bktB (pMON25897; FIG. 7), phbB (pMON25662; FIG. 8), and ilvA (pMON25663; FIG. 9). From these and similar vectors were derived the final plasmids for transformation of Arabidopsis; pMON25943 (FIG. 10) pMON25948 (FIG. 11), pMON25949 (FIG. 12), pMON25951 (FIG. 13), and pMON34545 (FIG. 14). All cloning procedures were performed using standard ligation techniques (Sambrook, J., et al, "Molecular cloning: A laboratory manual," Cold Spring Harbor Laboratory Press, Cold Spring Harbor, N.Y., 1989), except that ligation of NotI-cut pMON25949 with the ilvA-containing NotI restriction fragment of pMON25663 produced plasmid pMON34565 (FIG. 15), that serendipitously contained two copies of the ilvA fragment. Each copy of ilvA contains a SnaBI restriction site, so deletion of a 3155 bp SnaBI restriction fragment from pMON34565 produced plasmid pMON34545, a plasmid with a single copy of ilvA.

The final vectors, pMON25943, pMON25948, pMON25949, pMON25951, and pMON34545 were used for Agrobacterium-mediated transformation of Arabidopsis (Bechtold N., et al. *Comptes Rendus Acad. Sci. Paris Sciences Serie III Sciences de la Vie.* 316: 94–1199, 1993). This approach has proven successful in generating lines with the highest levels of PHB obtained to date in our laboratory. PHA production in the plants resulting from the first four of these vectors is summarized in Table 4. Data from pMON34545 transformations will be obtained. All of the data in Table 4 were derived from heterozygous plants, and the polymer concentration may increase once the plants are brought to homozygosity. For example, one plant that produced about 7% PHB by dry weight when heterozygous produced polymer up to 13% when homozygous.

TABLE 4

Polymer results from Arabidopsis derived from multigene vectors.

| Vector number | Plant construct description | # of lines assayed | # of lines positive | C4 Polymer (% cell dry wt.) |
|---|---|---|---|---|
| | e35s ctpl phbC | | | 0.11–2.94% |
| 25943 | e35s ctp2 phbB | 34 | 28 | AVE: 1.13% |
| | e35s ctpl bktB | | | SD: 0.65% |
| | e35s ctpl phbC | | | 0.01–7.63% |
| 25948 | e35s ctpl phbA | 53 | 46 | AVE: 2.08% |
| | e35s ctpl phbB | | | SD: 1.56% |
| | e35s ctpl phbC | | | 0.02–7.74% |
| 25949 | e35s ctp2 bktB | 35 | 30 | AVE: 1.82% |
| | e35s ctpl phbB | | | SD: 1.39% |
| | e35s ctpl phbC | | | 0.20–3.78% |
| 25951 | e35s ctpl bktB e35s ctpl phbB | 12 | 11 | AVE: 1.60% SD: 1.04% |

Figure 40:
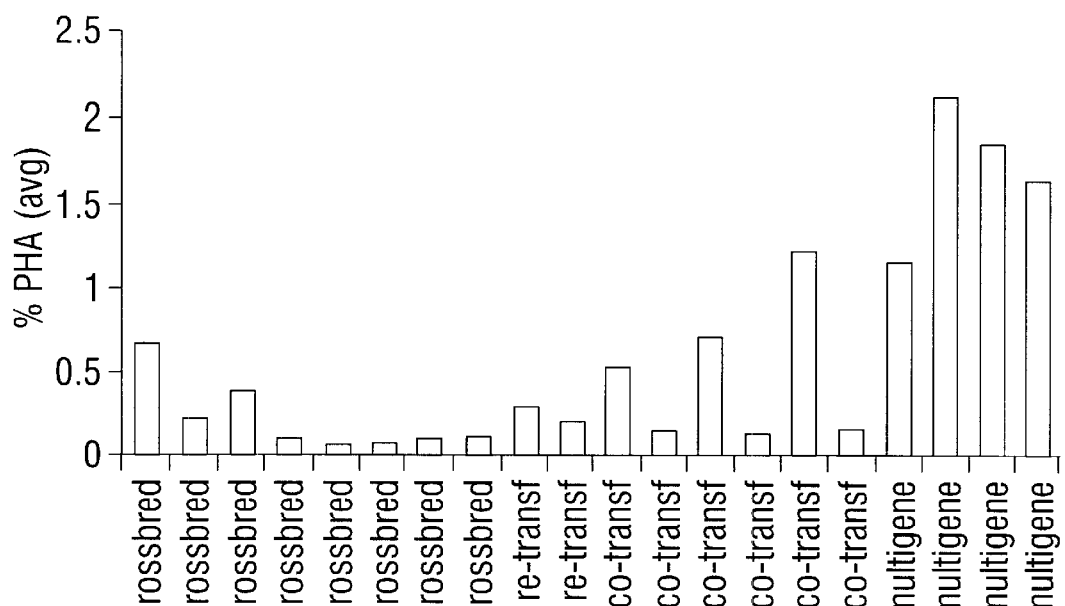
FIG. 40: Bar graph of average % PHA produced from Arabidopsis transformation methods.
Figure 42:
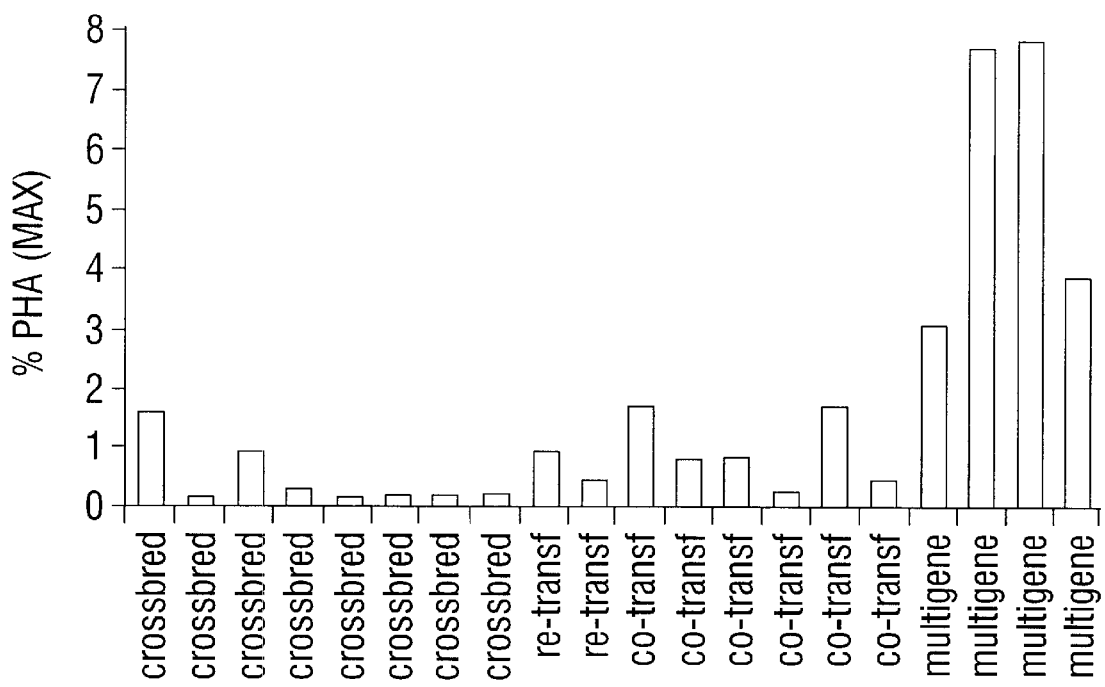
FIG. 42: Bar graph of maximum % PHA produced from Arabidopsis transformation methods.

153/172 plants positive for PHB; 7 had greater than 4% dry weight; AVE = average; SD = standard deviation These results demonstrate that use of a multigene vector provides consistently higher levels of polymer production than were achieved using multiple vectors. The striking beneficial results in polymer production obtained from the use of multigene vectors are visually displayed in FIGS. 40 and 42.

There are several possible explanations for the increased levels of polymer present in the multigene vector transformants. One explanation derives from the fact that it was possible to generate more independent lines with the multigene vectors, and the screening of more plants allowed detection of the relatively rare high-producing lines. This is one clear advantage of having the entire pathway on a single vector, but the distribution of polymer production in plants produced by the various methods suggests that numbers alone do not account for the increased polymer production of multigene vectors. It is also possible that having a metabolic pathway genetically linked at a single integration locus is more metabolically favorable due to some level of concerted gene expression and/or mRNA metabolism. This phenomenon is common in bacteria, but there are not many examples of clustering genes in plants for concerted gene expression. Another possibility is that the high local concentration of promoters may lead to locally high levels of transcription factors. Still another possibility is that having the genes tightly linked may reduce gene silencing, or co-suppression, in certain cases.

Example 5
Extraction of Polymer from Arabidopsis and Analysis of Polymer

For isolation of polymer from Arabidopsis, stems and leaves were harvested and dehydrated by lyophilization for approximately 36 hours. The material was ground to a fine powder, and 100 mg of powder was treated with 10 mL CLOROX bleach (CLOROX is a registered trademark of The Clorox Company, Oakland, Calif.) for 1 hour with shaking at room temperature. The extract was subjected to centrifugation at 2700×g for 10 minutes at 4° C., and the supernatant solutions was carefully removed. Ten mL 100% methanol were added, the solution was mixed by vortexing, and then centrifuged again. After a second, identical methanol extraction, the material was allowed to dry overnight. Polymer was extracted from the dried material with 1 mL of chloroform containing 1 μmol/mL methyl-benzoate standard. The tube was heated to 100° C. for 2.5 hours, solid material was removed by centrifugation, and the supernatant material was subjected to methanolysis. Methanolysis of polymer and gas chromatographic characterization of the methyl-ester residues were performed as described by Slater et al. (*J. Bacteriol.* 180:1979–1987, 1998).

Example 6
Use of Multiple Vectors for Gene Expression in the Seeds of Canola

Production of polyhydroxyalkanoate has also been accomplished within the seed of canola (oil seed rape). Initial efforts followed essentially the same strategy as the initial Arabidopsis strategy. That is, one vector carried the sequences encoding acetoacetyl-CoA reductase and PHA synthase proteins, while another carried the sequence encoding a β-ketothiolase protein. However the 7s promoter, which is expressed primarily in the seed, replaced the 35s promoter that was used in the Arabidopsis constructs. These 7s promoter vectors were used to transform oilseed rape, homozygous lines were crossed, and PHB accumulation was assayed in the resulting lines (Table 5). A number of lines that produce PHB were identified, but all produced relatively low concentrations of polymer, with the best lines containing about 2% polymer by dry weight.

TABLE 5

Polymer results for canola crosses.

| Vector number | Plant construct description | # of plants assayed | # of plants positive | C4 polymer (% dry wt.) |
|---|---|---|---|---|
| 25638 | 7s ctpl phbA | | | 0.024–1.99% |
| 25626 | 7s ctpl phbC<br>7s ctpl phbB | 42 | 37 | 0.58%<br>SD: 0.59% |
| 25638 | 7s ctpl phbA | | | 0.039–0.053 |
| 25741 | 7s tpss phbC<br>7s tpss phbB | 12 | 2 | 0.05%<br>SD: 0.01% |
| 25818 | 7s ctpl bktB<br>7s ctpl ilvA wt. | 22 | 17 | 0.04–1.67%<br>AVE: 0.61% |
| 25626 | 7s ctpl phbC<br>7s ctpl phbB | | | SD: 0.43% |
| 25818 | 7s ctpl bktB<br>7s ctpl ilvA w.t. | 15 | 0 | NA |
| 25741 | 7s tpss phbC<br>7s tpss phbB | | | |
| 25820 | 7s ctpl bktB<br>7s ctpl ilvA466 | 19 | 12 | 0.26–0.72%<br>AVE: 0.51% |
| 25626 | 7s ctpl phbC<br>7s ctpl phbB | | | SD: 0.16% |
| 25820 | 7s ctpl bktB<br>7s ctpl ilvA466 | 7 | 0 | NA |
| 25741 | 7s tpss phbC<br>7s tpss phbB | | | |

Example 7
Construction of Multigene Vectors for Transformation of Canola

Figure 16:
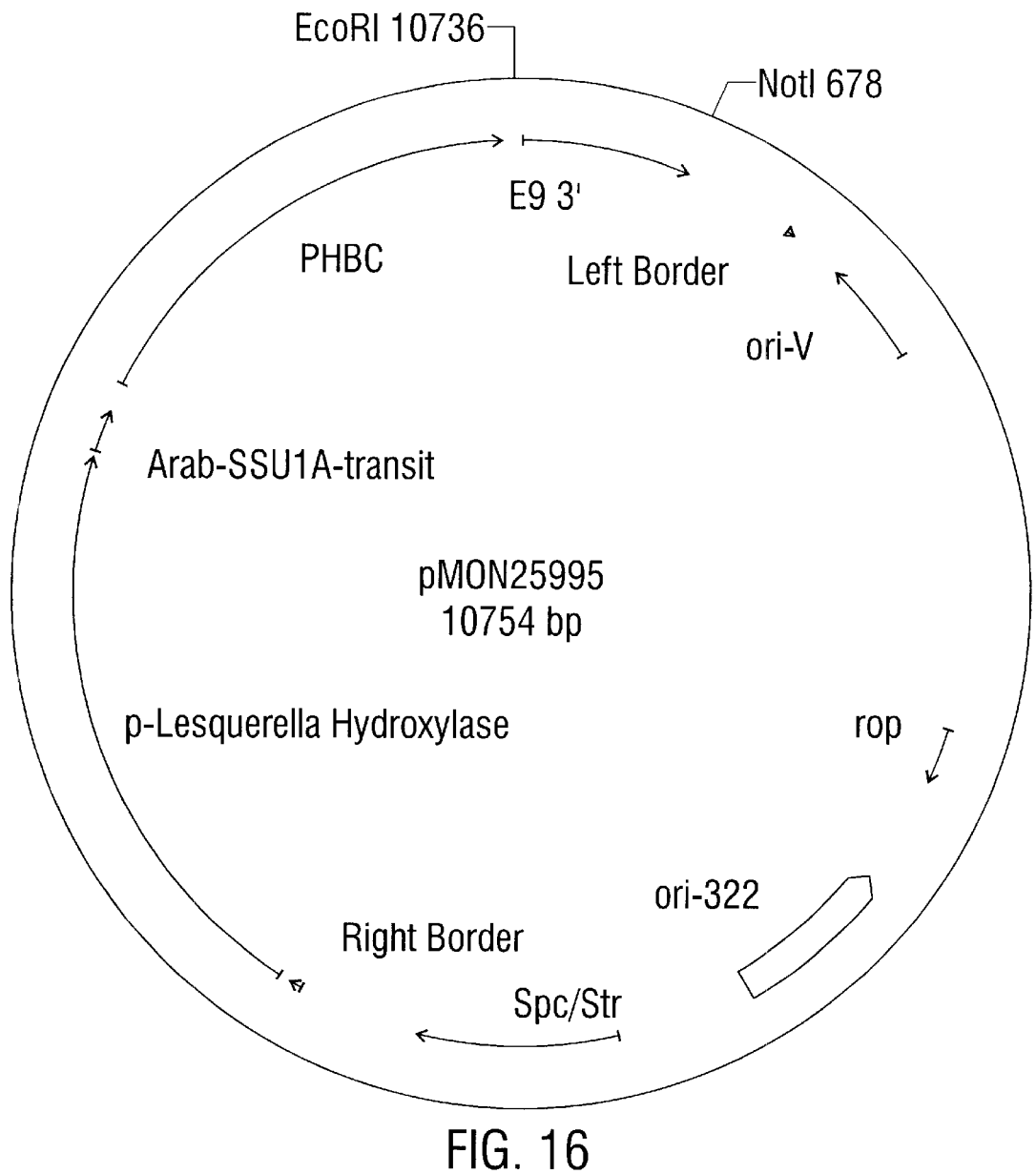
FIG. 16: Plasmid map of pMON25995. A list of the restriction enzyme cutting sites for pMON25995 is provided in Table 23.
Figure 17:
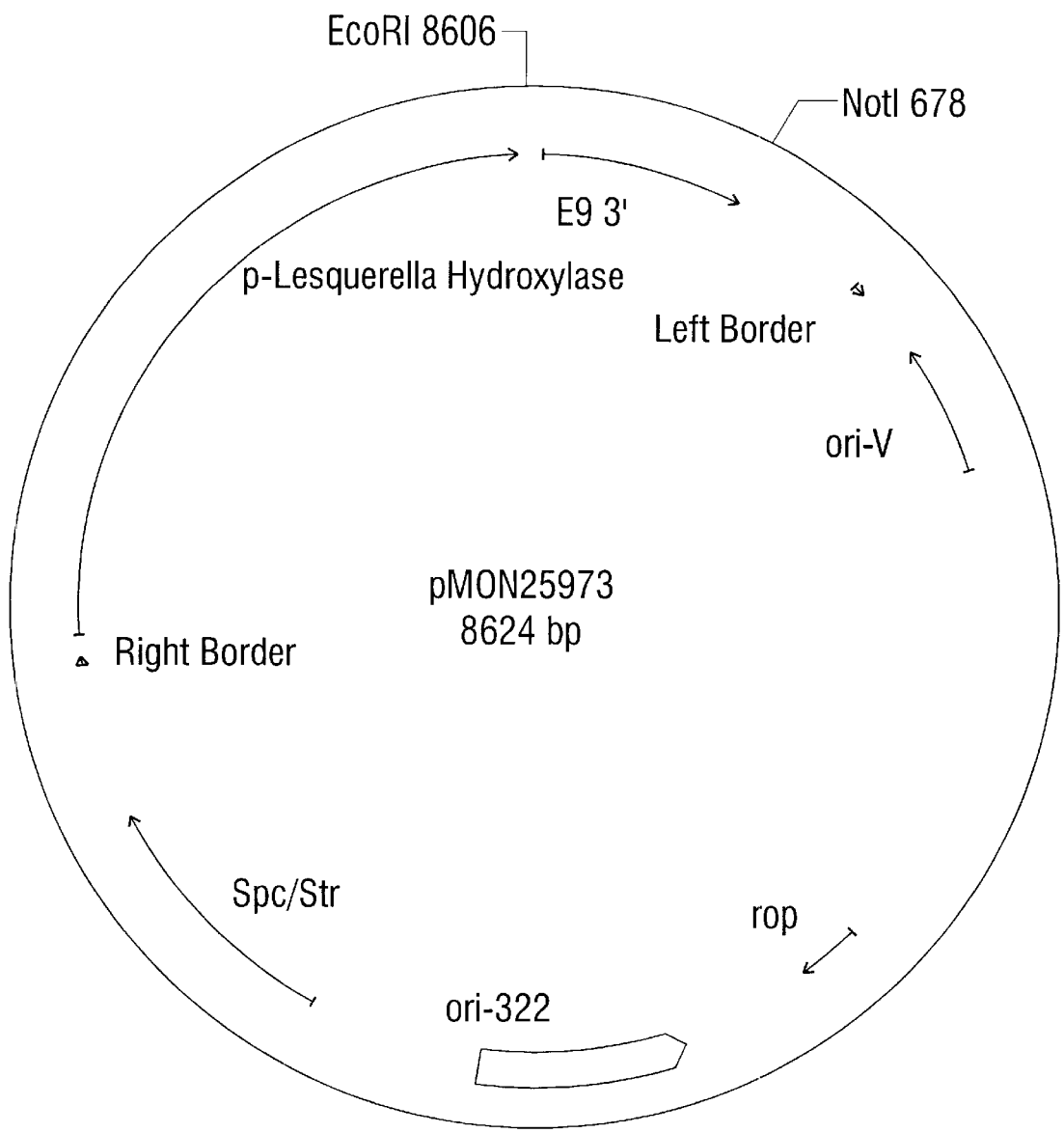
FIG. 17: Plasmid map of pMON25973. A list of the restriction enzyme cutting sites for pMON25973 is provided in Table 24.
Figure 18:
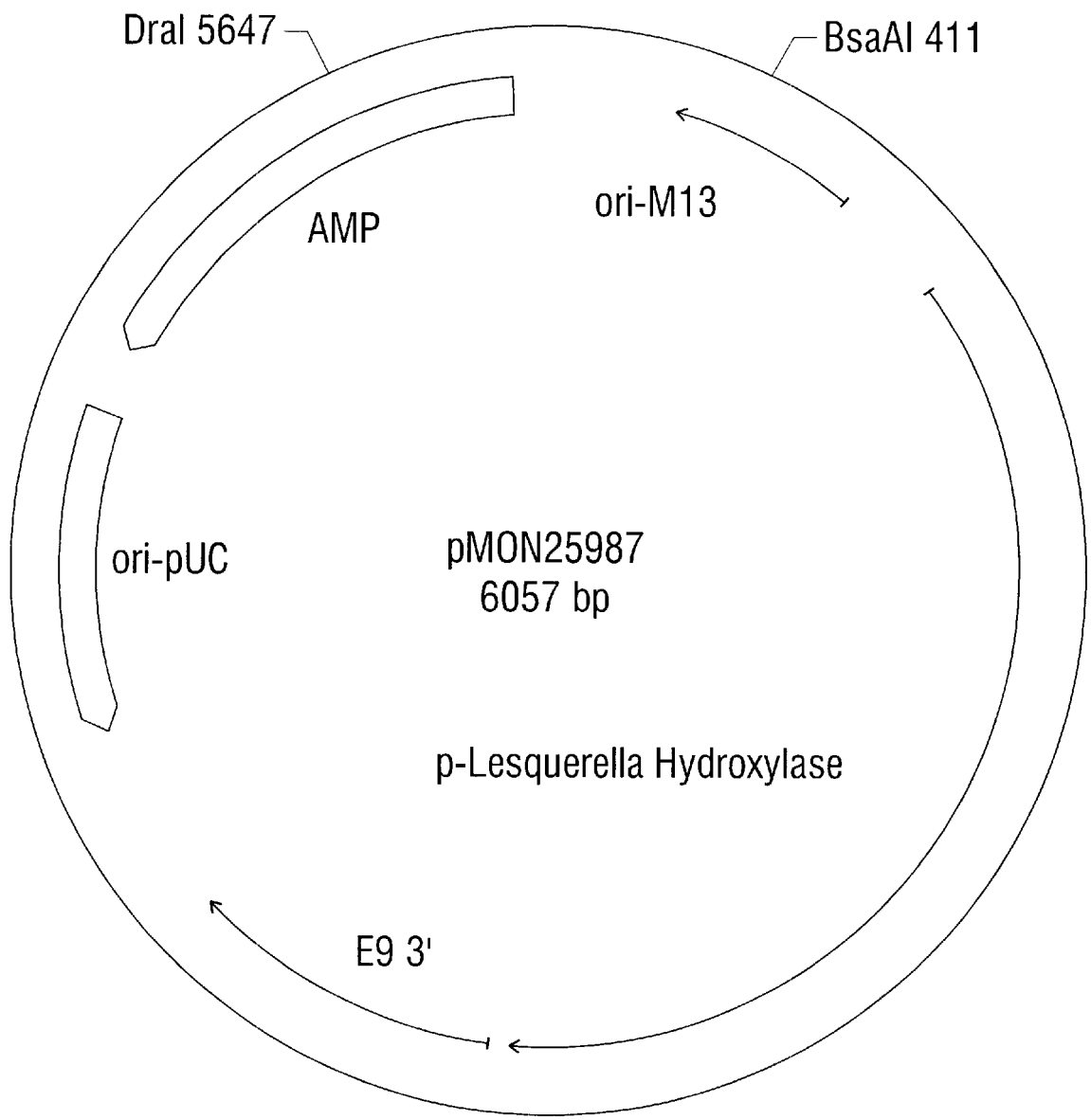
FIG. 18: Plasmid map of pMON25987. A list of the restriction enzyme cutting sites for pMON25987 is provided in Table 25.
Figure 19:
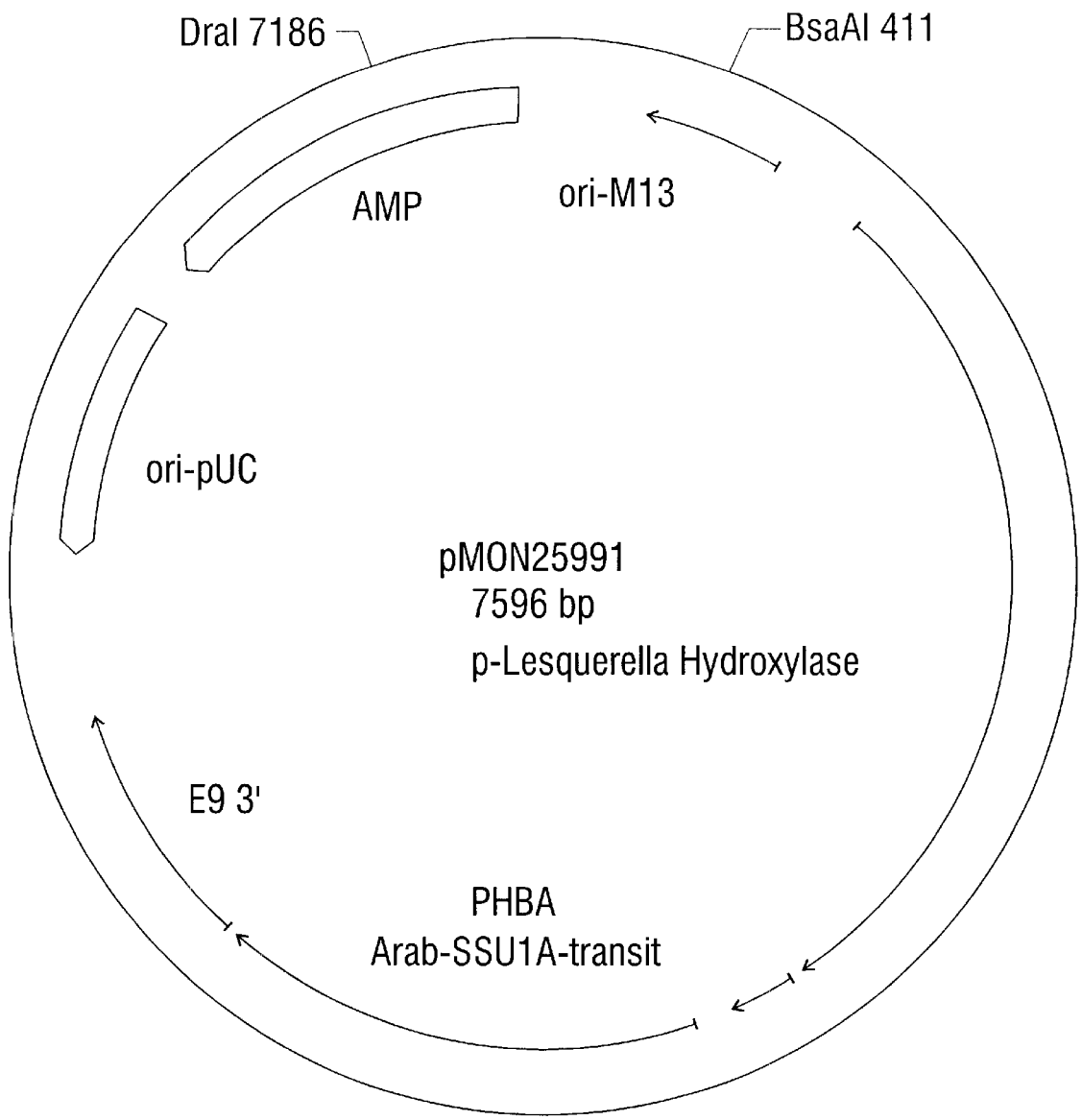
FIG. 19: Plasmid map of pMON25991. A list of the restriction enzyme cutting sites for pMON25991 is provided in Table 26.
Figure 20:
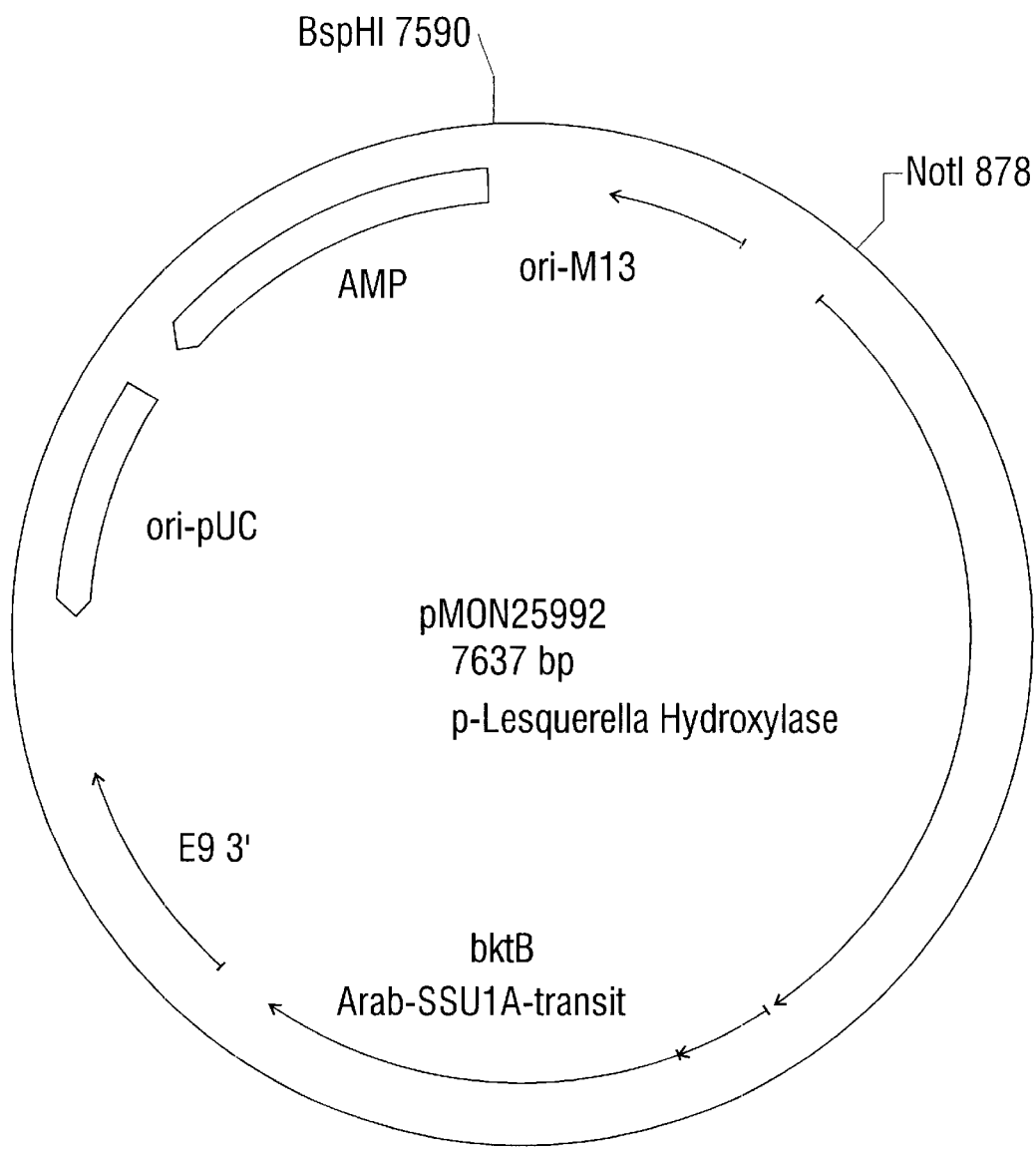
FIG. 20: Plasmid map of pMON25992. A list of the restriction enzyme cutting sites for pMON25992 is provided in Table 27.
Figure 21:
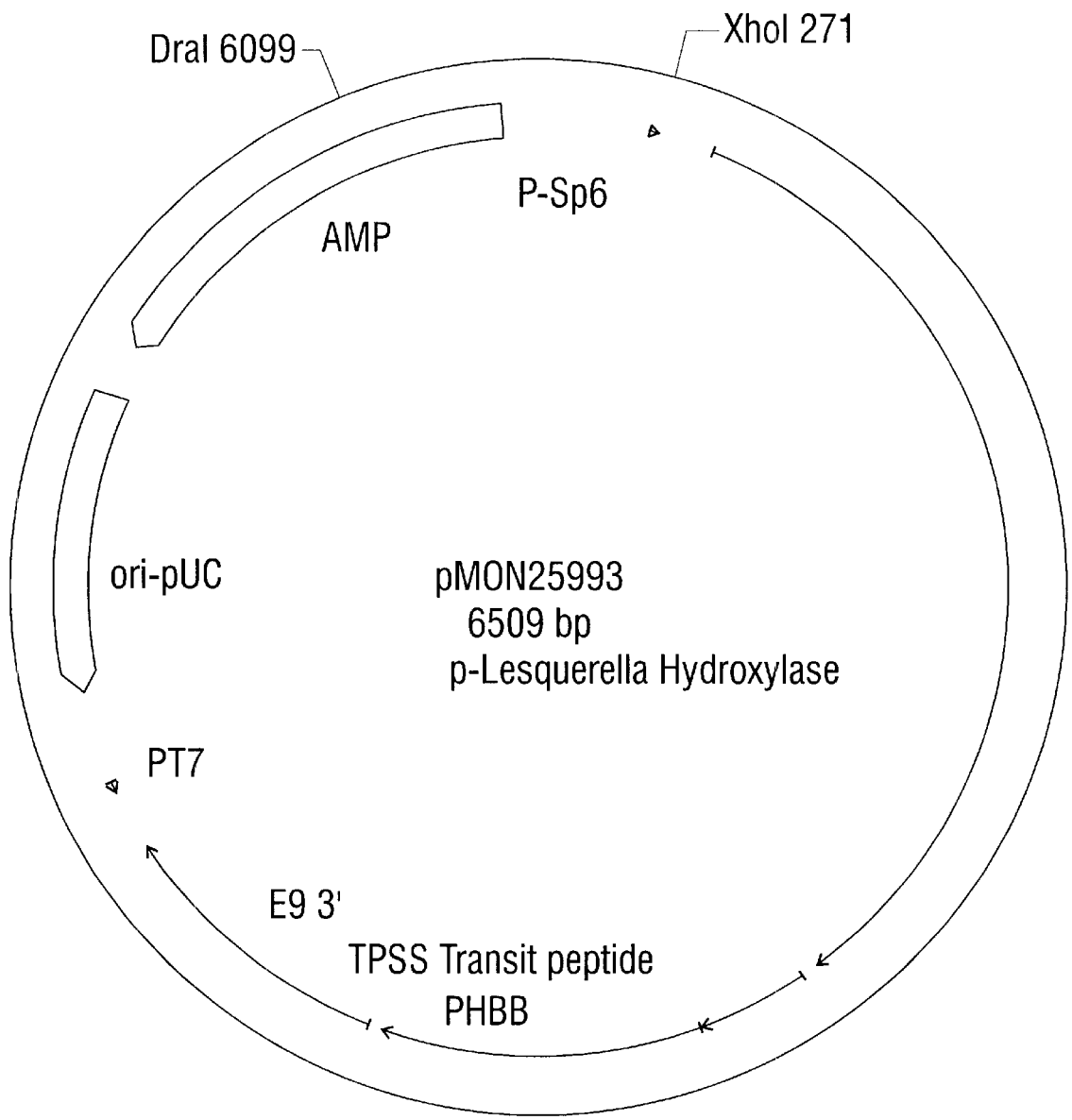
FIG. 21: Plasmid map of pMON25993. A list of the restriction enzyme cutting sites for pMON25993 is provided in Table 28.
Figure 22:
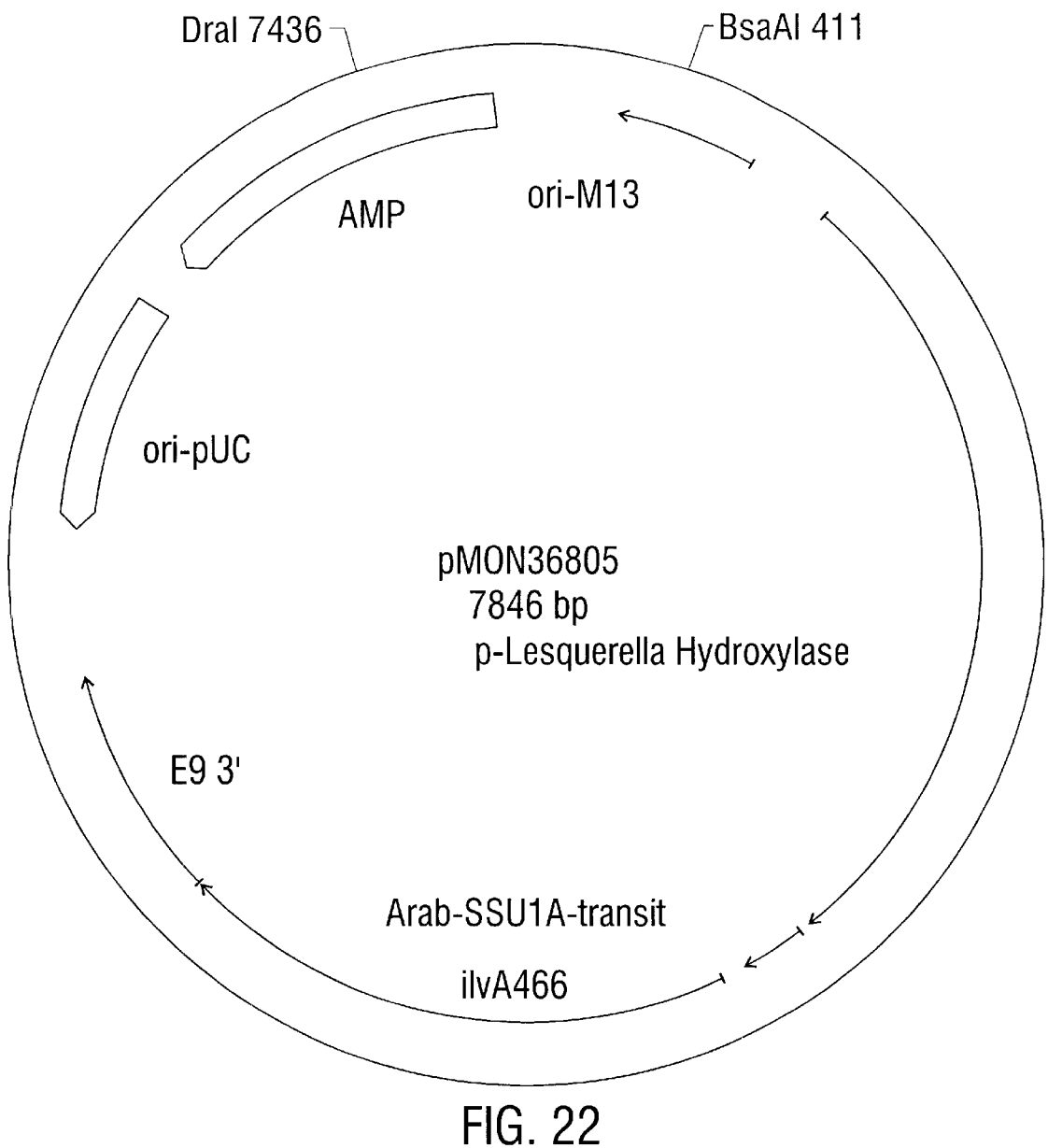
FIG. 22: Plasmid map of pMON36805. A list of the restriction enzyme cutting sites for pMON36805 is provided in Table 29.
Figure 23:
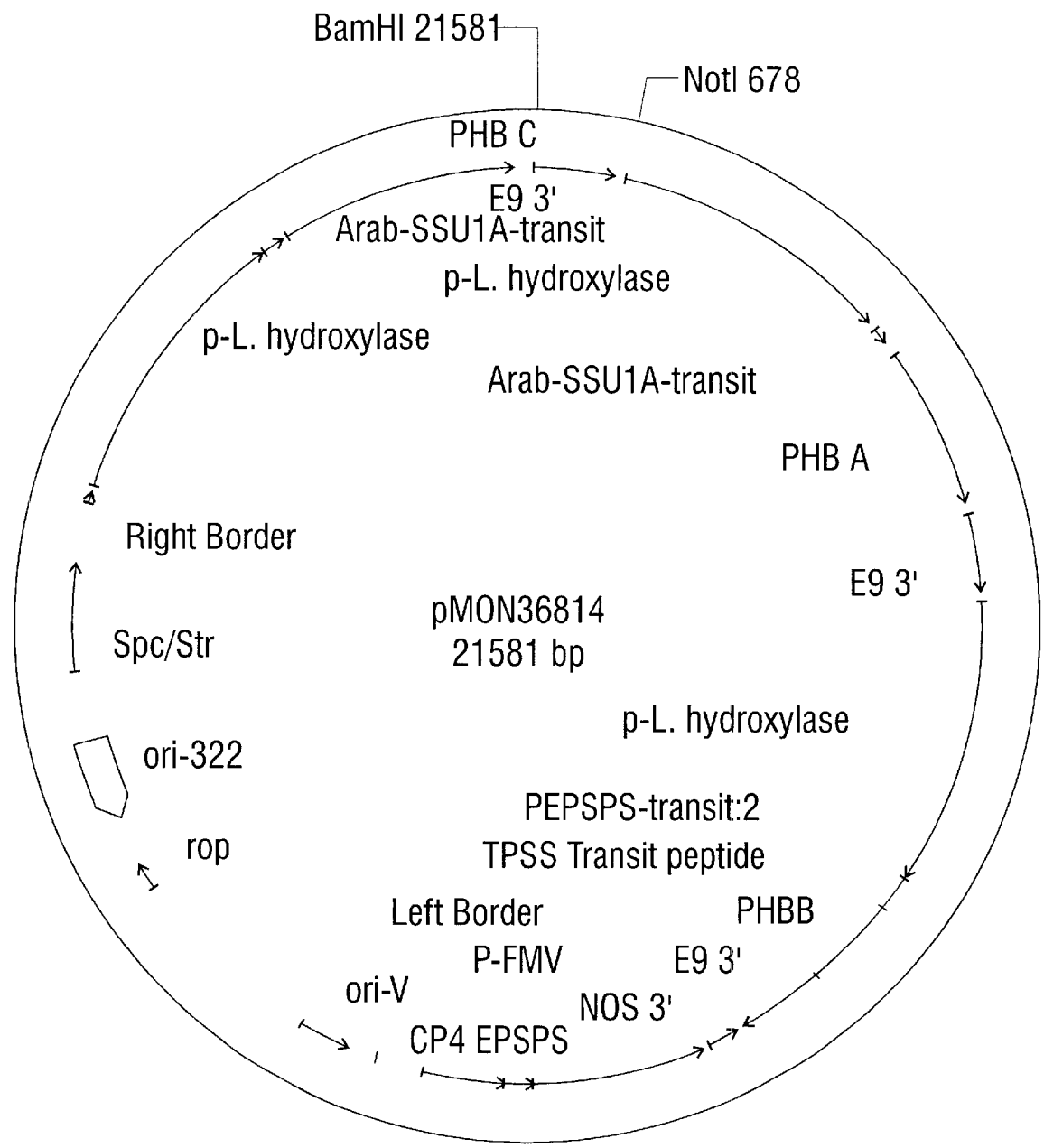
FIG. 23: Plasmid map of pMON36814. A list of the restriction enzyme cutting sites for pMON36814 is provided in Table 30.
Figure 24:
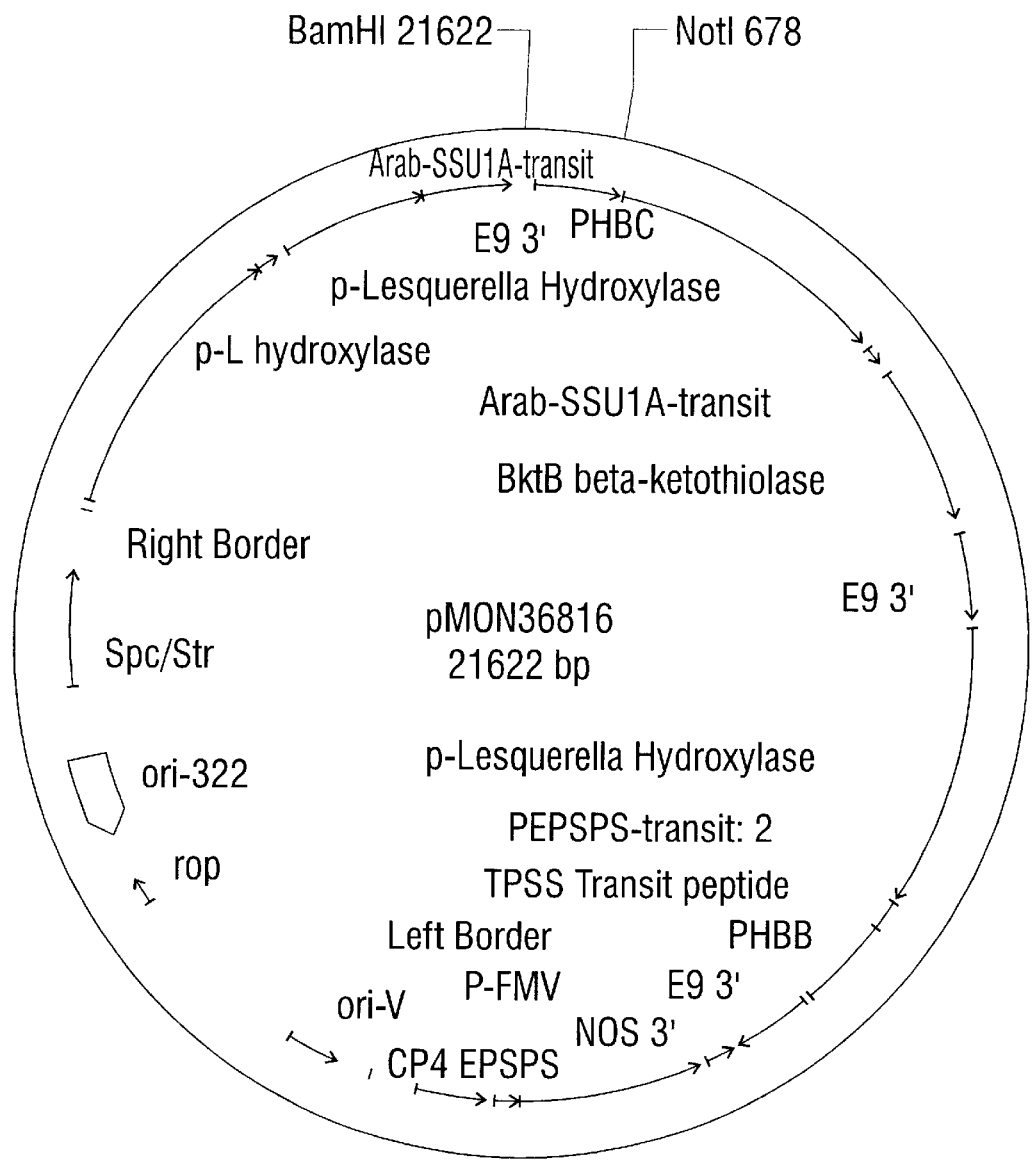
FIG. 24: Plasmid map of pMON36816. A list of the restriction enzyme cutting sites for pMON36816 is provided in Table 31.
Figure 25:
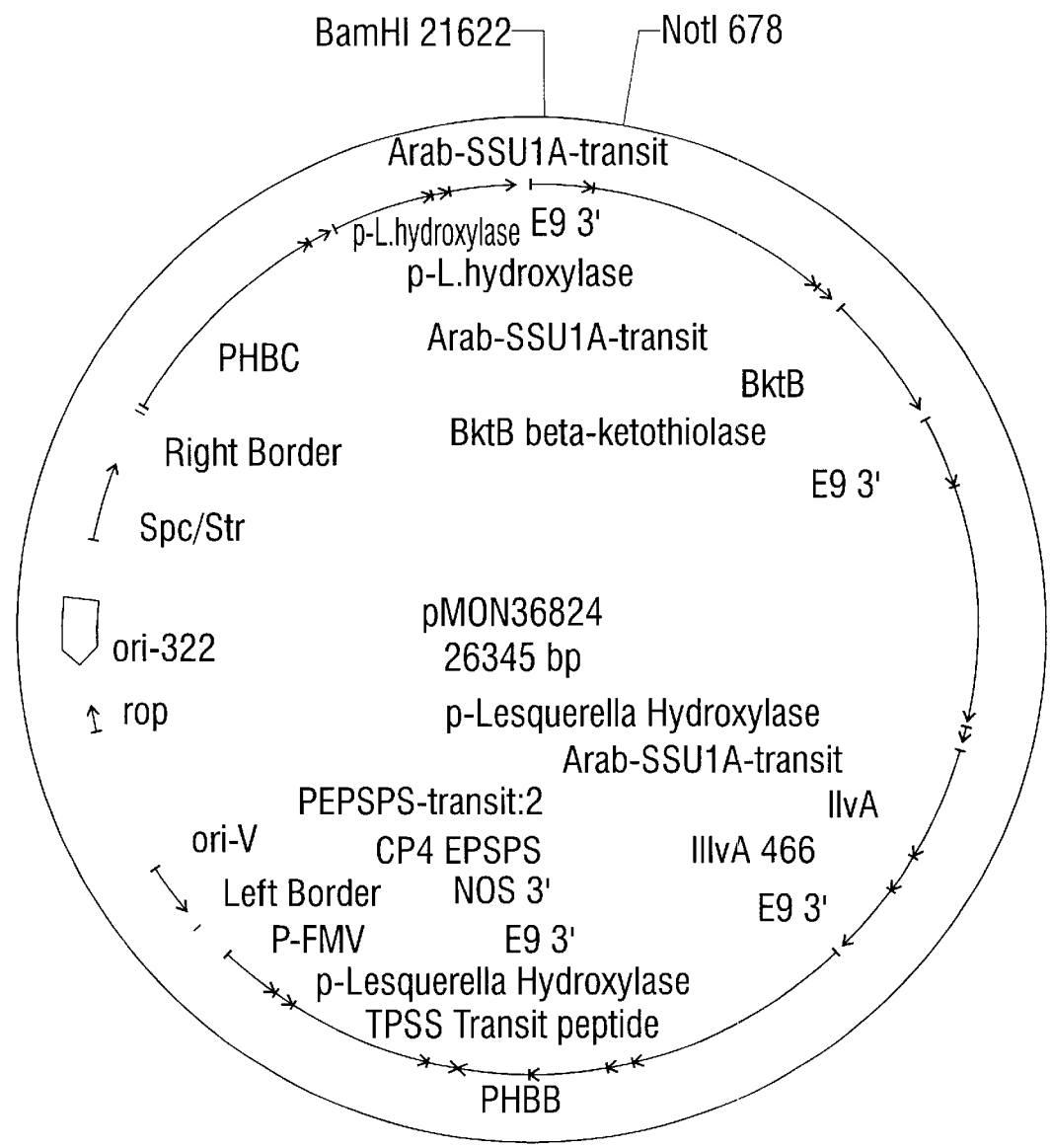
FIG. 25: Plasmid map of pMON36824. A list of the restriction enzyme cutting sites for pMON36824 is provided in Table 32.

Large vectors for expression of multiple genes have also been used to produce polyhydroxyalkanoate in the seeds of canola (oil seed rape). In this case, the promoter was derived from the fatty acid hydroxylase gene of Lesquerella (P-lh) (Broun, P. and C. Somerville. *Plant Physiol.* 113: 933–942, 1997), which is expressed primarily within the developing seed. A series of vectors, each expressing the entire PHA biosynthesis pathway, was used for transformation of oilseed rape. The multigene vectors were constructed from a series of base vectors, each with the desired open reading frame under control of the Lesquerella hydroxylase promoter (P-lh; Broun, P. and Somerville, C. R. *Plant Physiol.*, 113: 933–942,1987) and the E9 3' region. The first vector in this series, pMON25995 (FIG. 16), harbors phbC under control of P-lh in pMON25973 (FIG. 17), a vector designed for Agrobacterium-mediated transformation of plants. The remaining intermediate vectors are all derived from pMON25987 (FIG. 18), a high copy-number vector harboring P-lh and the E9 3' region. Constructs derived from pMON25987 (FIG. 16) include those encoding phbA (pMON25991; FIG. 19), bktB (pMON25992; FIG. 20), phbB (pMON25993; FIG. 21), and ilvA (pMON36805; FIG. 22). These intermediate vectors were used to construct the final vectors for oilseed rape transformation; pMON36814 (FIG. 23), pMON36816 (FIG. 24), and pMON36824 (FIG. 25).

Construction of the multigene vectors for oilseed rape was not as straightforward as was the construction of the Arabidopsis vectors. This was primarily due to the large size of the promoter (P-lh is about 2.2 kb), and the resulting larger size of the multigene vector intermediates. As the vectors increased in size, it was found to be most efficient to perform ligations of two similar sized fragments, rather than one large vector and one small incoming fragment. In addition, it was desirable to avoid partial digests of the large vectors, and to perform cloning in which opposite ends of an individual fragment were not compatible. A number of intermediate vectors were constructed specifically to allow cloning in this manner. Another advantage of this approach is that it often allowed restriction enzyme-mediated digestion of the parental plasmids prior to transformation of *Escherichia coli* with ligation products. This procedure significantly increased the frequency of correct constructs recovered. The final vectors were used for Agrobacterium-mediated transformation of oilseed rape (Fry, J. et al., *Plant Cell Rep.* 6: 321–325, 1987).

The results of oilseed rape transformation with the multigene vectors are shown in Table 6. There are two primary points of interest in these data. First, multigene vectors larger than 26 kb were successfully constructed and used to transform oilseed rape, with a very low percentage of the plants failing to produce polymer. Second, the distribution of polymer concentrations among multigene vector transformants is higher than that of the plants derived from two separate 7s vectors.

TABLE 6

Polymer results from canola transformed with multigene vectors.

| Vector number | Plant construct description | # of plants assayed | # of plants positive | C4 polymer (% dry wt.) |
|---|---|---|---|---|
| 36814 | lhydrox ctpl phbC<br>lhydrox ctpl phbA<br>lhydrox tpss phbB | 68 | 59 | 0.19–4.11%<br>AVE: 1.43%<br>SD: 1.01% |
| 36816 | lhydrox ctpl phbC<br>lhydrox ctpl bktB<br>lhydrox tpss phbB | 225 | 195 | 0.02–6.28%<br>AVE: 1.0%<br>SD: 1.02% |
| 36824 | lhydrox ctpl phbC<br>lhydrox ctpl bktB<br>lhydrox tpss phbB<br>lhydrox ctpl ilvA | 185 | 152 | 0.10–2.74%<br>AVE: 0.6%<br>SD: 0.5% |

Figure 41:
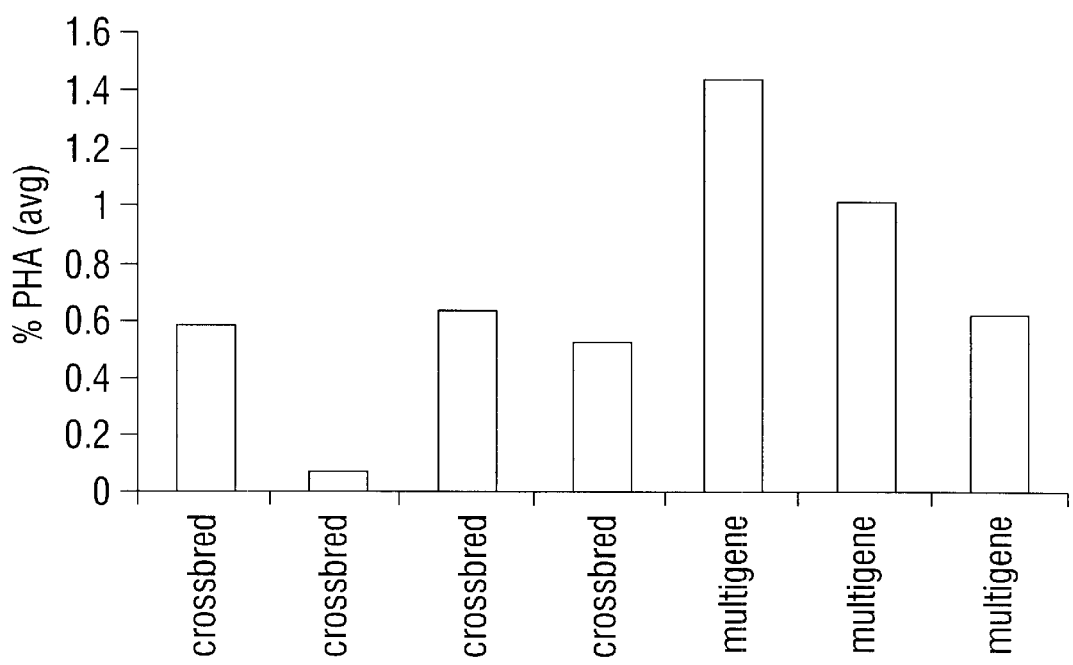
FIG. 41: Bar graph of average % PHA produced from canola transformation methods.
Figure 43:
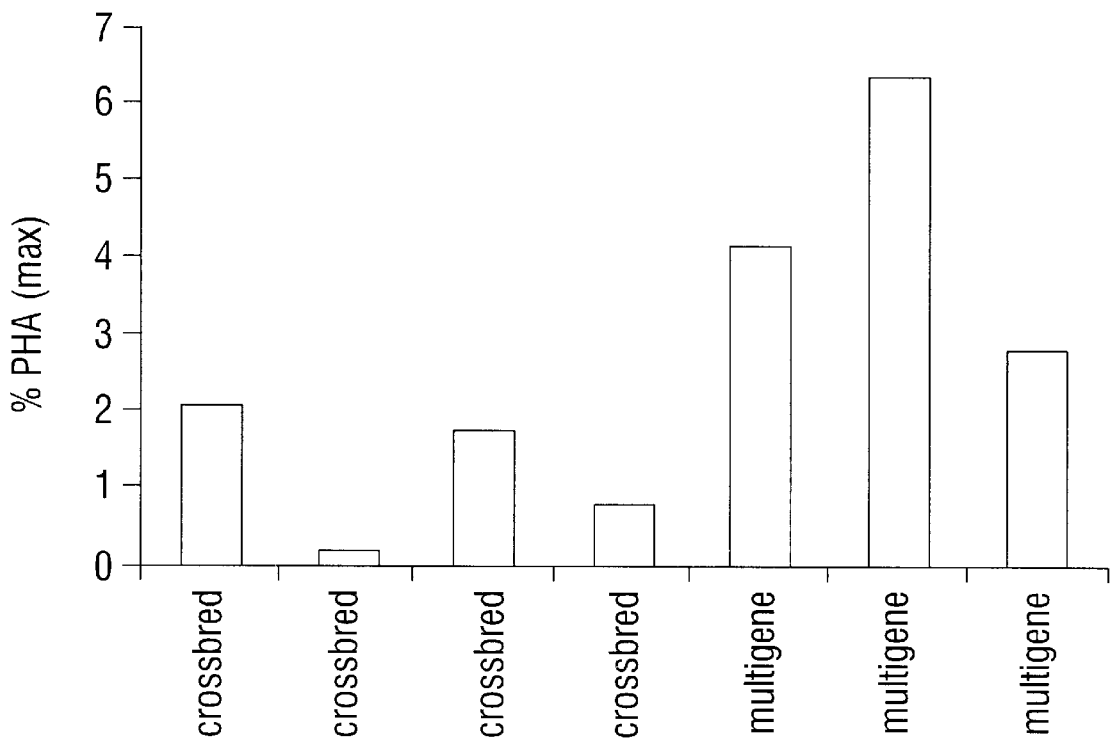
FIG. 43: Bar graph of maximum % PHA produced from canola transformation methods.

The comparative results for PHA production in canola are graphically presented in FIGS. 41 and 43. The beneficial results obtained from the use of multigene vectors compared to results obtained from traditional methods is visually impressive.

Since the promoters used in these two vectors sets (those containing the 7s promoter and those containing the Lesquerella hydroxylase promoter) are different, it cannot be distinguished whether it was the Lesquerella promoter or the use of a single vector that led to the increased polymer concentration. However, it is clear that the single vector approach is viable for seed expression of enzymes, including those required for PHA biosynthesis. In addition, the increased speed of plant construction and analysis using a single vector is a clear benefit.

Example 8
Extraction of Polymer from Oilseed Rape and Analysis of Polymer

For isolation of polymer from canola seed, seeds were ground to a fine powder with a mortar and pestle. Approximately 200 mg of each sample were extracted two times with 10 mL each of hexane for 1 hour at 60° C., then two times with 10 mL each of 100% methanol for one hour at 60° C. This procedure removed oil from the seed. The material was allowed to dry completely overnight. Polymer was extracted from the dried material with 1 mL of chloroform containing 1 μmol/mL methylbenzoate standard. The tube was heated to 100° C. for 5 hours, solid material was removed by centrifugation, and the supernatant material was subjected to methanolysis. Methanolysis of polymer and gas chromatographic characterization of the methyl-ester residues were performed as described by Slater et al. (*J. Bacteriol.* 180: 1979–1987, 1998).

Example 9
Multigene Vectors for Gene Expression in Monocots

Figure 26:
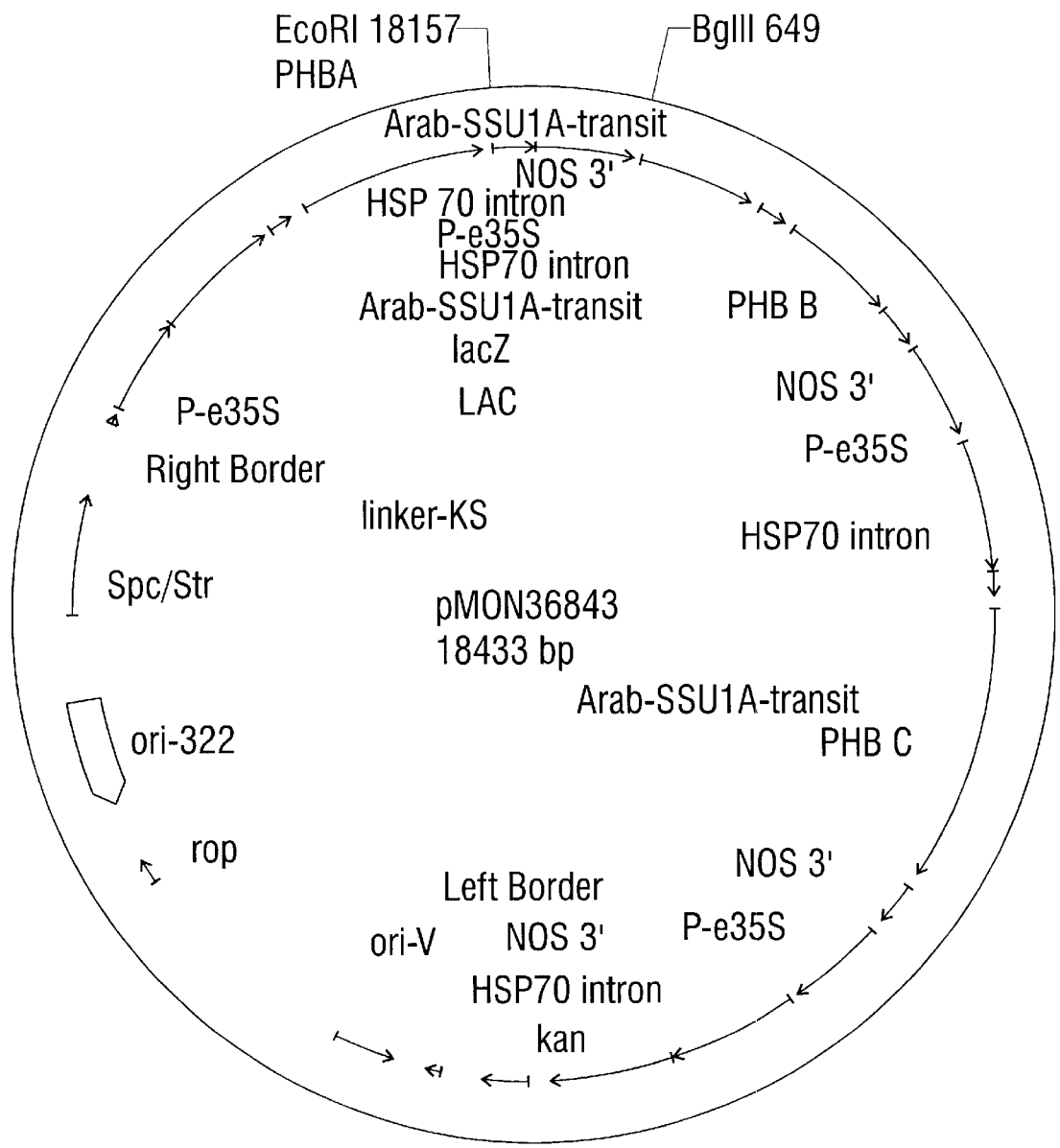
FIG. 26: Plasmid map of pMON36843. A list of the restriction enzyme cutting sites for pMON36843 is provided in Table 33.
Figure 27:
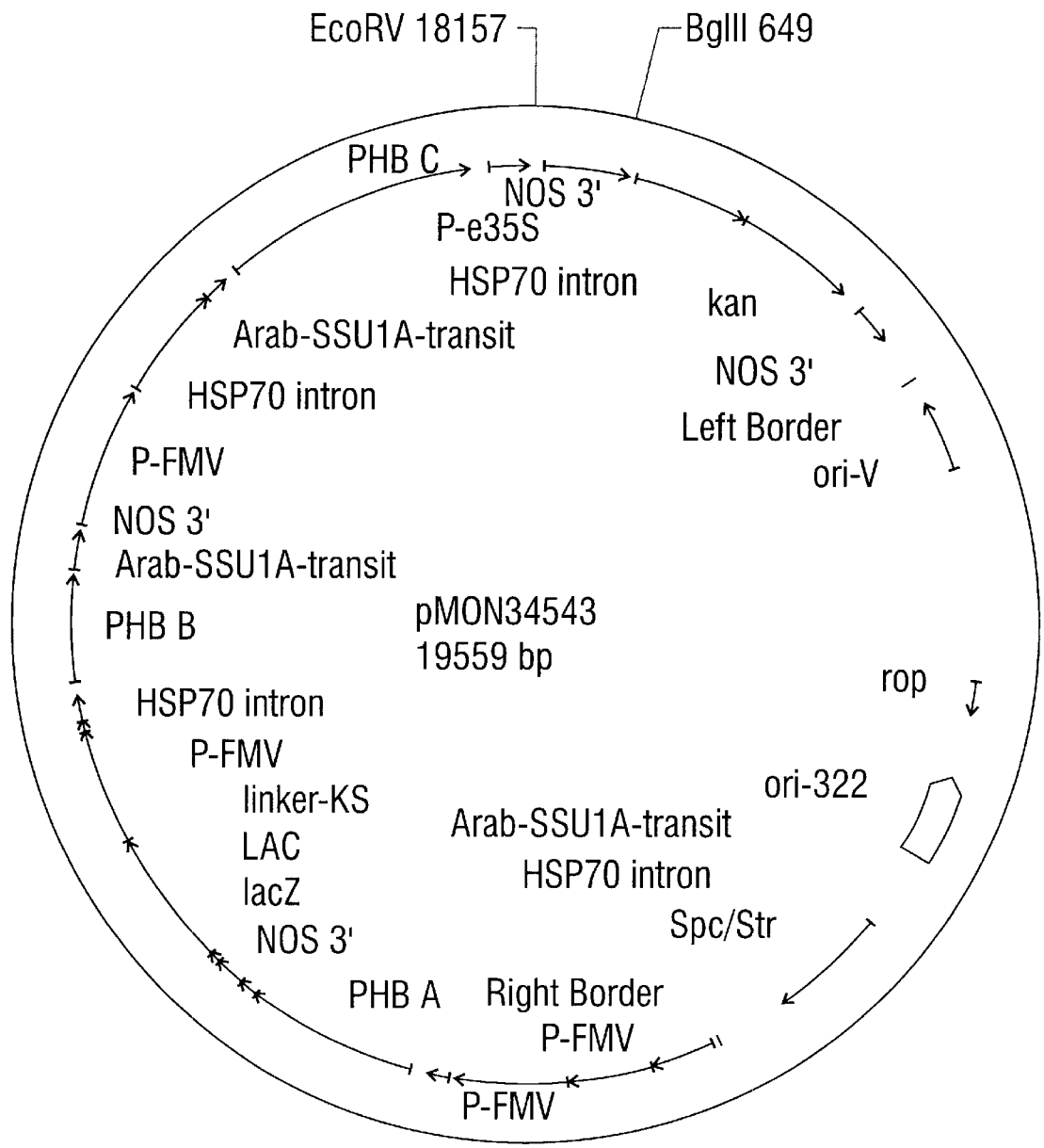
FIG. 27: Plasmid map of pMON34543. A list of the restriction enzyme cutting sites for pMON34543 is provided in Table 34.
Figure 28:
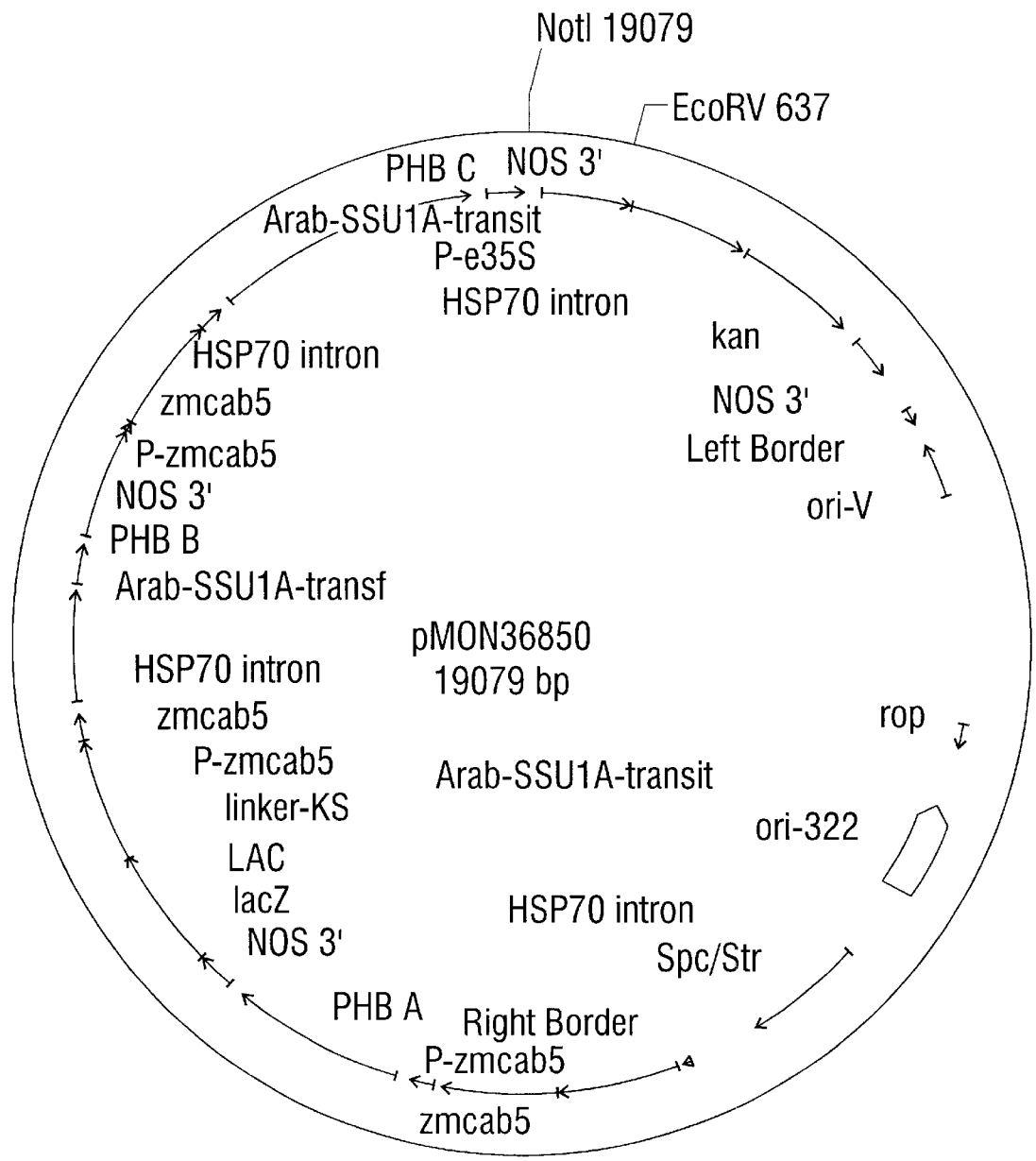
FIG. 28: Plasmid map of pMON36850. A list of the restriction enzyme cutting sites for pMON36850 is provided in Table 35.

For reasons described above, multigene vectors will also be desirable for expression of multi-enzyme metabolic pathways in monocots. Therefore, vectors designed to produce PHA in the leaves of maize were constructed. These vectors use the e35s, eFMV, or maize chlorophyll A/B binding protein (P-ChlA/B) promoters, and include the HSP70 intron designed to enhance expression in monocots. All enzymes were fused to the Arabidopsis RuBisCo small subunit transit peptide. Other promoters might also be used. Examples of vectors designed for gene expression in monocots are pMON36843 (FIG. 26), pMON34543 (FIG. 27), and pMON36850 (FIG. 28). These vectors have been used to transform maize, and polymer was analyzed as described above for Arabidopsis. Polymer production is summarized in Table 7.

TABLE 7

Polymer production in maize using multigene vectors.

| Vector number | Plant construct description | # of plants assayed | # of plants positive | C4 polymer (% dry wt.) |
|---|---|---|---|---|
| 36843 | P-e35S phbC | 93 | 11 | 1.14–4.81% |
|  | P-e35S phbA |  |  | AVE: 1.84% |
|  | P-e35S phbB |  |  | SD: 1.04% |
| 34543 | P-eFMV phbC | 34 | 34 | 0.15–2.95% |
|  | P-eFMV phbA |  |  | AVE: 0.7% |
|  | P-eFMV phbB |  |  | SD: 0.9% |
| 36850 | P-ChlA/B, phbC | 132 | 78 | 0.1–5.66% |
|  | P-ChlA/B, phbA |  |  | AVE: 1.72% |
|  | P-ChlA/B, phbB |  |  | SD: 1.17% |

Example 10
System for Construction of Large, Multigene Vectors

Figure 29:
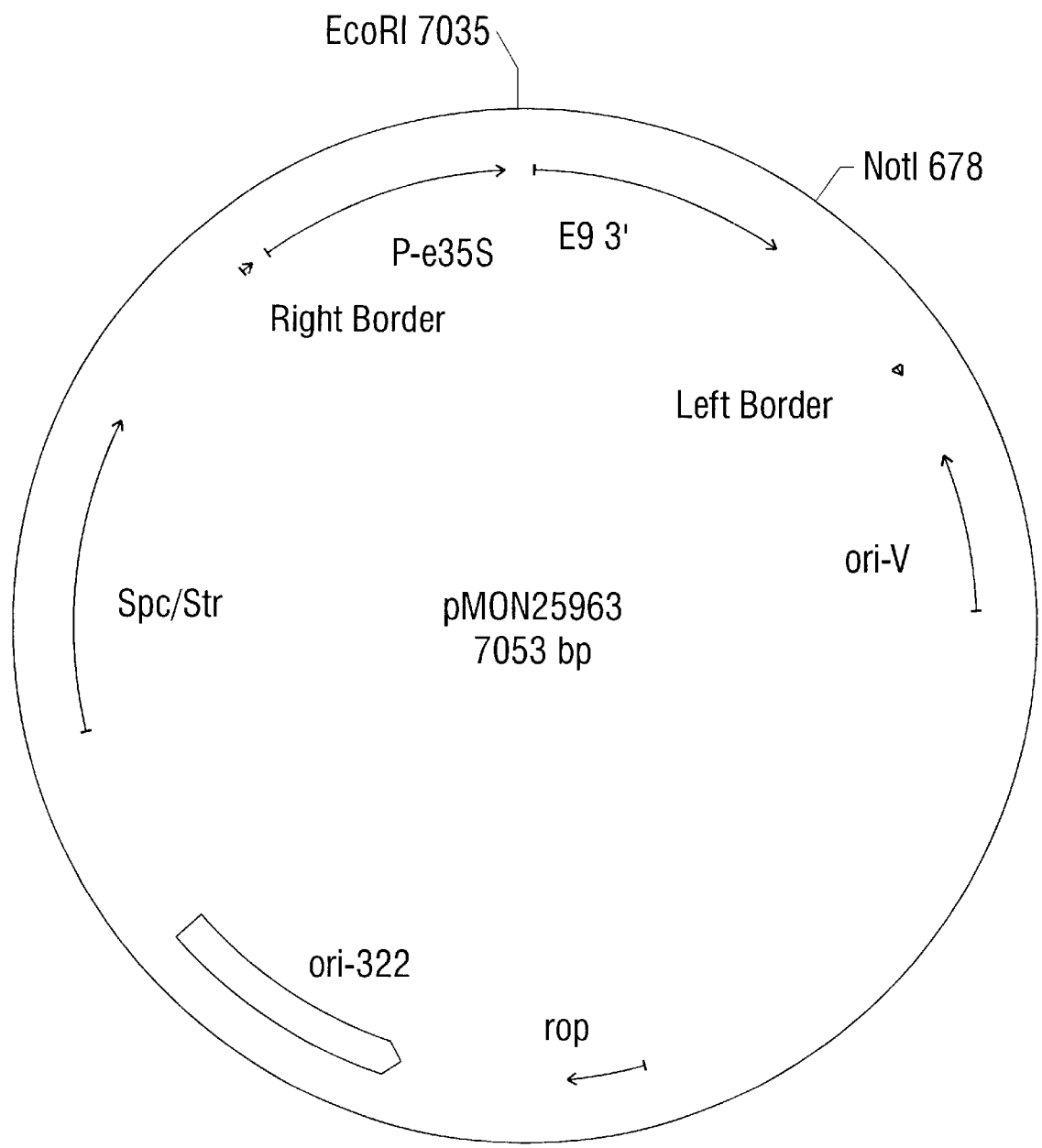
FIG. 29: Plasmid map of pMON25963. A list of the restriction enzyme cutting sites for pMON25963 is provided in Table 36.
Figure 30:
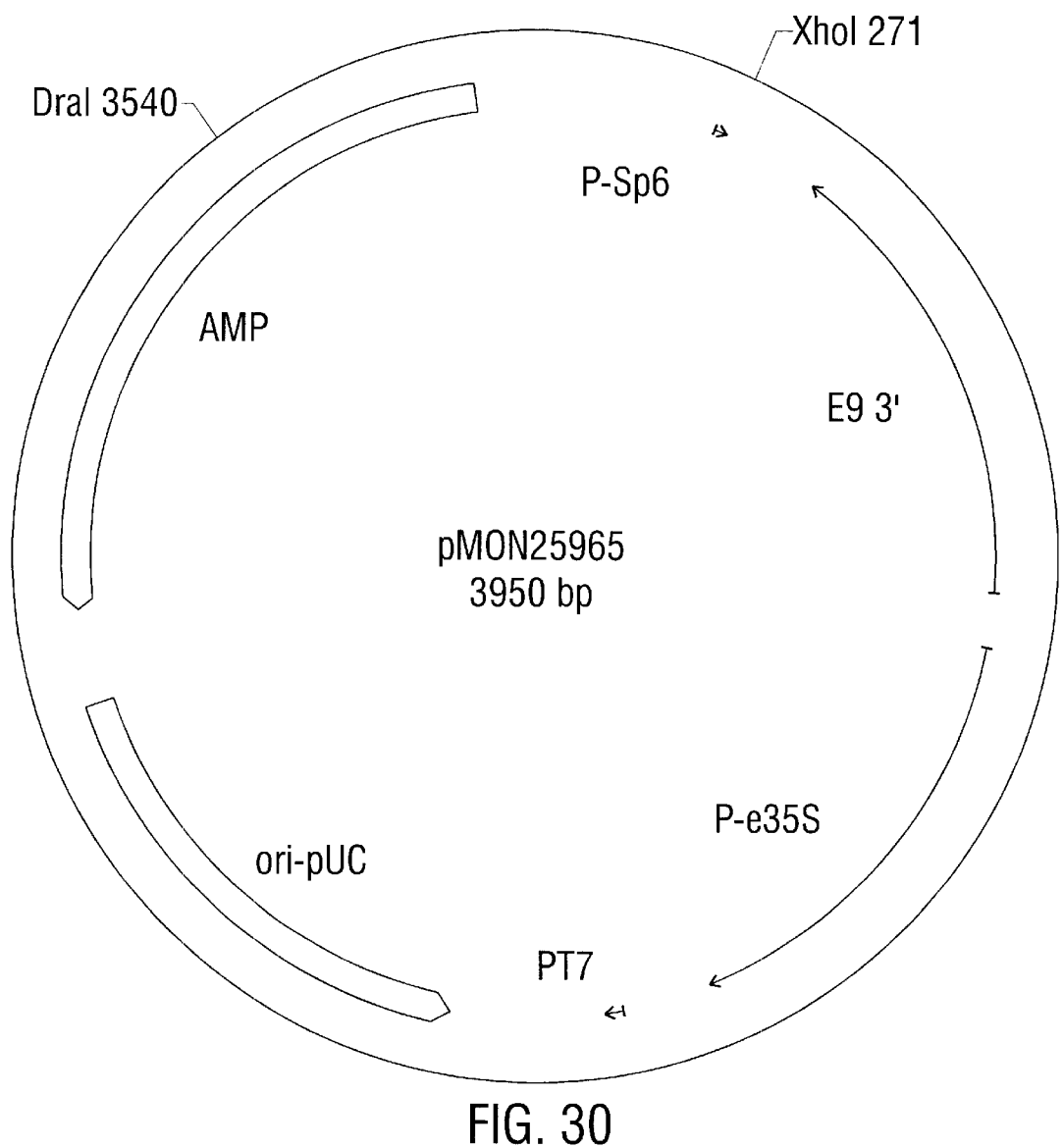
FIG. 30: Plasmid map of pMON25965. A list of the restriction enzyme cutting sites for pMON25965 is provided in Table 37.

Since multigene vectors are optimal for producing high levels of PHB, and this strategy is potentially optimal for expression of other multiple step pathways, a simple method to produce very large, multigene vectors is preferred. FIGS. 29 and 30 show plasmids pMON25963 and pMON25965, respectively. These vectors, used together, provide a system for constructing very large vectors. Plasmid pMON25965 provides a shuttle vector by which a gene cassette can be cloned into the NotI restriction sites and thereby be flanked by a series of restriction sites. These restriction sites are relatively rare in many genomes, and thereby of utility for subcloning many genes. Plasmid pMON25963 is a binary vector designed for transformation of plants by Agrobacterium. It contains a polylinker with the same sites found flanking the Noti restri ction sites of plasmid pMON25965. Using this system, a series of gene "cassettes" can be produced using plasmid pMON25965, and each can be sequentially ligated into plasmid pMON25963.

In practice, a series of vectors similar to pMON25965, but having smaller polylinkers, will be preferred. Specifically, this series of vectors would have a single NotI (or similar enzyme) restriction site flanked by one or several other restriction enzyme sites. By ligating cassettes flanked by large portions of the pMON25965 polylinker into pMON25963, relatively large inverted repeats of polylinker DNA are formed. These inverted repeats are unstable in *Escherichia coli,* and plasmids harboring them do not replicate efficiently. Thus, diminishing the size of the polylinker in the shuttle vector can increase the probability of recovering stable recombinants.

Figure 31:
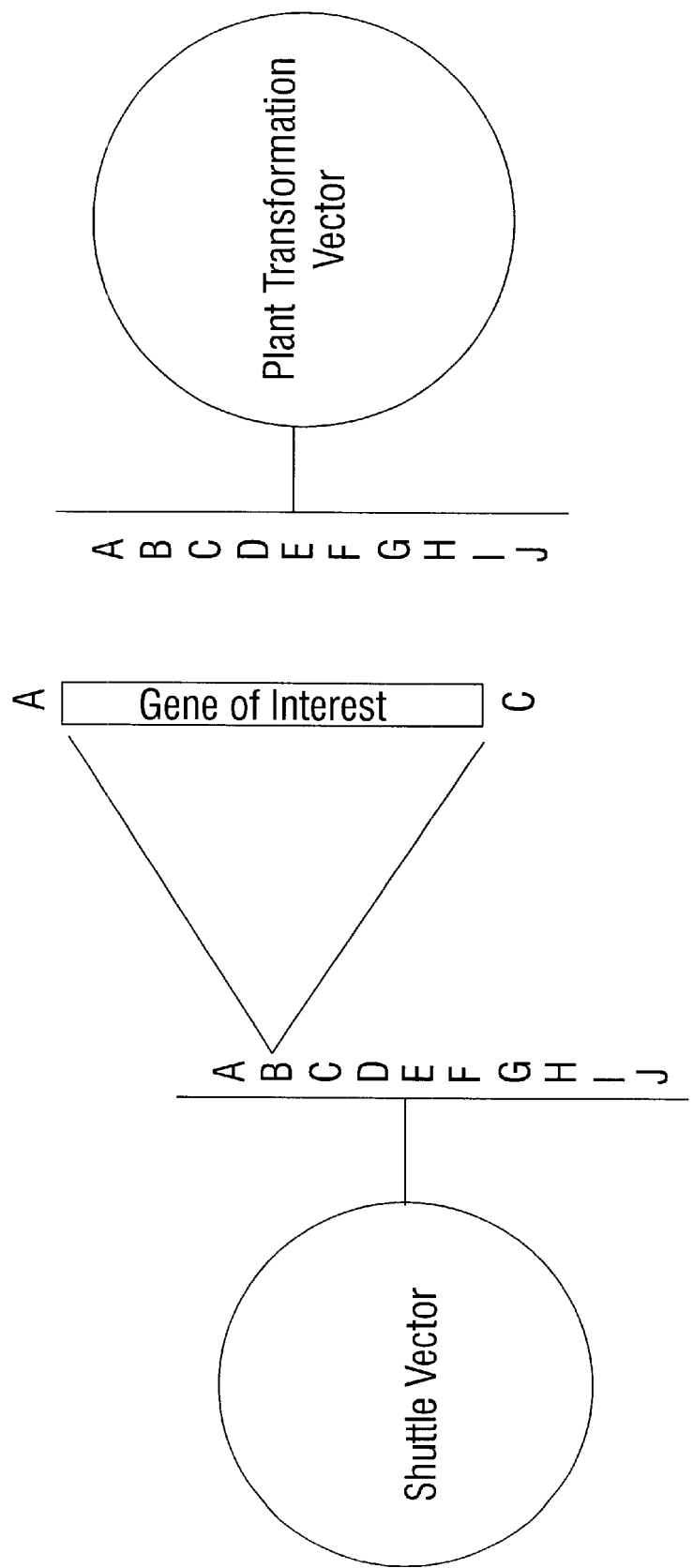
FIG. 31: Method for creating multi-gene vectors.

Another strategy for generating multigene vectors and reducing the levels of background caused by vector re-ligation is shown in FIG. 31. This strategy could be adapted to accommodate any number of enzymes, depending on the availability of unique restriction sites. One can easily design such a polylinker to accommodate one's cloning needs. As the vector becomes larger, one will want to have a larger homologous overlap for the ligation process or choose restriction endonucleases producing ends that are very easily ligated, and not self-compatible. By following the cloning procedure outlined in FIG. 31, one can also control the directionality of the clone. If directionality is not important than clones generated from the ligation into the "shuttle vector" in either orientation could be used. (A←C or A→C).

As with any multigene vector strategy, the starting plasmid used for constructing the large multigene plasmids should be taken into consideration. The common plant transformation plasmid pBIN19 (Frisch, D. et al., *Plant Mol Biol* 27: 405–409, 1995) has a starting size of 11,777 bp. In contrast plasmid pMON10098 (FIG. 4) has a starting size of 8431 bp. The major difference between the two plasmids is the loss of the trfA function which is encoded in trans in Agrobacterium strain ABI. Providing the trfA function in trans allows replication only in the specific strains of Agrobacterium engineered to harbor trfA. It has been shown by Figurski and Helinski (*Proc. Natl. Acad. Sci. U.S.A.* 76: 1648–1652, 1979) that replication factors can function in trans. By providing the minimal origins of replication required for maintenance in both *Escherichia coli* and Agrobacterium the starting size of the initial plasmid can be reduced significantly.

Other possibilities to reduce the size of the starting plasmid would be to delete oriT since this sequence is required for conjugational transfer only. If electroporation is used to introduce the plasmid into Agrobacterium, oriT is not an essential element. Another possibility would be to use selection that is functional in plants, Agrobacterium, and *Escherichia coli.* This could be accomplished by embedding into the plant promoter for the selectable marker a suitable bacterial promoter sequence and a ribosome binding site in proper context with the start codon on the selectable marker. One could also place this selectable marker on the plasmid flanked by its own right and left border sequences. This may allow for the selectable marker to be integrated into the plant chromosome unlinked to the genes of interest and potentially removed from subsequent generations. Alternatively, plants could be co-transformed by taking the multigene plasmid and cotransforming on a separate plasmid the selectable marker for plants. This would eliminate the cloning of the selectable marker on the multi gene plasmid. The selectable marker can be delivered by mixing two different Agrobacterium strains, one containing the multigene plasmid, and the other containing the selectable marker, or by using the same Agrobacterium strain but having different isolates containing either the multi gene plasmid or the selectable marker, or by having the selectable marker coexisting in the same Agrobacterium cell with the multigene vector, but on a separate plasmid with a compatible origin of replication.

One can also envision reducing the size of the selectable marker being used by using a trans complementation strategy. For example, one could transform a plant with a portion of a NptII gene that expresses a partial protein. If the transformation plasmid carries the complementary portion of the NptII protein, both fragments of the NptII protein may interact to confer resistance to kanamycin. This is analogous to the α-complementation strategy used for creating functional β-galactosidase (reviewed by Zabin, I. *Mol. Cell. Biochem.* 49: 87–96, 1982).

An example of an optimal starting plasmid for engineering multiple genes in plants would contain only the minimal essential elements required for replication in *Escherichia coli* and in Agrobacterium (having all other required functions encoded in trans) as well as a selection scheme that (1) reduces the need for redundancy in the selectable marker, and/or (2) reduces the size of the selectable marker, or (3) removes the necessity of having the plant selectable marker on the multi gene plasmid. The promoter used for driving the gene of interest in the multi gene vector should consist of the minimal essential elements required for temporal and spatial expression. The termination and polyadenylation signals should also contain only those sequences required for essential function.

Example 11
Poly(β-hydroxybutyrate) Production in Oilseed Leukoplasts of *Brassica napus*

Using plants as factories is attractive for the production of biodegradable plastics since current fermentation technology used for the commercial production of polyhydroxyalkanoates (PHA) is prohibitively expensive. The simplest PHA, poly-β-hydroxybutyrate (PHB), has previously been produced in leaves of *Arabidopsis thaliana* (Nawrath, C., et al., *Proc. Natl. Acad. Sci., U.S.A.,* 91: 12760–12764, 1994). *Brassica napus* oilseed, however, may provide a better system for PHB production because acetyl-CoA, the substrate required in the first step of PHB biosynthesis, is prevalent during fatty acid biosynthesis. Three enzymatic activities are needed to synthesize the PHB polymer: a β-ketothiolase, an acetoacetyl-CoA reductase and a PHB synthase. Genes from the bacterium *Ralstonia eutropha* encoding these enzymes were independently engineered behind the seed-specific *Lesquerella fendleri* oleate-12 hydroxylase promoter in a modular fashion. The gene cassettes were sequentially transferred into a single, multi-gene vector which was used to transform *Brassica napus*. PHB accumulated in leukoplasts to levels as high as 7.7% of seed dry weight. Electron microscopy analyses indicate that leukoplasts from these plants are distorted, yet intact, and appear to expand in response to polymer accumulation.

Polyhydroxyalkanoates (PHAs) comprise a class of biodegradable polymers which offer an environmentally-sustainable alternative to petroleum based plastics (reviewed by, Poirier, Y., et al., *Biotechnology,* 13: 142–150, 1995). The homopolymer Poly(β-hydroxybutyrate) (PHB), a particularly well studied PHA, is normally synthesized by various species of bacteria under conditions where nutrients become limited. PHB is stored in granules which can later be mobilized to provide a carbon and energy resource for the bacteria.

Figure 32:
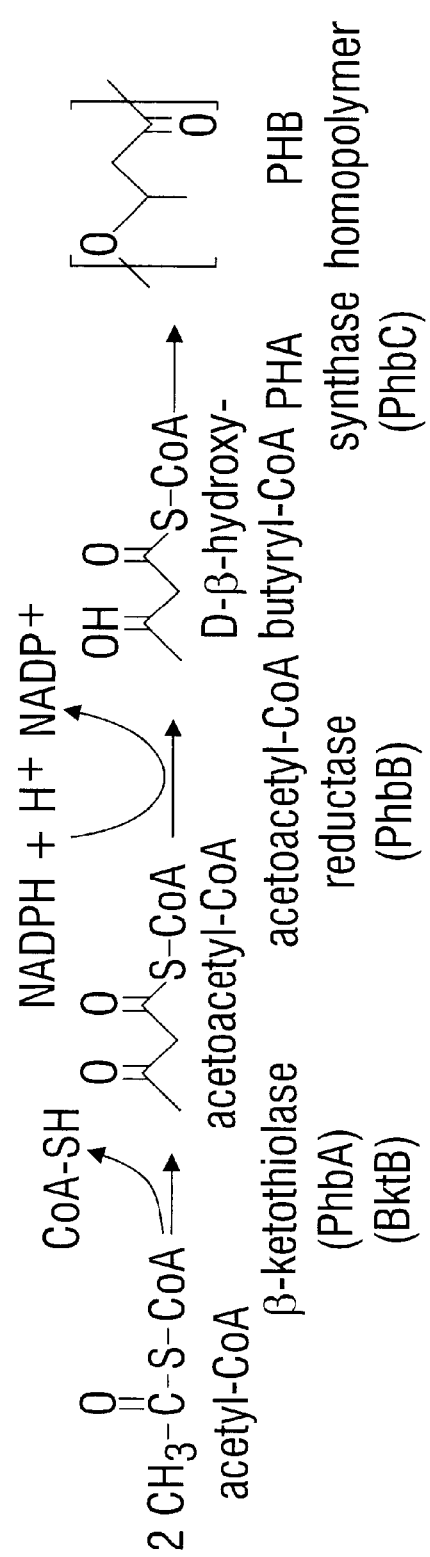
FIG. 32: PUB biosynthetic pathway. PHB production requires the condensation of two acetyl-CoA molecules using a β-ketothiolase, a D-isomer-specific reduction by acetoacetyl-CoA reductase, and PHB polymerization by PHB synthase. The genes encoding these enzymes are indicated in parentheses.

One of the best-studied pathways for PHB synthesis is derived from the bacterium *Ralstonia eutropha* (Slater, S. C., et al, *J. Bacteriol.,* 170: 4431–4436, 1988; Schubert, P., et al., *J. Bact.,* 170: 5837–47, 1988; Peoples, O. P., and Sinskey, A. J., *J. Biol. Chem.,* 264: 15298–15303, 1989; Peoples, O. P., and Sinskey, A. J., *J. Biol. Chem.,* 264: 15293–15297, 1989). The pathway requires three enzymes: a β-ketothiolase, an acetoacetyl-CoA reductase, and a PHB synthase (FIG. 32). *R. eutropha* uses least two β-ketothiolases, PhbA and BktB (Slater, S. C., et al.,*J. Bact.,* 180: 1979–1987, 1998), and both of these enzymes were used in this study. The acetoacetyl-CoA reductase and PHB synthase are designated PhbB and PhbC, respectively (Peoples, O. P., and Sinskey, A. J., *J. Biol. Chem,* 264: 15298–15303, 1989; Peoples, O. P., and Sinskey, A. J., *J. Biol. Chem.,* 264: 15293–15297,1989).

*R. eutropha* is fermented commercially for PHA production, but the process is not economically competitive with polymers derived from petroleum. Therefore, novel commercial efforts to produce PHAs focus on using plants as polymer factories. In this respect, our laboratory is considering two model systems: production in leaves and production in seeds. Since acetyl-CoA is a central metabolite for both PHB and fatty acid biosynthesis, and *Brassica napus* seeds are extremely efficient in oil production, the Brassica seeds seem an optimal environment in which to produce PHB (U.S. Pat. No. 5,502,273). Production of PHB in *Arabidopsis thaliana* leaves has been achieved using *R. eutropha* enzymes (Poirier, Y., et al., *Science,* 256: 520–523, 1992), and additional work showed that polymer accumulation up to 14% of plant dry weight was achieved when the PHB biosynthetic enzymes were targeted to the plastid (Nawrath, C., et al., *Proc. Nat. Acad Sci.,* 91: 12760–12764, 1994).

Figure 33:
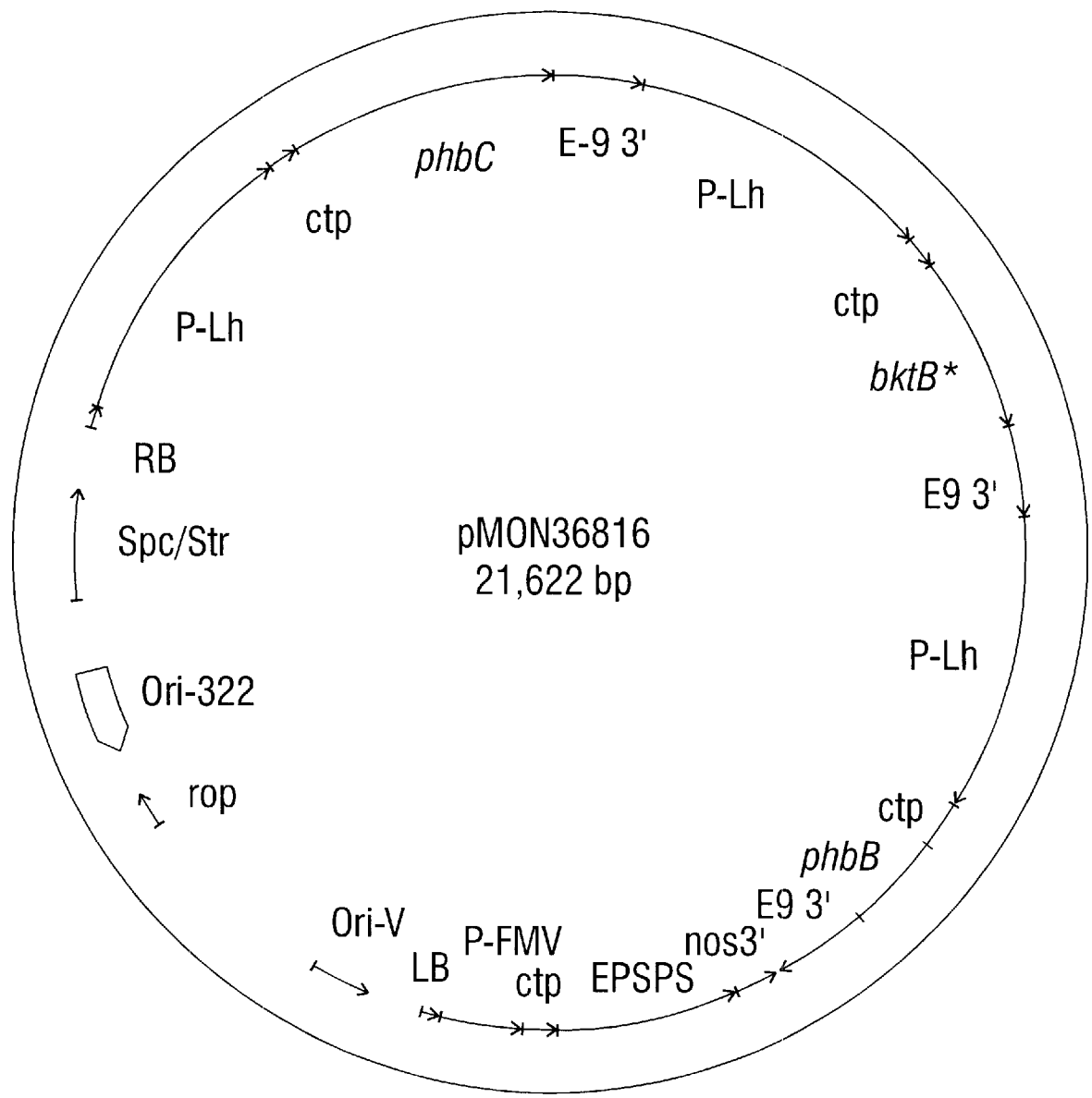
FIG. 33: Schematic diagram of multi-gene vector used to transform *Brassica napus*. Vectors were constructed using modular cassettes. Each cassette consists of the Lesquerella hydroxylase promoter (P-Lh), a chloroplast transit peptide (ctp) fused to an open reading frame encoding a PHB synthesis enzyme, and the E9 3' terminator. The plasmid also expresses EPSP synthase to provide resistance to glyphosate, contains bacterial replication origins, and a bacterially-expressed gene encoding resistance to streptomycin and spectinomycin. In pMON36814, bktB was replaced with phbA. Otherwise, the vectors were identical. RB, right border of T-DNA; LB, left border of T-DNA.

The work presented here demonstrates polymer production in the seeds of *Brassica napus* using a multi-gene vector approach. A significant advantage to using these multi-gene vectors is that the entire PHA pathway is introduced simultaneously, thereby obviating the need for elaborate crossing strategies and eliminating the problems associated with insertional effects at multiple loci. Construction of these multi-gene vectors involved the generation of modular cassettes, each harboring an individual gene. The cassettes were then assembled into a single vector expressing the entire PHB biosynthetic pathway (FIG. 33). Each cassette consisted of the *Lesquerella fendleri* oleate-12 hydroxylase promoter (Broun, P., et al., *Plant J.,* 13: 201–210, 1998), a chloroplast transit peptide fused to the open reading frame of interest (bktB, phbA, phbB, or phbC), and the 3' termination region of the *Pisum sativum* rbcSE9 gene (Coruzzi, G., et al., *EMBO J.,* 3: 1671–1679, 1984). The Lesquerella promoter contains 2.2 kb of DNA upstream of the coding region for the oleate-12 hydroxylase gene. This promoter was chosen because it is expressed concurrently with the accumulation of storage lipid (Broun, P., et al., *Plant J.,* 13: 201–210, 1998).

Expression of the PHB pathway in *B. napus* was achieved using Agrobacterium-mediated transformation, and glyphosate selection was used to identify transgenic events (Fry, J., et al., *Plant Cell Rep.*, 6: 321–325, 1987). The T-DNA transferred into the plants from these experiments exceeded 16 kilobases in size. The co-expression rate of genes from the multi-gene vectors in Brassica seeds was high, with 87% of the glyphosate resistant plants also producing polymer. Polymer levels ranged from 0.02–7.7% for the transgenic plants carrying pMON36814 (*R. eutropha* phbA, phbB, phbC) and 0.02–6.3% for those carrying pMON36816 (*R. eutropha* bktB, phbB and phbC). The vast majority of plants producing polymer fall within the 0–3.0% polymer range (Table 8) and all polymer-producing lines generated viable seed.

TABLE 8

Polymer results from canola multigene vector transformations.

| Vector | Genetic elements | # of plants assayed | # of plants positive | C4 polymer (% dry wt.) |
|---|---|---|---|---|
| 36814 | p-Lh, phbC<br>p-Lh, phbA<br>p-Lh, phhB | 208 | 180 | 0.02%–7.68%<br>Avg: 1.73%<br>SD: 1.45% |
| 36816 | p-Lh, phbC<br>p-Lh, bktB<br>p-Lh, phbB | 225 | 195 | 0.02%–6.28%<br>Avg: 1.00%<br>SD: 1.02% |

Figure 34A:
FIG. 34A: Electron of *Brassica napus* plastids leucoplast from wild type *Brassica napus* seed.
Figure 34B:
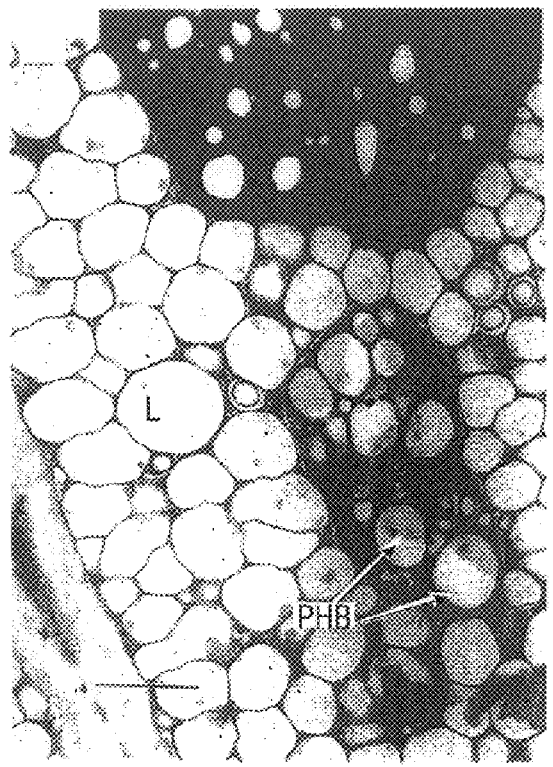
FIG. 34B: Electron micrographs of leucoplast from *Brassica napus* seed producing PHB. Polymer (PHB) and oil bodies (O) are indicated. Note the greatly expanded size of leukoplasts in the PHB-producing line.

The *B. napus* line displaying 7.7% polymer was further analyzed by electron microscopy. Micrographs revealed that polymer accumulated within the plastid (FIG. 34), and that essentially every plastid contained polymer. Polymer production in the plastids is seemingly well tolerated; the size of the plastid expands to accommodate polymer production (compare FIGS. 34A and 34B). This phenomenon is similar to the size changes observed when amyloplasts accumulate starch, and suggests that plastids will change size to accommodate accumulation of any granular product. Thus, the signal initiating an increase in plastid volume is not specifically linked to accumulation of normal metabolites; rather, the increase is probably initiated simply by physical pressure applied to the plastid membrane.

These results demonstrate that PHA accumulation is possible in an oilseed system. Commercial oilseed PHA production will require approximately twice the amount of PHA accumulation achieved here. Moreover, commercial success will rely on the development of an integrated processing system to extract PHA, oil, and meal from the seeds. We believe that increases in PHA accumulation can be obtained using alternative promoters that are stronger and expressed for a longer duration during seed development. Other concerns regarding the feasibility of PHA production in planta largely revolve around the metabolic effects of PHA production in oilseeds. Specifically, analysis of the effect of PHA production on oil yield will be of particular interest, since both are derived from acetyl-CoA and produced simultaneously. Any untoward effect of PHA production on oil yield or seed quality will impact negatively on the economic feasibility of using *B. napus* as a commercial system.

Vector Construction and Plant Transformation

A single vector encoding the entire PHB biosynthetic pathway was used for Agrobacterium-mediated transformation of Brassica. This vector, pMON36814, encodes bktB, phbB, and phbC (FIG. 33). Each gene of interest was fused to a chloroplast transit peptide (ctp), so each protein is transported to the seed leukoplast. All enzymes were fused to the Arabidopsis RuBisCo small subunit 1a transit peptide that was previously used for PHB production (Nawrath, C, et al., *Proc. Nat. Acad. Sci.*, 91: 12760–12764, 1994) except PhbB was fused to the transit peptide from pea RuBisCo small subunit (Cashmore, A. R., eds. Kosuge, T., Meredith C. P., Hollaender, A., (Plenum, New York), 29–38, 1983). Each gene is controlled by the promoter from the fatty acid hydroxylase gene of Lesquerella (P-Lh; Broun, P., et al., *Plant J.*, 13: 201–210, 1998), and terminated with the E9 3' region of the Pisum rbcSE9 gene (Coruzzi, G., et al., *EMBO J.*, 3: 1671–1679, 1984). P-Lh directs expression of these genes within the developing seed. The selection cassette for pMON36812 and 36814 consisted of the Figwort Mosaic Virus promoter followed by the Petunia RuBisCo small subunit 1a transit peptide, the Petunia EPSP synthase gene (CP4) and nopaline synthase 3' termination/polyadenylation region (nos3').

Transformation of *Brassica napus* was done as described in Fry, J. et al. (*Plant Cell Rep.*, 6: 321–325, 1987) using glyphosate for selection.

Polymer Analysis

For isolation of polymer from canola seed, seeds were ground to a fine powder with a mortar and pestle. Approximately 200 mg of each sample were extracted two times in a glass tube with 10 mL each of hexane for 1 hour at 60° C., then two times with 10 mL each of 100% methanol for one hour at 60° C. This procedure removes oil from the seed. The material was allowed to dry completely overnight. Polymer was extracted from the dried material with 1 mL of chloroform containing 3 $\mu$mol/mL methyl-benzoate standard. The tube was heated to 100° C. for 5 hours and the samples were cooled. One mL methanol/sulphuric acid (85:15, v/v) was added, and the mixture was heated to 100° C. for exactly 2.5 hours. The solution was cooled, extracted with water and subjected to gas chromatography. Gas chromatographic characterization of the methyl-ester residues was performed as described by (Slater, S., et al., *J. Bact.*, 180: 1979–1987, 1998) except that the temperature gradient was performed as follows: the initial temperature of 70° C. was held for 6 minutes, then the temperature was increased by 30° C. per minute to 130° C. Finally, the temperature was increased by 50° C. per minute to 300° C. and held at 300° C. for 5 minutes.

Electron Microscopy

Partial imbibition of Brassica seeds was achieved by the slight abrasion of the seed coats, followed by placement for 2 hours onto filter paper moistened with distilled water. The cotyledons of these seeds were then cut into 1 mm$^3$ pieces and fixed in 4% glutaraldehyde in 0.1 M sodium cacodylate buffer, pH 7.2 for three hours, with the first 30 minutes under vacuum. The tissue was post-fixed in 1% osmium tetroxide in the above buffer, dehydrated in ethanol and propylene oxide and infiltrated with a 1:1 mixture of Spurr's: EMbed 812 resin. The resin was polymerized at 60° C. for 48 hours. The resulting blocks were sectioned on an Leica Ultracut E microtome. Sections 80 nm thick were picked up on formvar/carbon coated copper slot grids. The grids were post-stained with uranyl acetate and lead citrate in an LKB ultrastainer and examined with a JEOL 1200 transmission electron microscope. (All reagents were obtained from Electron Microscopy Sciences, Fort Washington, Pa.).

Example 12

Metabolic Engineering of Arabidopsis and Brassica for Poly($\beta$-hydroxybutyrate-co-$\beta$-hydroxyvalerate) Copolymer Production Poly(hydroxyalkanoates) are natural polymers with. thermoplastic properties. One polymer of this class, poly($\beta$-hydroxybutyrate-co-$\beta$-hydroxyvalerate) (PHBV) is currently produced by bacterial fermentation, but the process is not economically competitive with polymer production from petrochemicals. PHA production in green plants promises much lower costs, but producing polymer with the appropriate monomer composition is problematic. By redirecting metabolic pools of both short-chain fatty acids and amino acids, Arabidopsis and Brassica have now been engineered to produce PHBV, a copolymer with commercial applicability. In this Example, polymer production, metabolic intermediate analyses, and pathway dynamics for PHBV synthesis in planta are described.

Poly(hydroxyalkanoates) (PHAs) are a class of polymers accumulated by numerous bacterial species as carbon and energy reserves. These polymers have thermoplastic properties, and have received much attention as biodegradable alternatives to petrochemical plastics (Anderson, A. J., and Dawes, E. A. *Microbiol. Rev.* 54: 450–472, 1990). While the homopolymer poly(β-hydroxybutyrate) (PHB) is somewhat brittle, many copolymers such as poly(β-hydroxybutyrate-co-β-hydroxyvalerate) (PHBV) are more flexible due to reduced crystallinity, and suitable for many commercial applications.

The biochemical pathways for PHB and PHBV production are essentially identical, differing only in the initial metabolites. PHB synthesis is initiated by condensation of two acetyl-CoA molecules, whereas PHBV synthesis requires the additional condensation of acetyl-CoA with propionyl-CoA. Following condensation, the products are reduced by a D-isomer specific acetoacetyl-CoA reductase, and the resulting β-hydroxy products are polymerized by PHB synthase (Anderson, A. J., and Dawes, E. A. *Microbiol. Rev.* 54: 450–472, 1990; Steinbüchel and Schlegel, *Mol. Microbiol.* 5(3):535–42, 1991).

PHBV is produced commercially by growing *Ralstonia eutropha* on glucose and propionate (Byrum, D. *FEMS Microbiol. Rev.* 102: 247–250, 1992), but the cost of this process prohibits large-scale fermentation. Production of PHAs via genetic engineering of green plants is expected to reduce costs to economical levels (van der Leij, F. R., and Witholt, B. *Can. J Microbiol.* 41(Suppl.1): 222–238, 1995), and production of PHB homopolymer in plants has been demonstrated (Poirier, Y., et al. *Science* 256: 520–523, 1992; Nawrath, C.; et al. *Proc. Natl. Acad. Sci.* 91: 12760–12764, 1994). However copolymer production has been problematic, primarily due to the requirement for metabolic precursors other than acetyl-CoA.

Here we report metabolic engineering of plants to produce PHBV copolymer. By expressing four distinct transgenes and diverting metabolic pools of acetyl-CoA and threonine, copolymer was produced in *Arabidopsis thaliana*, and in the seeds of *Brassica napus* (oilseed rape). PHBV copolymer production opens the use of green plants as factories for commercial, environmentally-sustainable production of biodegradable plastics.

Figure 35:
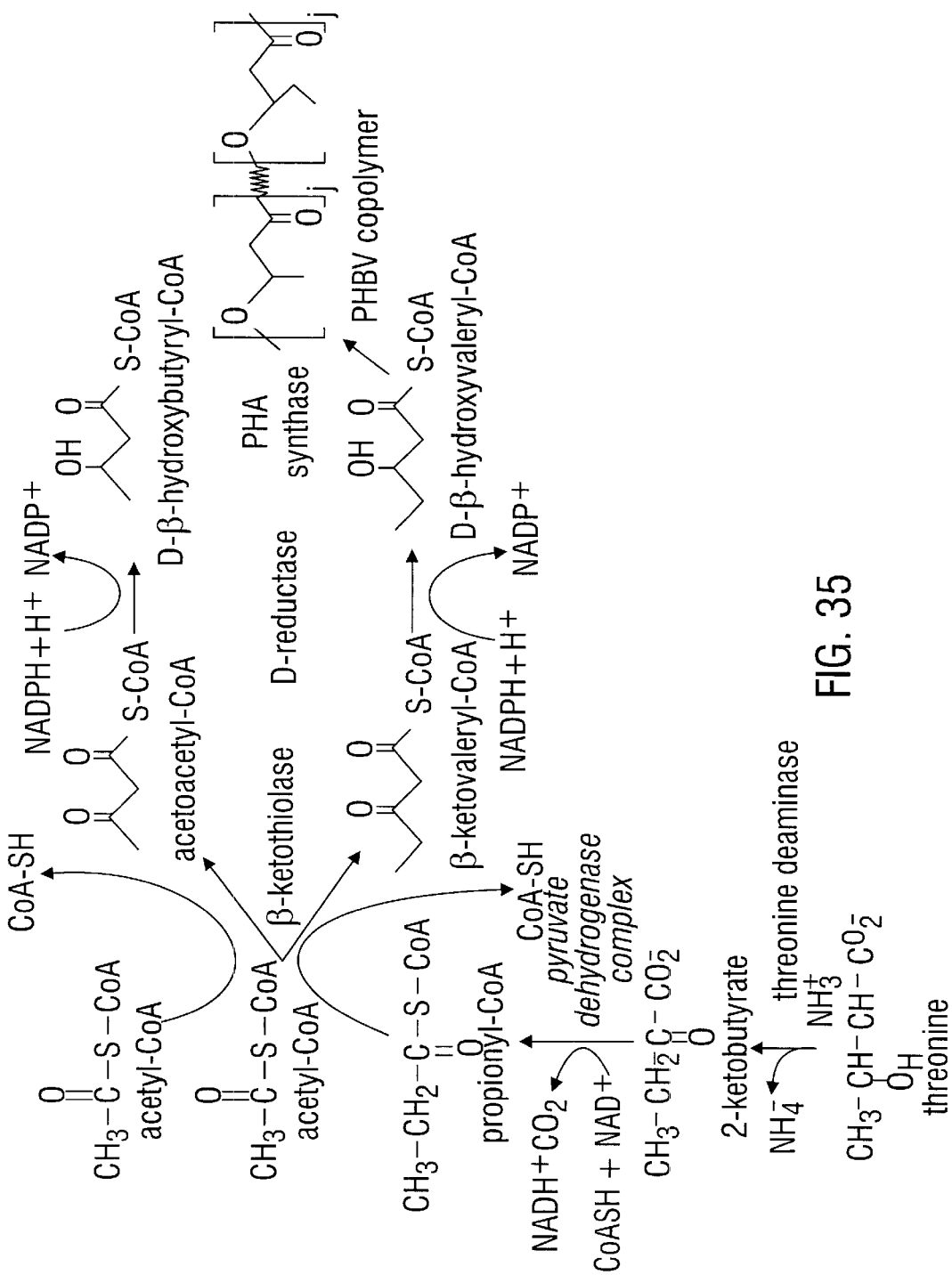
FIG. 35: A pathway designed to produce poly(β-hydroxybutyrate-co-β-hydroxyvalerate) in the plastids of plants. Propionyl-CoA is derived from threonine via threonine deaminase and the pyruvate dehydrogenase complex. Acetyl-CoA is drawn from normal intermediary metabolism. The pathway requires transformation of the plant with four genes (ilvA, bktB, phbB, and phbC), and relies on endogenous pyruvate dehydrogenase. All enzymes encoded by transgenes are targeted to the plastid using chloroplast transit peptides.

Results: A Pathway for Poly(β-hydroxybutyrate-co-β-hydroxyvalerate) Production in Plants A pathway designed to engineer PHBV production in the plastids of plants is diagrammed in FIG. 35. Acetyl-CoA is drawn from plastid intermediary metabolism, whereas propionyl-CoA is generated from threonine via 2-ketobutyrate (Gruys et al WO 98/00557; Eschenlauer, A. C., et al. *Int. J. Biol. Macromol.* 19: 121–130, 1996). This pathway requires transformation of the plant with four separate genes: ilvA, bktB, phbB, and phbC. It also relies on the endogenous plastid pyruvate dehydrogenase complex (PDC). The threonine deaminase used in these studies is the biosynthetic enzyme IlvA from *E. coli* (Taillon, B. E., et al. *Gene* 63: 245–252, 1988). The acetoacetyl-CoA reductase (PhbB) and PHB synthase (PhbC) are the same *R. eutropha* enzymes used in earlier in planta studies (Poirier, Y., et al. *Science* 256: 520–523, 1992; Nawrath, C.; et al. *Proc. Natl. Acad. Sci.* 91: 12760–12764, 1994). The β-ketothiolase is BktB from *R. eutropha* (Slater, S., et al. *J. Bacteriol.* 180: 1979–1987, 1998). Previous work on PHB production in plants used the *R. eutropha* PhbA β-ketothiolase. However, PhbA cannot efficiently synthesize β-ketovaleryl-CoA, whereas BktB produces both β-ketovaleryl-CoA and acetoacetyl-CoA.

Metabolic Engineering of Arabidopsis and Brassica

Polymer production was studied in both *Arabidopsis thaliana* leaves and *Brassica napus* seeds. For PHBV production in Arabidopsis, two separate vectors were constructed. Plasmid pMON25678 encodes phbB and phbC, and plasmid pMON25812 encodes bktB and ilvA. Transgenic Arabidopsis were generated by simultaneous Agrobacterium-mediated transformation with both vectors, and subsequent selection on both glyphosate and kanamycin. All genes were controlled by the e35S promoter (Odell, J. T., et al. *Nature* 313: 810–812, 1985), leading to polymer production throughout the plant. In Brassica, all four genes in the transgenic pathway were expressed from a single vector, pMON36824, and polymer production was directed to the seeds by the Lesquerella hydroxylase promoter (Broun, P., et al. *Plant J.* 13: 201–210, 1998).

Previous work on PHA production in plants has shown that polymer is produced efficiently and that phenotypic effects on the plant are minimized when PHA production occurs in the chloroplasts (Nawrath, C. et al. *Proc. Natl. Acad. Sci.* 91: 12760–12764, 1994). The plastids are the site for synthesis of both oil, which is derived from acetyl-CoA, and threonine which is used to produce propionyl-CoA. In both Arabidopsis and Brassica, the PHA biosynthesis enzymes were targeted to the plastids using chloroplast transit peptides. In photosynthetic tissues of Arabidopsis the proteins are targeted to the chloroplasts, whereas in Brassica seeds the enzymes are targeted to the leucoplasts.

Generation of Propionyl-CoA from Threonine

Conversion of threonine to 2-ketobutyrate by IlvA is the first reaction catalyzed by one of the recombinantly-encoded enzymes. IlvA normally catalyzes the initial step in the conversion of threonine to isoleucine, and the enzyme is feedback-inhibited by isoleucine (Umbarger, H. E. Biosynthesis of branched-chain amino acids, pp. 442–457 in *Escherichia coli* and Salmonella: Cellular and Molecular Biology, Neidhart, F. C., Curtiss, R., Lin, E. C. C., Low, K. B., Magasanik, B., Reznikoff, W. S., Riley, M., Schaechter, M., and Umbarger, H. E. (eds.).ASM Press, Washington, D.C., 1996). However, ilvA mutants with diminished sensitivity to isoleucine have been described and two such mutants, ilvA466 (Pledger, W. J., and Umbarger, H. E. *J. Bacteriol.* 114: 183–194, 1973; Taillon, B. E., et al. *Gene* 63: 245–252, 1988) and ilvA219 (Burns, R. O., et al. *J. Biol. Chem.* 254: 1074–1079, 1979; Eisenstein, E., et al. *Biochemistry* 34: 9403–9412, 1995), were used along with wild-type ilvA in these studies. IlvA466 is partially sensitive to feedback inhibition by isoleucine, and IlvA219 is essentially insensitive (Pledger, W. J., and Umbarger, H. E.*J. Bacteriol.* 114: 195–207, 1973; LaRossa, R. A., et al. *J. Bacteriol.* 169: 1372–1378, 1987).

Both Arabidopsis and Brassica were initially transformed with separate vectors expressing wild-type ilvA, ilvA466, and ilvA219. In both organisms, no fertile transformants expressing ilvA219 were recovered, indicating that expression of completely isoleucine-insensitive IlvA is lethal. In Arabidopsis, plants expressing ilvA466 were recovered at a very low frequency, whereas Brassica tolerated ilvA466 rather well. This result may be due to the seed-specific nature of the Lesquerella promoter. Transformants expressing wild-type ilvA were efficiently recovered in both Arabidopsis and Brassica.

Figure 36A:
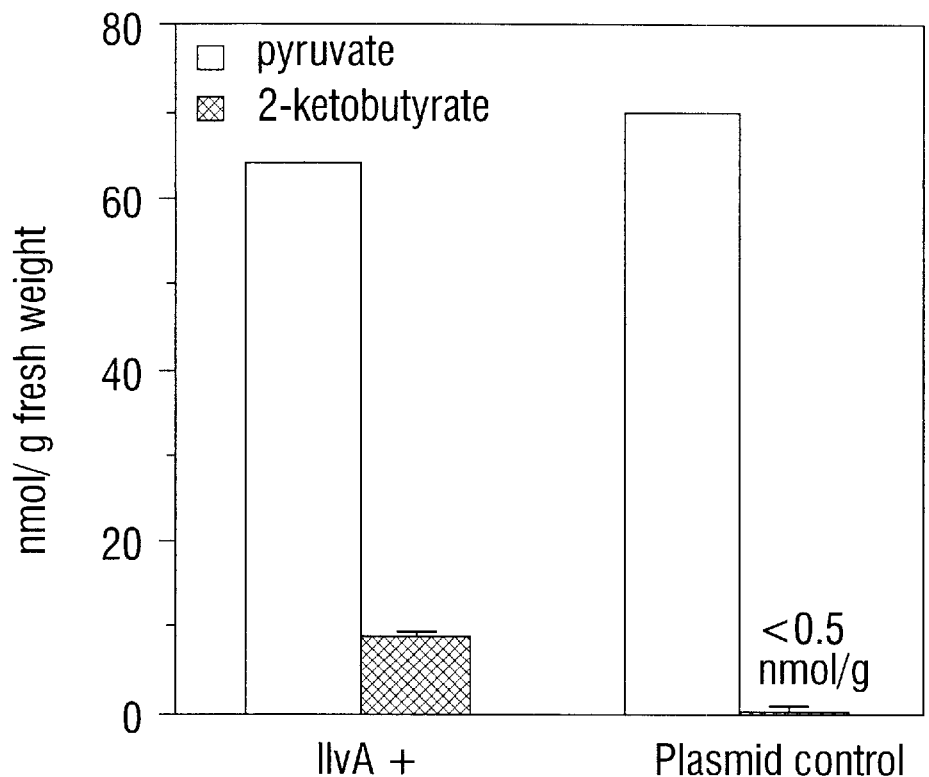
FIG. 36A: Comparison of pyruvate and 2-ketobutyrate concentrations in Arabidopsis harboring either a control plasmid or a plasmid expressing wild type *E. coli* ilvA (threonine deaminase).
Figure 36B:
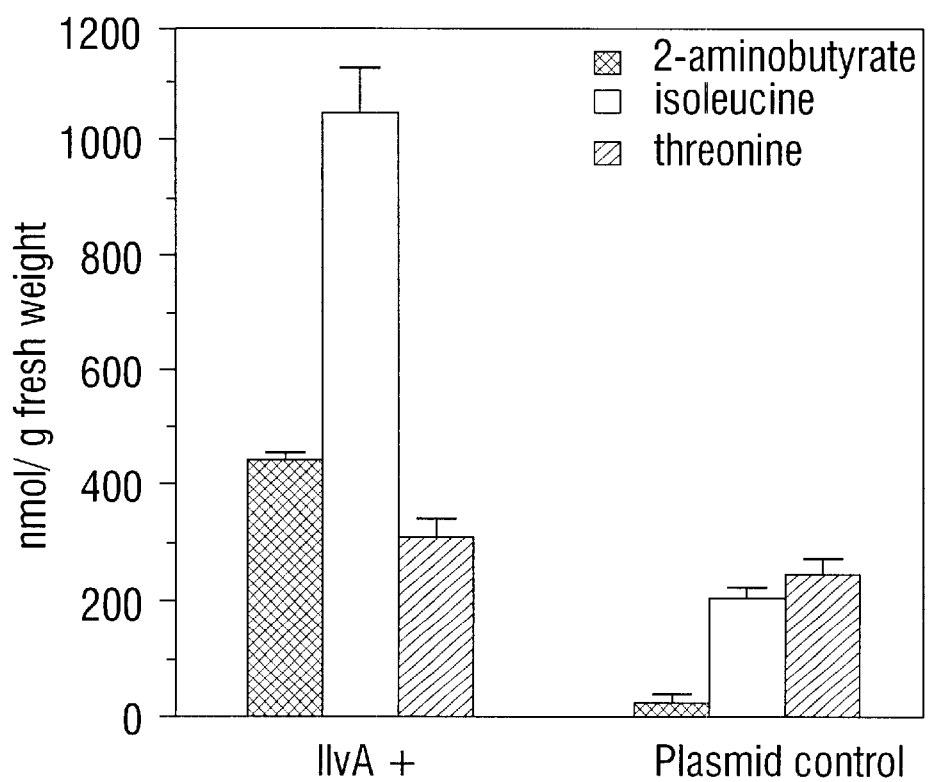
FIG. 36B: Comparison of threonine, isoleucine, and 2-ketobutyrate concentrations in Arabidopsis harboring either a control plasmid or a plasmid expressing wild type *E. coli* ilvA (threonine deaminase). Note the different scales used in parts (A) and (B).

In order to monitor the metabolic effects of IlvA in transgenic plants, metabolites likely to be effected by this enzyme were analyzed. FIG. 36 shows profiles of selected 2-ketoacids and amino acids in a control plant, and in transgenic Arabidopsis expressing wild-type ilvA. As expected, the transgenic plant had elevated levels of both 2-ketobutyrate and isoleucine. In addition, a high concentration of 2-aminobutyrate was present. Formation of 2-aminobutyrate from 2-ketobutyrate is a freely-reversible reaction, probably catalyzed by the same branched-chain amino acid transaminase that catalyzes the final step in isoleucine biosynthesis (Singh, B. K. (1999) Biosynthesis of Valine, Leucine and Isoleucine. In: Singh, B. K. (ed.) Plant Amino Acids: Biochemistry and Biotechnology. Marcel Dekker, Inc., New York, pp.227–247, 1998). Although transgenic plants expressing ilvA contained more 2-ketobutyrate than did wild-type plants, the 2-ketobutyrate concentration was still below that of pyruvate. Most 2-ketobutyrate was apparently diverted to produce 2-aminobutyrate and isoleucine. The concentration of free threonine in a plant expressing ilvA decreased by only about 15%, suggesting that threonine synthesis was sufficiently robust to compensate for the diversion of threonine through 2-ketobutyrate. Similar analyses were performed on the seeds from control and transgenic Brassica, and essentially the same results were obtained. In plants expressing ilvA, isoleucine, 2-ketobutyrate, and 2-aminobutyrate concentration s were elevated, and free threonine was only marginally decreased (K. Gruys et al., unpublished data).

The second step in the formation of propionyl-CoA is catalyzed by the plastid pyruvate dehydrogenase complex, which is the sole endogenous enzyme required for PHBV production. This enzyme complex normally plays a central role in metabolism by converting pyruvate to acetyl-CoA. We found that PDC from isolated Brassica leukoplasts was also capable of converting 2-ketobutyrate to propionyl-CoA. However, PDC was approximately 10-fold less efficient when utilizing 2-ketobutyrate than when utilizing pyruvate; the specific activities were 0.4 units/mg and 3.6 units/mg for 2-ketobutyrate and pyruvate, respectively.

Synthesis of PHBV Copolymer

Figure 37:
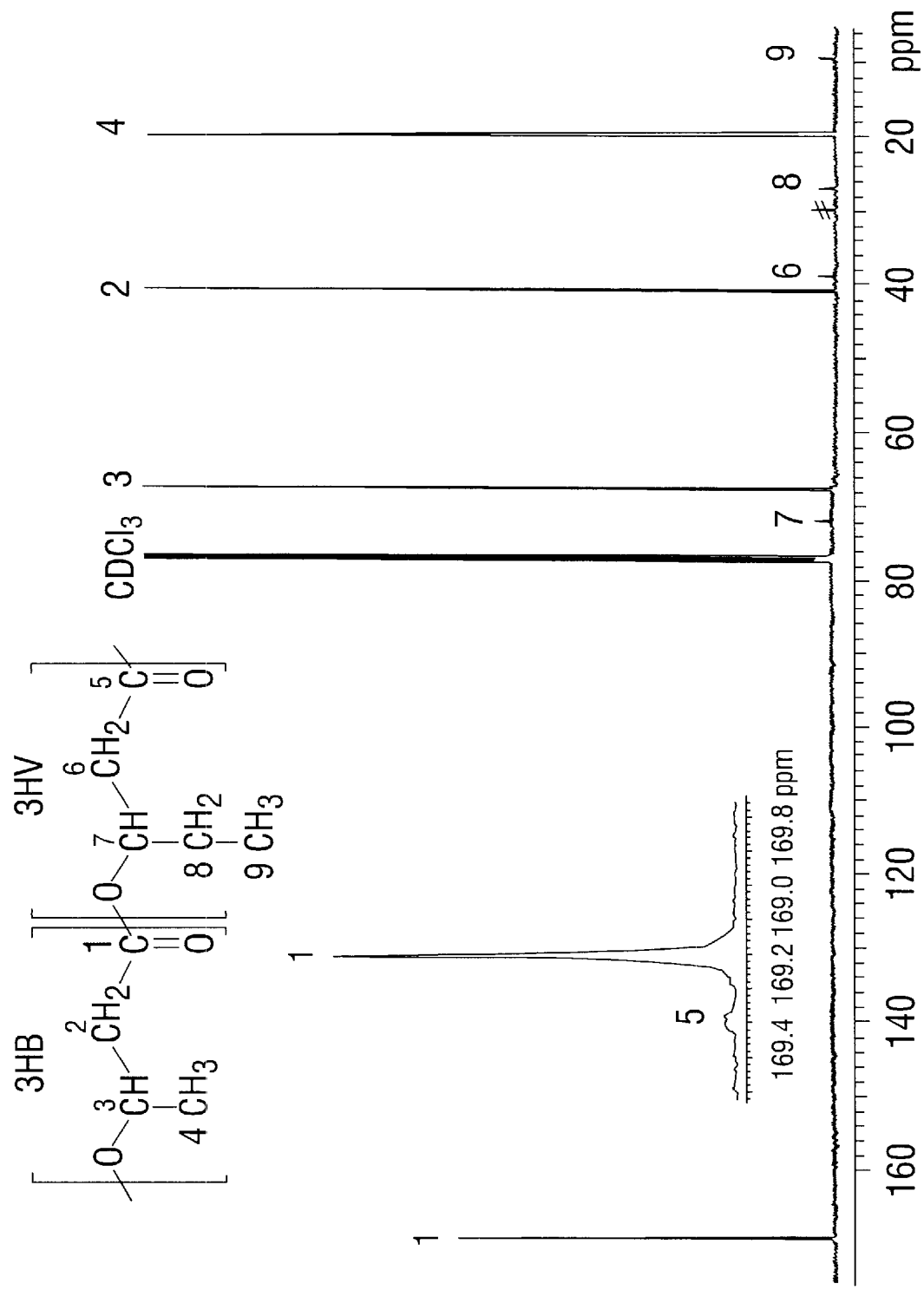
FIG. 37: $^{13}C$ NMR spectra demonstrating poly(β-hydroxybutyrate-co-β-hydroxyvalerate) copolymer production in transgenic Arabidopsis. Note the presence of signals indicating presence of both 3-hydroxybutyrate and 3-hydroxyvalerate side chains.

Once propionyl-CoA has been produced, the pathway is identical to that shown to produce PHBV copolymer in recombinant *E. coli* (Slater, S., et al. *J. Bacteriol.* 180: 1979–1987, 1998). Propionyl-CoA is converted to D-β-hydroxyvaleryl-CoA by BktB and PhbB, and then is polymerized with D-β-hydroxybutyryl-CoA to form PHBV copolymer. The functionality of the entire pathway in plants is shown in FIG. 37, which shows $^1$H-NMR spectra demonstrating the presence of PHBV copolymer in Arabidopsis. We also obtained $^{13}$C-NMR demonstrating PHBV copolymer production in Brassica, and all these data have been corroborated by coupled gas chromatography-mass spectrometry (data not shown). The molecular weight of PHBV isolated from Brassica seeds was approximately 1×10$^6$, with a polydispersity index of 2.4. These parameters are suitable for commercial applications.

Figure 38:
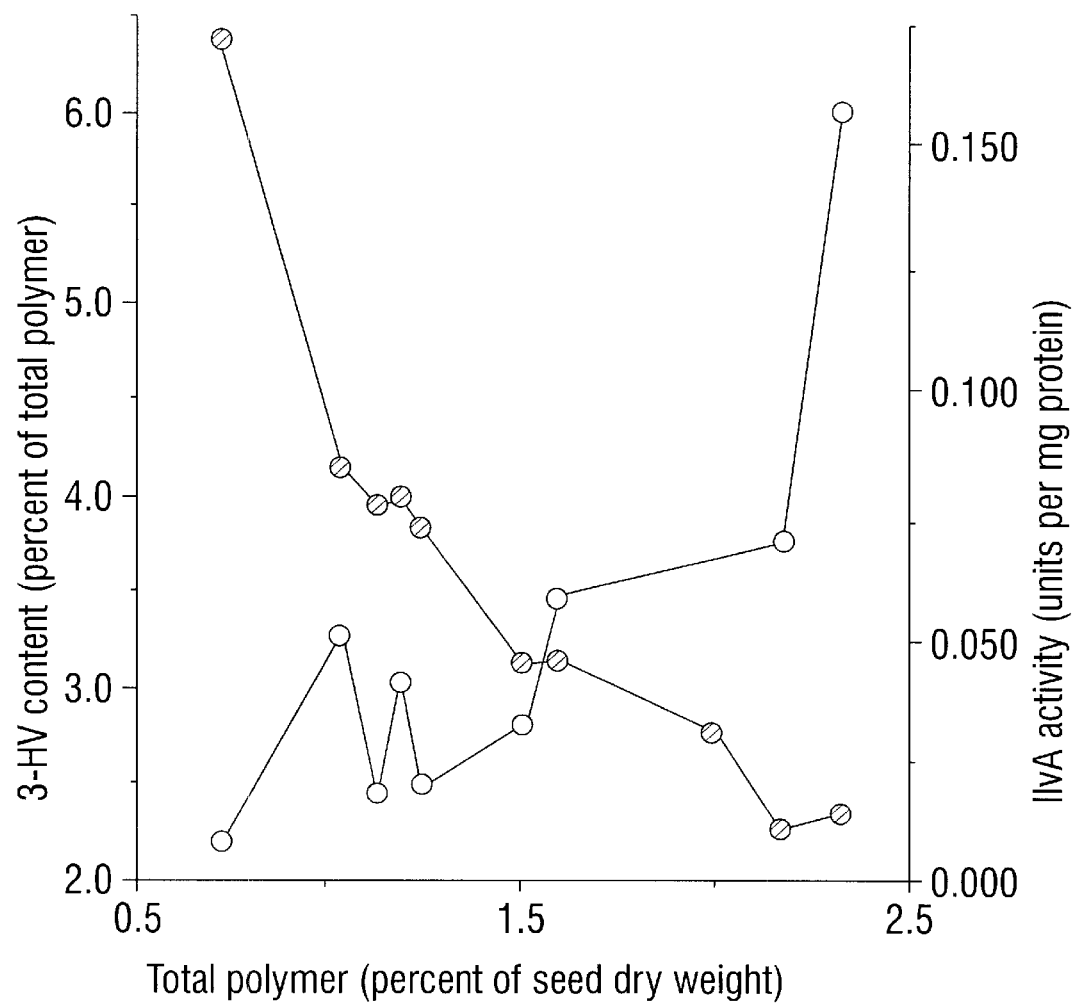
FIG. 38: Analyses of total polymer production, the 3-hydroxyvalerate fraction of the polymer, and the activity of threonine deaminase Brassica oilseeds synthesizing PHBV copolymer. Note the distinct negative correlation between polymer concentration and the 3-HV content of the polymer. Also note that increasing threonine deaminase activity does not lead to increased 3-HV content.

Although copolymer was made in both Arabidopsis and Brassica, the 3-hydroxyvalerate component varied with the in vivo polymer concentration. The polymer composition in Brassica seeds distinctly showed a negative correlation between the 3-hydroxyvalerate content of the polymer and total polymer production (FIG. 38). Threonine deaminase activity also negatively correlated with 3-HV content (FIG. 38), a somewhat surprising result considering the role of IlvA in the production of 3-HV. However, we have consistently found that introduction of vectors encoding multiple genes leads to a general, concerted expression of all encoded enzymes. Thus, elevated IlvA activity is consistent with elevated polymer production.

Discussion

The use of green plants as industrial factories will often require significant changes in plant metabolism, so metabolic engineering of multi-step pathways will become an important technology in "green chemistry" efforts. In this study, production of the PHA copolymer PHBV has been accomplished using a combination of endogenous and transgene-encoded enzymes. The pathway consists of five separate enzymes, four being encoded as transgenes. In the case of Brassica, all four genes were successfully introduced on a single vector.

Commercial application of this technology will rest on two primary metabolic issues: 1) can polymer be produced in planta to concentrations amenable to economical polymer extraction? and 2) as the polymer concentration increases, can the appropriate monomer composition be maintained? We expect that polymer concentrations in planta will need to reach at least 15% of dry weight for economical production to be feasible. PHB homopolymer concentrations near 15% have been reported (Nawrath, C. et al. *Proc. Natl. Acad. Sci.* 91: 12760–12764, 1994) and have also been achieved in our laboratory (data not shown). Thus, high-level PHB production appears technically attainable.

Production of PHBV copolymer has been accomplished in this study, although all plants produced copolymer at levels below 3% of plant tissue dry weight. The next challenge is high-level production of copolymer, and the data in FIG. 38 show that additional work is required to maintain the 3-hydroxyvalerate composition at high polymer concentrations. Specifically, as polymer production increased, the 3-hydroxyvalerate fraction of the polymer decreased, and increasing threonine deaminase expression did not effect this correlation. These data suggest a metabolic bottleneck in the provision of 3-hydroxyvalerate to PHA synthase. The BktB, PhbB, PhbC pathway efficiently synthesizes PHBV copolymer (Slater, S., et al. *J. Bacteriol.* 180: 1979–1987, 1998), and production of 2-ketobutyrate in planta is efficient, as estimated from the elevated levels of 2-ketobutyrate, 2-aminobutyrate and isoleucine (FIG. 36). Thus, the metabolic bottleneck must exist at the conversion of 2-ketobutyrate to propionyl-CoA by the pyruvate dehydrogenase complex. As noted above, the PDC strongly prefers pyruvate as a substrate, and this difference is compounded in vivo by the concentration ratio of pyruvate to 2-ketobutyrate (FIG. 36). Pyruvate dehydrogenase apparently cannot effectively compete for 2-ketobutyrate so propionyl-CoA synthesis is limited.

Production of copolymer to high internal concentrations may require a supplementary route for conversion of 2-ketobutyrate to propionyl-CoA. There are several ways to bypass the PDC or supplement its activity, but all will require additional transgenes. These routes include modifying the α-ketoacid dehydrogenase to more readily accept propionyl-CoA (Inoue H, et al. *J Bacteriol.* 179: 3956–3962, 1997; Gruys et al WO 98/00557), expression of an alternative enzyme complex capable of forming propionyl-CoA from 2-ketobutyrate (Kerscher, L. and Oesterhelt, D., *Eur. J. Biochem.* 116: 587–594, 1981), or co-expression of a propionyl-CoA dehydrogenase (Horswill et al; Mitsky et al., unpublished data) with a propionyl-CoA synthetase or CoA transferase (Gruys et al WO 98/00557; Valentin et al, manuscript in preparation). Thus, a commercially viable transgenic plant producing PHA polymer from threonine may contain up to six separate transgenes.

Figure 39:
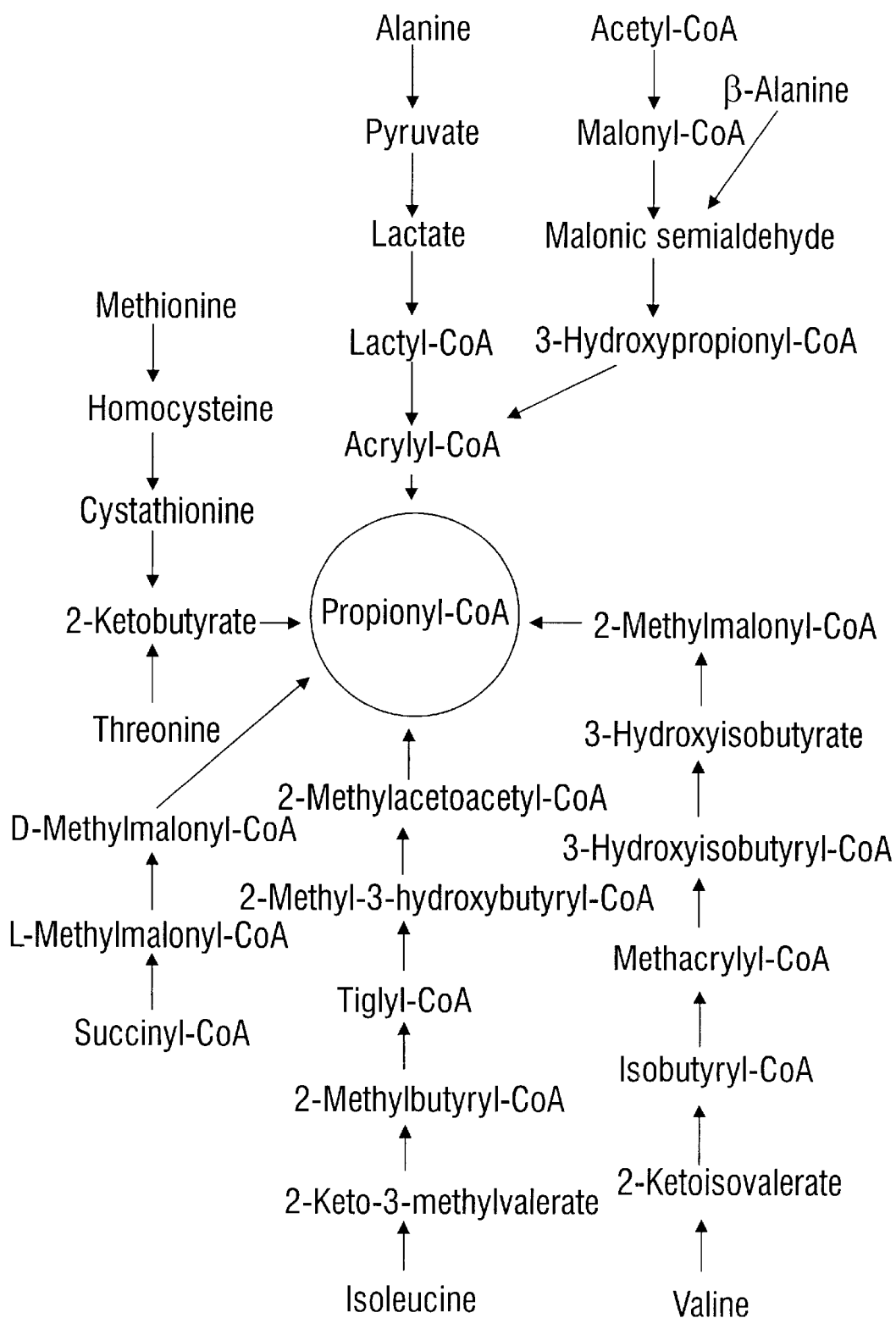
FIG. 39: Multiple potential routes to produce propionyl-CoA in planta. Most alternative pathways have the potential to produce propionyl-CoA in plants. However, production of propionyl-CoA from threonine provides the most direct route.

Synthesis of propionyl-CoA can also be achieved through other metabolic pathways, although none presents a straightforward alternative to the threonine derived pathway (FIG. 39). For instance, propionyl-CoA may be generated from acetyl-CoA using a 5-step pathway, part of which is involved in propionyl-CoA degradation in plants (Goodwin, T. W. and Mercer, E. I. Introduction to Plant Biochemistry. Second Edition. Pergamon Press, Oxford, 1985; Eisenreich, W., et al. *Eur. J. Biochem.* 215: 619–632, 1993; Preifert, H., and Steinbüchel, A. *J. Bacteriol.* 174: 6590–6599, 1992; Podkowinski, J., et al. *Proc. Natl. Acad Sci. USA* 93: 1870–1874, 1996; Sun, J., et al. *Plant Physiol.* 115: 1371–1383, 1997; Horswill A. R., and Escalante-Semerena J. C. *J. Bacteriol.* 179: 928–940, 1997; Gruys et al, unpublished data). Conversion of acrylyl-CoA to propionyl-CoA is potentially problematic, but an appropriate enzyme may be available from *Chroroflexus aurantiacus* (Eisenreich, W., et al. *Eur. J. Biochem.* 215: 619–632, 1993). Propionyl-CoA can also be derived from succinyl-CoA using a pathway present in both *Rhodococcus ruber* and *Nocardia corallina* (Williams, D. R.,et al. *Appl. Microbiol. Biotechnol.* 40: 717–723, 1994; Valentin, H. E., and Dennis, D. *Appl. Environ. Microbiol.* 62: 372–379,.1996). This pathway is initiated by methylmalonyl-CoA mutase, an enzyme that requires vitamin $B_{12}$ as a cofactor. However, vitamin $B_{12}$ is not synthesized in plants (Goodwin, T. W. and Mercer, E. I. Introduction to Plant Biochemistry. Second Edition. Pergamon Press, Oxford, 1985). Rhodococcus and Nocardia also produce minor amounts of 3-hydroxyvaleryl-CoA via a different, uncharacterized route. This route may be a link to amino acid metabolism, such as the pathways used by other bacteria and animals to degrade valine and isoleucine (FIG. 39). These pathways might also be engineered in plants, but a large number of genes are required.

Several other amino acids can be used to produce propionyl-CoA. Methionine, like threonine, generates 2-ketobutyrate during catabolism. This conversion is catalyzed by L-methionine γ-lyase in a reaction that also produces ammonia and methanethiol (Tanaka, H., et al. *Enzyme Microb. Technol.* 7: 530–537, 1985). The effect of methanethiol production on plants is unknown, and supplementation of PDC activity would still be required to efficiently produce propionyl-CoA. Another pathway, present in *Clostridium propionicum,* converts alanine to propionyl-CoA via lactic acid, lactyl-CoA and acrylyl-CoA (Schweiger, G., and Buckel, W. *FEBS Lett.* 171: 79–84, 1984; Cardon, B. P., and Barker, H. A. *Arch. Biochem. Biophys.* 12: 165–180, 1947). However, none of the required genes has been cloned, and some of the necessary enzymes are oxygen sensitive (Hofmeister, A. E. M., and Buckel, W. *Eur. J. Biochem.* 206: 547–552, 1992; Kuchta, R. D., and Abeles, R. H. *J. Biol. Chem.* 260: 13181–13189, 1985). β-alanine is another potential starting metabolite for the production of propionyl-CoA (Arst, H. N. Jr. *Mol. Gen. Genet.* 163: 23–27, 1978; Roberts, E., and Bregoff, H. M. *J. Biol. Chem.* 201: 393–398, 1953; Kupiecki, R. P., and Coon, M. J. *J. Biol. Chem.* 229: 743–754, 1957). β-alanine normally plays a critical role as a precursor to Coenzyme-A and acyl carrier protein. However, little is known about the concentration and compartmentalization of β-alanine in plants, and propionyl-CoA may actually be required for its synthesis.

In summary, poly(β-hydroxybutyrate-co-β-hydroxyvalerate) copolymer was produced in both Arabidopsis and Brassica by simultaneously accessing amino acid and short-chain fatty acid metabolite pools. In Brassica, all four required transgenes were introduced on a single vector, eliminating the plant crossing normally necessary to assemble a pathway of this size. The polymer molecular mass was adequate for commercial purposes, but an apparent metabolic bottleneck in conversion of 2-ketobutyrate to propionyl-CoA suggests that additional engineering may be required to achieve high-level production of polymer with the necessary β-hydroxyvalerate composition.

Generation of ilvA Mutants

All ilvA alleles used herein are derived from the *E. coli* ilvA gene (Lawther, R. P. et al., *Nucl. Acids Res.* 11: 2137–2155, 1987) that is harbored in pMON25659 (Gruys et al WO 98/00557). The ilvA219 mutation (Eisenstein, E., et al. *Biochemistry.* 34: 9403–9412, 1995) and ilvA466 mutation (Taillon, B. E., et al. *Gene.* 63: 245–252, 1988), both originally isolated in *Salmonella typhimurium,* were introduced into the *E. coli* gene by oligonucleotide-directed mutagenesis as previously described (Gruys et al. WO 98/00557).

Plasmid Construction and Transformation of *Arabidopsis thaliana* and *Brassica napus*

All transformation vectors are derived from pMON10098, a vector designed for Agrobacterium-mediated transformation of plants that encodes the nptII selectable marker. The trfa function is provided in trans by the host bacterium, *Agrobacterium tumefaciens* ABI. *A. tumefaciens* ABI is Agrobacterium strain GV3101 (Van Larebeke, N., et al. *Nature.* 252: 169–170, 1974) harboring the helper plasmid pMP90RK (Koncz, C., and Schell, *J. Mol. Gen. Genet.* 204: 383–396, 1986).

All PHA production genes used in this study were initially constructed in intermediate vectors as cassettes including a promoter, a chloroplast transit peptide fused to the gene of interest, and a 3' control region. In every case, the gene cassette is flanked by Not I restriction sites, plus several additional unique restriction sites. Each cassette was excised from it's intermediate vector using appropriate restriction enzymes, and sequentially ligated into the recombinant vector for plant transformation.

For metabolite analysis, Arabidopsis was transformed with either pMON15715, an ilvA-negative control vector, or pMON25668, which expresses both phbA and wild-type ilvA from, e35S promoters.

For production of PHBV in Arabidopsis, two separate plasmids were used.

The first vector encoded both phbB and phbC (pMON25678), and the second vector encoded both bktB and ilvA (pMON25812). All genes were controlled by the e35S promoter (Odell. J. T., et al. *Nature.* 313: 810–812, 1995) and the E9 3' region (Coruzzi, G., et al. *EMBO J.* 3: 1671–1679, 1984). All enzymes were fused to the Arabidopsis RuBisCo small subunit 1a transit peptide that was previously used for PHB production (Nawrath, C., et al. *Proc. Natl. Acad. Sci.* 91: 12760–12764, 1994). Plasmid pMON25678 encodes resistance to glyphosate, whereas pMON25812 encodes resistance to kanamycin. Both plasmids were simultaneously used for Agrobacterium-mediated Arabidopsis transformation (Bechtold N., et al. *Comptes Rendus Acad Sci. Paris Sciences Serie III Sciences de la Vie.* 316: 1194–1199, 1993), and transformants were selected on both glyphosate and kanamycin as follows.

*Arabidopsis thaliana* Columbia plants were grown in Metro Mix 200 in 2.5 in. pots covered with a mesh screen. Sown seed was vernalized for 5 days and germinated under conditions of 16 hours light/8 hours dark at 20° C. to 22° C., 75% humidity. Plants were watered and fertilized twice weekly with 1/2X Peters 20-20-20 until infiltration.

A 1:50 dilution of an overnight culture of Agrobacterium tumefaciens ABI strain was grown at 28° C. in YEP containing Spectinomycin 100 mg/L, Streptomycin, 100 mg/L, Chloramphenicol 25 mg/L, and Kanamycin 50 mg/L. Each culture contained a different ABI construct. After 16–20 hours the Agrobacterium cultures were concentrated by centrifugation. The supernatant was discarded and the cell pellets were dried and resuspended in infiltration medium (MS Basal Salts 0.5%, Gamborg's B-5 Vitamins 1%, Sucrose 5%, MES 0.5 g/L, pH 5.7) with 0.44 nM benzylaminopurine (10 µL of a 1.0 mg/L stock in DMSO per liter) and 0.02% Silwet L-77 to an $OD_{600}$ of 0.8. For co-infiltrations each culture was resuspended as described above and 150 mL each of two cultures were combined for a total of 300 mL.

Plants were soaked in water 30 minutes prior to infiltration. Inverted plants were placed into the cultures and vacuum infiltrated at 27 in. Hg for 10 minutes. The plants were placed on their sides in a diaper-lined tray and covered with a germination dome for one day. The pots were then turned upright and were not watered for five days. Infiltrated plants were grown to maturity as described above. Ripe seeds were harvested and sterilized. Harvested seed was placed in a 15 mL Corning tube and sterilized. The tubes containing seed were placed on their sides with lids loosened in a vacuum dessicator containing a beaker of Clorox and 1:100 hydrochloric acid. The dessicator was then sealed with a vacuum and the seed remained in the dessicator overnight. Sterilized seeds from co-infiltrated plants were placed on media containing MS Basal Salts 4.3 g/L, Gamborg's B-5 (500 X) 2.0 g/L, glucose 10 g/L, MES 0.5 g/L, and 8 g/L phytagar with carbenicillin 250 mg/L, cefotaxime 100 mg/L, kanamycin 60 mg/L and 4 mM glyphosate. The seed was germinated at 26° C., 20 hours light/4 hours dark. Transformants were transferred to soil and covered with a germination dome for one week. The plants were grown in plant growth conditions described above.

Figure 3:
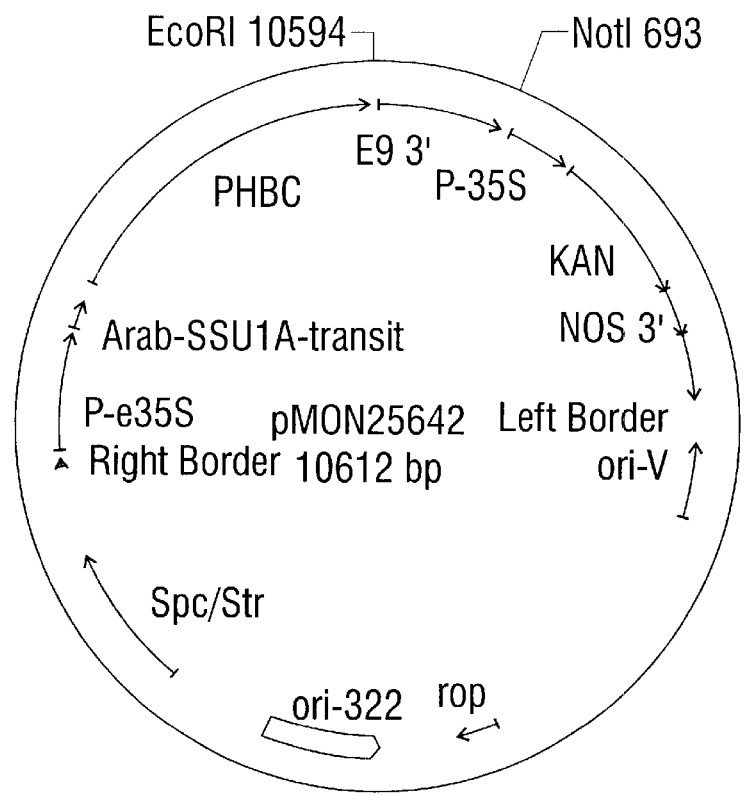
FIG. 3: Plasmid map of pMON25642. A list of the restriction enzyme cutting sites for pMON25642 is provided in Table 10.

For transformation of *Brassica napus*, a single vector encoding the entire PHBV biosynthesis pathway was used. This vector, pMON36824, encodes bktB, phbB, phbC, and ilvA466 (FIG. 3). As with the Arabidopsis vectors, each gene of interest was fused to a chloroplast transit peptide, so each protein is transported to the seed leukoplast. All enzymes were fused to the Arabidopsis RuBisCo small subunit 1a transit peptide that was previously used for PHB production (Nawrath, C. et al. *Proc. Natl. Acad. Sci.* 91: 12760–12764, 1994), except PhbB was fused to the transit peptide from pea RuBisCo small subunit (Cashmore, A. R. Nuclear genes encoding the small subunit of ribulose-1,5-bisphosphate carboxylase. pp. 29–38 in Genetic Engineering of Plants, Kosuge, T., Meredith, C. P., Hollaender, A. (eds.). Plenum, New York, 1983). Each gene is controlled by the promoter from the fatty acid hydroxylase gene of Lesquerella (P-Lh; Broun, P., et al. *Plant J.* 13: 201–210, 1998), and the E9 3' region (Coruzzi, G., et al. *EMBO J.* 3: 1671–1679, 1984). P-Lh directs expression of these genes within the developing seed. Transformation of Brassica was performed as described by Fry et al. (*Plant Cell Rep.* 6: 321–325, 1987), and transformants were selected on glyphosate.

Isolation of Brassica Seed Leukoplasts and Analysis of Pyruvate Dehydrogenase Complex Activity Leukoplasts were isolated essentially as described by Kang and Rawsthorne (*Plant J.* 6: 795–805, 1994). Isolated leucoplasts were lysed by sonication and debris removed by centrifugation at 10,000×g for 10 minutes. The crude extract was desalted using Pharmacia NAβ-5 columns and the protein concentrations determined by the Bradford method (Bradford, M. *Anal. Biochem.* 72: 248–254, 1976). Five to 50 µL were added to assay mix which contained final concentrations of: 100 mM EPPS, pH 8.0; 5 mM $MgCl_2$; 2.4 mM coenzyme-A; 1.5 mM $NAD^-$; and 0.2 mM TPP (cocarboxylase). The reaction was initiated with addition of either pyruvate or 2-ketobutyrate substrates to final concentrations of 1.5 mM and 30 mM, respectively. To aid in analysis and ensure peak identities, $^{14}C$ labeled pyruvate and 2-ketobutyrate were spiked into both substrates. The reactions were quenched with 30 µL of 10% formic acid after 2 to 30 minutes. 100 µL of the reaction was injected onto a Beckman Ultrasphere HPLC column (5 µM, 4.6 mm×15 cm) and eluted with 1 mL/minute gradient of solvent A (50 mM ammonium acetate buffer pH 6.0 containing 5% acetonitrile) going from 0 to 40% solvent B (acetonitrile) in 15 minutes. The reaction was followed by monitoring absorbance of CoA-derived products at 230 and 260 nm using a photo-diode array detector. Use of radioisotope flow detector allowed confirmation of both substrate and product peak identities. The percent conversion of added substrates was used to determine the specific activities of the extracts. One unit equals one nmol product produced per minute per mg protein in extract.

Amino Acid and 2-ketoacid Analysis

Amino Acid analysis was performed by Dr. Donald Willis at Ralston Analytical Laboratories, essentially as described by Willis (*J. Chromatog.* 408: 217–225, 1987).

Extraction and Gas Chromatography Analysis of Polymer from Arabidopsis

For isolation of polymer from Arabidopsis, stems and leaves were harvested and dehydrated by lyophilization for approximately 36 hours. The material was ground to a fine powder, and 100 mg of powder was treated with 10 mL Clorox bleach for 1 hour with shaking at room temperature. The extract was subjected to centrifugation at 1,600×g for ten minutes, and the supernatant solutions was carefully removed. Ten mL 100% methanol were added, the solution was mixed by vortex, and then centrifuged again. After a second, identical, methanol extraction, the material was allowed to dry overnight. Polymer was extracted from the dried material with 1 mL of chloroform containing 3 µmol/mL methyl-benzoate standard and 1 mL of methanol/sulphuric acid (85:15, v/v). The tube was heated to 100° C. for exactly 2.5 hours, and the solid material was removed by centrifugation. The solution was cooled, 1 mL water was added, and the liquid was mixed using a vortex mixer. The organic and aqueous phases were separated by centrifugation at 1,600×g for ten minutes. The chloroform layer was transferred to a clean test tube and vigorously mixed with approximately 200 mg of silica gel. Solid material was removed by centrifugation, and the supernatant material was subjected to gas chromatography. Gas chromatographic characterization of the methyl-ester residues was performed as described by Slater et al. (*J. Bacteriol.* 180: 1979–1987, 1998), except that the temperature gradient was performed as follows. The initial temperature of 70° C. was held for 6 minutes, then the temperature was increased by 30° C. per minute to 130° C. Finally, the temperature was increased by 50° C. per minute to 300° C. and held at 300° C. for 5 minutes.

Extraction and Gas Chromatography Analysis of Polymer from Brassica Seeds

For isolation of polymer from canola seed, seeds were ground to a fine powder with a mortar and pestle. Approximately 200 mg of each sample were extracted two times in a glass tube with 10 mL each of hexane for 1 hour at 60° C., then two times with 10 mL each of 100% methanol for one hour at 60° C. This procedure removes oil from the seed. The material was allowed to dry to completion overnight. Polymer was extracted from the dried material with 1 mL of chloroform containing 3 μmol/mL methyl-benzoate standard. The tube was heated to 100° C. for 5 hours and the samples were cooled. One mL methanol/sulphuric acid (85:15, v/v) was added, and the mixture was heated to 100° C. for exactly 2.5 hours. The solution was cooled, extracted with water and subjected to gas chromatography as described above.

Characterization of Polymer by Nuclear Magnetic Resonance Spectroscopy and Gel Permeation Chromatography Nuclear magnetic resonance (NMR) studies were done using a Varian Unity 500 MHz spectrometer. Proton spectra were obtained on a Varian pfg 5 mm probe at 30° C. from PHA samples of approximately 20 mg dissolved in 1 mL deuterochloroform. Acquisitions were taken at a 90° pulse, 2.3 s acquisition time, 30 s delay, collecting 65 k data points and 16 accumulations. Chemical shifts were referenced to $CHCl_3$ ($\delta$=7.24 ppm). The 13C{1H} spectra (125 MHz) were taken at 30° C. on a Nalorac 3 mm $^{13}C$ probe containing a solution of approximately 10 mg PHA in 200 μL deuterochloroform. The spectra were obtained using 30° pulses, 1.5 s acquisition time, zero delay, 131 k data points and 55,296 accumulations. Chemical shifts were measured relative to $CHCl_3$ ($\delta$=77.0 ppm).

Gel permeation chromatography was performed according to Koizumi et al. (*J. M. S. Pure Appl. Chem.* A32: 759–774, 1995).

Example 13
Plant Promoters

Plant promoter sequences can be constitutive or inducible, environmentally- or developmentally-regulated, or cell- or tissue-specific. Often-used constitutive promoters include the CaMV 35S promoter (Odell et al., *Nature* 313: 810–812, 1985), the enhanced CaMV 35S promoter, the Figwort Mosaic Virus (FMV) promoter (Richins, R. D. et al., *Nucleic Acids Res.* 20: 8451–8466, 1987), the mannopine synthase (mas) promoter, the nopaline synthase (nos) promoter, and the octopine synthase (ocs) promoter. Useful inducible promoters include promoters induced by salicylic acid or polyacrylic acids (PR-1, Williams, S. W. et al, *Biotechnology* 10: 540–543, 1992), induced by application of safeners (substituted benzenesulfonamide herbicides, Hershey, H. P. and Stoner, T. D., *Plant Mol. Biol.* 17: 679–690, 1991), heat-shock promoters (Ou-Lee et al., *Proc. Natl. Acad. Sci. U.S.A.* 83: 6815–6819, 1986; Ainley, W. M. et al., *Plant Mol. Biol.* 14: 949–967, 1990), a nitrate-inducible promoter derived from the spinach nitrite reductase gene (Back, E. et al., *Plant Mol. Biol.* 17: 9–18, 1991), hormone-inducible promoters (Yamaguchi-Shinozaki, K. et al., *Plant Mol. Biol.* 15: 905–912, 1990; Kares et al., *Plant Mol. Biol.* 15: 905–912, 1990), and light-inducible promoters associated with the small subunit of RuBP carboxylase and LHCP gene families (Kuhlemeier et al., *Plant Cell* 1: 471–478, 1989; Feinbaum, R. L. et al., *Mol. Gen. Genet.* 226: 449–456, 1991; Weisshaar, B. et al., *EMBO J.* 10: 1777–1786, 1991; Lam, E. and Chua, N. H., *J. Biol. Chem.* 266: 17131–17135, 1990; Castresana, C. et al., *EMBO J.* 7: 1929–1936, 1988; Schulze-Lefert, P. et al., *EMBO J.* 8: 651–656, 1989). Examples of useful tissue-specific, developmentally-regulated promoters include the β-conglycinin 7S promoter (Doyle, J. J. et al., *J. Biol. Chem.* 261: 9228–9238, 1986; Slighton and Beachy, *Planta* 172: 356, 1987), and seed-specific promoters (Knutzon, D. S. et al., *Proc. Natl. Acad. Sci. U.S.A.* 89: 2624–2628, 1992; Bustos, M. M. et al., *EMBO J.* 10: 1469–1479,.1991; Lam, E. and Chua, N. H., *Science* 248: 471–474, 1991; Stayton et al., *Aust. J. Plant. Physiol.* 18: 507, 1991). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al., *Seed Sci. Res.* 1: 209–219, 1991), phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Comai, L. and Moran, P. M., U.S. Pat. No. 5,106,739, issued Apr. 21, 1992), or to combine desired transcriptional activity and tissue specificity.

Example 14
Plant Transformation and Regeneration

A variety of different methods can be employed to introduce such vectors into plant protoplasts, cells, callus tissue, leaf discs, meristems, etcetera, to generate transgenic plants, including Agrobacterium-mediated transformation, particle gun delivery, microinjection, electroporation, polyethylene glycol mediated protoplast transformation, liposome-mediated transformation, etc. (reviewed in Potrykus, *Ann. Rev. Plant Physiol. Plant Mol. Biol.* 42: 205–225, 1991). In general, transgenic plants comprising cells containing and expressing DNAs encoding enzymes facilitating PHA biosynthesis can be produced by transforming plant cells with a DNA construct as described above via any of the foregoing methods; selecting plant cells that have been transformed on a selective medium; regenerating plant cells that have been transformed to produce differentiated plants; and selecting a transformed plant which expresses the enzyme-encoding nucleotide sequence.

Specific methods for transforming a wide variety of dicots and obtaining transgenic plants are well documented in the literature (Gasser and Fraley, *Science* 244: 1293–1299, 1989; Fisk and Dandekar, *Scientia Horticulturae* 55: 5–36, 1993; Christou, *Agro Food Industry Hi Tech, p.*17 (1994); and the references cited therein).

Successful transformation and plant regeneration have been reported in the monocots as follows: asparagus (*Asparagus officinalis;* Bytebier et al., *Proc. Natl. Acad. Sci. U.S.A.* 84: 5345–5349, 1987); barley (*Hordeum vulgarae;* Wan and Lemaux, *Plant Physiol.* 104: 37–48, 1994); maize (*Zea mays;* Rhodes, C. A. et al., *Science* 240: 204–207, 1988; Gordon-Kamm et al., *Plant Cell* 2: 603–618, 1990; Fromm, M. E. et al., *Bio/Technology* 8: 833–839, 1990; Koziel et al., *Bio/Technology* 11: 194–200, 1993); oats (*Avena sativa;* Somers et al., *Bio/Technology* 10: 1589–1594, 1992); orchardgrass (*Dactylis glomerata;* Horn et al., *Plant Cell Rep.* 7: 469–472, 1988); rice (*Oryza sativa,* including indica and japonica varieties; Toriyama et al., *Bio/Technology* 6: 10, 1988; Zhang et al., *Plant Cell Rep.* 7: 379–384, 1988; Luo and Wu, *Plant Mol. Biol. Rep.* 6: 165, 1988; Zhang and Wu, *Theor. Appl. Genet.* 76: 835, 1988; Christou et al., *Bio/Technology* 9: 957–962, 1991); rye (*Secale cereale;* De la Pena et al., *Nature* 325: 274–276, 1987); sorghum (*Sorghum bicolor;* Casas, A. M. et al., *Proc. Natl. Acad. Sci. U.S.A.* 90: 11212–11216, 1993); sugar cane (*Saccharum* spp.; Bower and Birch, *Plant J.* 2: 409–416, 1992); tall fescue (*Festuca arundinacea;* Wang, Z. Y. et al., *Bio/Technology* 10: 691–696, 1992); turfgrass (*Agrostis palustris;* Zhong et al., *Plant Cell Rep.* 13: 1–6, 1993); wheat (*Triticum aestivum;* Vasil et al., *Bio/Technology* 10: 667–674, 1992; Weeks, T. et al., *Plant Physiol.* 102:

1077–1084, 1993; Becker et al., *Plant J*. 5: 299–307, 1994), and alfalfa (Masoud, S. A. et al., *Transgen. Res*. 5: 313, 1996).

Example 15
Host Plants

Particularly useful plants for polyhydroxyalkanoate production include those that produce carbon substrates which can be employed for polyhydroxyalkanoate biosynthesis, including tobacco, wheat, potato, Arabidopsis, and high oil seed plants such as corn, soybean, canola, oil seed rape, sunflower, flax, peanut, sugarcane, switchgrass, and alfalfa.

If the host plant of choice does not produce the requisite fatty acid substrates in sufficient quantities, it can be modified, for example by mutagenesis or genetic transformation, to block or modulate the glycerol ester and fatty acid biosynthesis or degradation pathways so that it accumulates the appropriate substrates for polyhydroxyalkanoate production. Expression of enzymes such as acyl-ACP thioesterase, fatty acyl hydroxylase, and yeast MFP may serve to increase the flux of substrates in the peroxysome, leading to higher levels of polyhydroxyalkanoate biosynthesis.

Example 16
Nucleic Acid Mutation and Hybridization

Variations in the nucleic acid sequence encoding a fusion protein may lead to mutant protein sequences that display equivalent or superior enzymatic characteristics when compared to the sequences disclosed herein. This invention accordingly encompasses nucleic acid sequences which are similar to the sequences disclosed herein, protein sequences which are similar to the sequences disclosed herein, and the nucleic acid sequences that encode them. Mutations may include deletions, insertions, truncations, substitutions, fusions, and the like.

Mutations to a nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a nucleic acid sequence. Examples include single strand rescue (Kunkel, T. *Proc. Natl. Acad. Sci. U.S.A.*, 82: 488–492, 1985), unique site elimination (Deng and Nickloff, *Anal. Biochem*. 200: 81, 1992), nick protection (Vandeyar, et al. *Gene* 65: 129–133. 1988), and PCR (Costa, et al. *Methods Mol. Biol*. 57: 31–44, 1996). Random or non-specific mutations may be generated by chemical agents (for a general review, see Singer and Kusmierek, *Ann. Rev. Biochem*. 52: 655–693, 1982) such as nitrosoguanidine (Cerda-Olmedo et al., *J. Mol. Biol*. 33: 705–719, 1968; Guerola, et al. *Nature New Biol*. 230: 122–125, 1971) and 2-aminopurine (Rogan and Bessman, *J. Bacteriol*. 103: 622–633, 1970), or by biological methods such as passage through mutator strains (Greener et al. *Mol. Biotechnol*. 7: 189–195, 1997).

Nucleic acid hybridization is a technique well known to those of skill in the art of DNA manipulation. The hybridization properties of a given pair of nucleic acids is an indication of their similarity or identity. Mutated nucleic acid sequences may be selected for their similarity to the disclosed nucleic acid sequences on the basis of their hybridization to the disclosed sequences. Low stringency conditions may be used to select sequences with multiple mutations. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed sequences. Conditions employed may include about 0.02 M to about 0.15 M sodium chloride, about 0.5% to about 5% casein, about 0.02% SDS and/or about 0.1% N-laurylsarcosine, about 0.001 M to about 0.03 M sodium citrate, at temperatures between about 50° C. and about 70° C. More preferably, high stringency conditions are 0.02 M sodium chloride, 0.5% casein, 0.02% SDS, 0.001 M sodium citrate, at a temperature of 50° C.

Example 17
Determination of Homologous and Degenerate Nucleic Acid Sequences Modification and changes may be made in the sequence of the proteins of the present invention and the nucleic acid segments which encode them and still obtain a functional molecule that encodes a protein with desirable properties. The following is a discussion based upon changing the amino acid sequence of a protein to create an equivalent, or possibly an improved, second-generation molecule. The amino acid changes may be achieved by changing the codons of the nucleic acid sequence, according to the codons given in Table 9.

TABLE 9

Codon degeneracies of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |

TABLE 9-continued

Codon degeneracies of amino acids

| Amino acid | One letter | Three letter | Codons |
|---|---|---|---|
| Valine | V | Val | GTA GTC GTG GTT |
| Tryptophan | W | Trp | TGG |
| Tyrosine | Y | Tyr | TAC TAT |

Certain amino acids may be substituted for other amino acids in a protein sequence without appreciable loss of enzymatic activity. It is thus contemplated that various changes may be made in the peptide sequences of the disclosed protein sequences, or their corresponding nucleic acid sequences without appreciable loss of the biological activity.

In making such changes, the hydropathic index of amino acids may be considered. The importance of the hydropathic amino acid index in conferring interactive biological function on a protein is generally understood in the art (Kyte and Doolittle, J. Mol. Biol., 157: 105–132, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics. These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 (Hopp, T. P., issued Nov. 19, 1985) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0 ±1); serine (+0.3); asparagine/glutamine (+0.2); glycine (0); threonine (−0.4); proline (−0.5 ±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted in functional fusion proteins.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

TABLE 10

RESTRICTION SITES FROM FIG. 3

| ENZYME | CUT SITE |
|---|---|
| NotI | 693 |
| XhoI | 702 |
| BsaAI | 1510 |
| RsrII | 1722 |
| XhoI | 2170 |
| DraI | 2817 |
| BsaAI | 4975 |
| DraI | 5980 |
| DraI | 5999 |
| BsaAI | 7195 |
| DraI | 7677 |
| DraI | 7754 |
| BglII | 8440 |
| RsrII | 8998 |
| BglII | 9296 |
| AscI | 9851 |
| SexAI | 9917 |
| BsaAI | 9933 |
| SfiI | 10387 |
| SbfI | 10535 |
| EcoRI | 10594 |

TABLE 11

RESTRICTION SITES FROM FIG. 4

| ENZYME | CUT SITE |
|---|---|
| NotI | 678 |
| XhoI | 687 |

TABLE 11-continued

RESTRICTION SITES FROM FIG. 4

| ENZYME | CUT SITE |
| --- | --- |
| BsaAl | 1497 |
| Rsrll | 1709 |
| Xhol | 2157 |
| Dral | 2804 |
| BsaAl | 4924 |
| Dral | 5929 |
| Dral | 5948 |
| BsaAl | 7144 |
| Dral | 7626 |
| Dral | 7703 |
| Bglll | 8389 |
| EcoRl | 8413 |

TABLE 12

RESTRICTION SITES FROM FIG. 5

| ENZYME | CUT SITE |
| --- | --- |
| BsaAl | 411 |
| Notl | 878 |
| Bglll | 1541 |
| EcoRl | 1555 |
| Smal | 1573 |
| Smal | 2240 |
| Srfl | 2240 |
| Notl | 2244 |
| Dral | 3368 |
| Dral | 3387 |
| Dral | 4079 |

TABLE 13

RESTRICTION SITES FROM FIG. 6

| ENZYME | CUT SITE |
| --- | --- |
| BsaAl | 411 |
| Notl | 878 |
| Bglll | 1541 |
| BsaAl | 2185 |
| EcoRl | 3094 |
| EcoRl | 3126 |
| Smal | 3144 |
| Smal | 3811 |
| Srfl | 3811 |
| Notl | 3815 |
| Dral | 4939 |
| Dral | 4958 |
| Dral | 5650 |

TABLE 14

RESTRICTION SITES FROM FIG. 7

| ENZYME | CUT SITE |
| --- | --- |
| BsaAl | 411 |
| Notl | 878 |
| Bglll | 1541 |
| BsaAl | 2019 |
| Sbfl | 2150 |
| BsaAl | 2523 |
| Sbfl | 2789 |

TABLE 14-continued

RESTRICTION SITES FROM FIG. 7

| ENZYME | CUT SITE |
| --- | --- |
| EcoRl | 3083 |
| Smal | 3101 |
| Smal | 3768 |
| Srfl | 3768 |
| Notl | 3772 |
| Dral | 4896 |
| Dral | 4915 |
| Dral | 5607 |

TABLE 15

RESTRICTION SITES FROM FIG. 8

| ENZYME | CUT SITE |
| --- | --- |
| BsaAl | 411 |
| Notl | 878 |
| Bglll | 1541 |
| Sfil | 2259 |
| EcoRl | 2603 |
| EcoRl | 2635 |
| Smal | 2653 |
| Smal | 3320 |
| Srfl | 3320 |
| Notl | 3324 |
| Dral | 4448 |
| Dral | 4467 |
| Dral | 5159 |

TABLE 16

RESTRICTION SITES FROM FIG. 9

| ENZYME | CUT SITE |
| --- | --- |
| BsaAl | 411 |
| Notl | 878 |
| Bglll | 1541 |
| BsaAl | 3070 |
| EcoRl | 3131 |
| BsaAl | 3183 |
| Smal | 4029 |
| Srfl | 4029 |
| Notl | 4033 |
| Dral | 5157 |
| Dral | 5176 |
| Dral | 5868 |

TABLE 17

RESTRICTION SITES FROM FIG. 10

| ENZYME | CUT SITE | ENZYME | CUT SITE | ENZYME | CUT SITE |
| --- | --- | --- | --- | --- | --- |
| Notl | 693 | Bglll | 3814 | BspHl | 11793 |
| Hindlll | 704 | Hindlll | 3820 | Sphl | 12986 |
| EcoRV | 1241 | Hindlll | 3832 | Hindlll | 13143 |
| Bglll | 1356 | Sphl | 4136 | EcoRV | 13677 |
| Hindlll | 1362 | BspHl | 4138 | Bglll | 13792 |
| Hindlll | 1374 | Ncol | 5005 | Sphl | 13971 |
| Sphl | 1678 | EcoRl | 5356 | Sphl | 14061 |
| Sfil | 2118 | Smal | 5374 | Ncol | 14066 |
| Ncol | 2166 | BamHl | 5380 | EcoRV | 14277 |
| EcoRl | 2462 | Smal | 6041 | Ncol | 14321 |
| Smal | 2480 | Notl | 6045 | Bglll | 14648 |
| BamHl | 2486 | Xhol | 6054 | SexAl | 15269 |
| Smal | 3147 | Sphl | 6963 | Sfil | 15739 |
| Notl | 3151 | Ncol | 6990 | EcoRl | 15946 |

TABLE 17-continued

RESTRICTION SITES FROM FIG. 10

| ENZYME | CUT SITE | ENZYME | CUT SITE | ENZYME | CUT SITE |
|---|---|---|---|---|---|
| Hindlll | 3162 | Xhol | 7522 | BamHl | 15964 |
| EcoRV | 3699 | BspHl | 11293 | | |

TABLE 18

RESTRICTION SITES FROM FIG. 11

| ENZYME | CUT SITE | ENZYME | CUT SITE | ENZYME | CUT SITE |
|---|---|---|---|---|---|
| Notl | 693 | Bglll | 4293 | BspHl | 11324 |
| Hindlll | 704 | Sphl | 4472 | BspHl | 11824 |
| EcoRV | 1241 | Sphl | 4562 | Sphl | 13017 |
| Bglll | 1356 | Ncol | 4567 | Hindll | 13174 |
| Sphl | 1535 | Sfil | 5011 | EcoRV | 13708 |
| Sphl | 1625 | Ncol | 5059 | Bglll | 13823 |
| Ncol | 1630 | EcoRl | 5355 | Sphl | 14002 |
| Apal | 2508 | EcoRl | 5387 | Sphl | 14092 |
| EcoRl | 2909 | Smal | 5405 | Ncol | 14097 |
| EcoRl | 2941 | BamHl | 5411 | EcoRV | 14308 |
| Smal | 2959 | Smal | 6072 | Ncol | 14352 |
| BamHl | 2965 | Notl | 6076 | Bglll | 14679 |
| Smal | 3626 | Xhol | 6085 | SexAl | 15300 |
| Notl | 3630 | Sphl | 6994 | Sfil | 15770 |
| Hindlll | 3641 | Ncol | 7021 | EcoRl | 15977 |
| EcoRV | 4178 | Xhol | 7553 | BamHl | 15995 |

TABLE 19

RESTRICTION SITES FROM FIG. 12

| ENZYME | CUT SITE | ENZYME | CUT SITE | ENZYME | CUT SITE |
|---|---|---|---|---|---|
| Notl | 693 | EcoRl | 5312 | Dral | 11339 |
| Bglll | 1356 | EcoRl | 5344 | BsaAl | 12535 |
| BsaAl | 1834 | Smal | 5362 | Dral | 13017 |
| Sbfl | 1965 | Smal | 6029 | Dral | 13094 |
| BsaAl | 2338 | Srfl | 6029 | Bglll | 13780 |
| Sbfl | 2604 | Notl | 6033 | Rsrll | 14338 |
| EcoRl | 2898 | Xhol | 6042 | Bglll | 14636 |
| Smal | 2916 | BsaAl | 6850 | Ascl | 15191 |
| Smal | 3583 | Rsrll | 7062 | SexAl | 15257 |
| Srfl | 3583 | Xhol | 7510 | BsaAl | 15273 |
| Notl | 3587 | Dral | 8157 | Sfil | 15727 |
| Bglll | 4250 | BsaAl | 10315 | Sbfl | 15875 |
| Sfil | 4968 | Dral | 11320 | EcoRl | 15934 |

TABLE 20

RESTRICTION SITES FROM FIG. 13

| ENZYME | CUT SITE | ENZYME | CUT SITE | ENZYME | CUT SITE |
|---|---|---|---|---|---|
| Notl | 693 | Bglll | 4334 | BspHl | 11365 |
| Hindlll | 704 | Sphl | 4513 | BspHl | 11865 |
| EcoRV | 1241 | Sphl | 4603 | Sphl | 13058 |
| Bglll | 1356 | Ncol | 4608 | Hindlll | 13215 |
| Sphl | 1535 | Sfil | 5052 | EcoRV | 13749 |
| Sphl | 1625 | Ncol | 5100 | Bglll | 13864 |
| Ncol | 2497 | EcoRl | 5396 | Sphl | 14043 |
| Hindlll | 2938 | EcoRl | 5428 | Sphl | 14133 |
| EcoRV | 2946 | Smal | 5446 | Ncol | 14138 |
| EcoRl | 2950 | BamHl | 5452 | EcoRV | 14349 |
| EcoRl | 2982 | Smal | 6113 | Ncol | 14393 |
| Smal | 3000 | Notl | 6117 | Bglll | 14720 |
| BamHl | 3006 | Xhol | 6126 | SexAl | 15341 |
| Smal | 3667 | Sphl | 7035 | Sfil | 15811 |
| Notl | 3671 | Ncol | 7062 | EcoRl | 16018 |

TABLE 20-continued

RESTRICTION SITES FROM FIG. 13

| ENZYME | CUT SITE | ENZYME | CUT SITE | ENZYME | CUT SITE |
|---|---|---|---|---|---|
| Hindlll | 3682 | Xhol | 7594 | BamHl | 16036 |
| EcoRV | 4219 | | | | |

TABLE 21

RESTRICTION SITES FROM FIG. 14

| ENZYME | CUT SITE | ENZYME | CUT SITE | ENZYME | CUT SITE |
|---|---|---|---|---|---|
| Notl | 693 | Ncol | 5702 | Xhol | 9197 |
| Hindlll | 704 | EcoRl | 6053 | Sphl | 10106 |
| EcoRV | 1241 | Smal | 6071 | Ncol | 10133 |
| Bglll | 1356 | BamHl | 6077 | Xhol | 10665 |
| Sphl | 1535 | Smal | 6738 | BspHl | 14436 |
| Sphl | 1625 | Notl | 6742 | BspHl | 14936 |
| Ncol | 1630 | Hindlll | 6753 | Sphl | 16129 |
| EcoRl | 2946 | EcoRV | 7290 | Hindll | 16286 |
| SnaBl | 2998 | Bgll | 7405 | EcoRV | 16820 |
| Ncol | 3032 | Sphl | 7584 | Bglll | 16935 |
| EcoRV | 3179 | Sphl | 7674 | Sphl | 17114 |
| BamHl | 3183 | Ncol | 7679 | Sphl | 17204 |
| Smal | 3844 | Sfil | 8123 | Ncol | 17209 |
| Notl | 3848 | Ncol | 8171 | EcoRV | 17420 |
| Hindlll | 3859 | EcoRl | 8467 | Ncol | 17464 |
| EcoRV | 4396 | EcoRl | 8499 | Bglll | 17791 |
| Bglll | 4511 | Smal | 8517 | SexAl | 18412 |
| Hindlll | 4517 | BamHl | 8523 | Sfil | 18882 |
| Hindlll | 4529 | Smal | 9184 | EcoRl | 19089 |
| Sphl | 4833 | Notl | 9188 | BamHl | 19107 |
| BspHl | 4835 | | | | |

TABLE 22

RESTRICTION SITES FROM FIG. 15

| ENZYME | CUT SITE | ENZYME | CUT SITE | ENZYME | CUT SITE |
|---|---|---|---|---|---|
| Notl | 693 | Smal | 6999 | Smal | 11672 |
| Hindlll | 704 | Notl | 7003 | BamHl | 11678 |
| EcoRV | 1241 | Hindlll | 7014 | Smal | 12339 |
| Bglll | 1356 | EcoRV | 7551 | Notl | 12343 |
| Sphl | 1535 | Bglll | 7666 | Xhol | 12352 |
| Sphl | 1625 | Hindlll | 7672 | Sphl | 13261 |
| Ncol | 1630 | Hindlll | 7684 | Ncol | 13288 |
| EcoRl | 2946 | Sphl | 7988 | Xhol | 13820 |
| SnaBl | 2998 | BspHl | 7990 | BspHl | 17591 |
| Ncol | 3032 | Ncol | 8857 | BspHl | 18091 |
| EcoRV | 3179 | EcoRl | 9208 | Sphl | 19284 |
| BamHl | 3183 | Smal | 9226 | Hindlll | 19441 |
| Smal | 3844 | BamHl | 9232 | EcoRV | 19975 |
| Notl | 3848 | Smal | 9893 | Bglll | 20090 |
| Hindlll | 3859 | Notl | 9897 | Sphl | 20269 |
| EcoRV | 4396 | Hindlll | 9908 | Sphl | 20539 |
| Bglll | 4511 | EcoRV | 10445 | Ncol | 20364 |
| Sphl | 4690 | Bglll | 10560 | EcoRV | 20575 |
| Sphl | 4780 | Sphl | 10739 | Ncol | 20619 |
| Ncol | 4785 | Sphl | 10829 | Bglll | 20946 |
| EcoRl | 6101 | Ncol | 10834 | SexAl | 21567 |
| SnaBl | 6153 | Sfil | 11278 | Sfil | 22037 |
| Ncol | 6187 | Ncol | 11326 | EcoRl | 22244 |
| EcoRV | 6334 | EcoRl | 11622 | BamHl | 22262 |
| BamHl | 6338 | EcoRl | 11654 | | |

TABLE 23

RESTRICTION SITES FROM FIG. 16

| ENZYME | CUT SITE | ENZYME | CUT SITE | ENZYME | CUT SITE |
|---|---|---|---|---|---|
| Notl | 678 | Dral | 774 | BsaAl | 8144 |
| Spel | 685 | Swal | 774 | BsaAl | 8164 |
| BsaAl | 693 | Xhol | 779 | Dral | 8394 |
| SanDl | 698 | Dral | 1426 | Bglll | 8582 |
| Rsrll | 705 | BsaAl | 3546 | Rsrll | 9140 |
| SexAl | 711 | Dral | 4551 | Bglll | 9438 |
| Pacl | 722 | Dral | 4570 | Ascl | 9993 |
| Sgfl | 730 | BsaAl | 5766 | SexAl | 10059 |
| Sfil | 741 | Dral | 6248 | BsaAl | 10075 |
| Ascl | 748 | Dral | 6325 | Sfil | 10529 |
| Sbfl | 760 | Dral | 6424 | Sbfl | 10677 |
| Smal | 766 | Pacl | 7426 | EcoRl | 10736 |
| Srfl | 766 | Dral | 7887 | | |

TABLE 24

RESTRICTION SITES FROM FIG. 17

| ENZYME | CUT SITE | ENZYME | CUT SITE | ENZYME | CUT SITE |
|---|---|---|---|---|---|
| Notl | 678 | Smal | 766 | Dral | 6248 |
| Spel | 685 | Srfl | 766 | Dral | 6325 |
| BsaAl | 693 | Dral | 774 | Dral | 6424 |
| SanDl | 698 | Swal | 774 | Pacl | 7426 |
| Rsrll | 705 | Xhol | 779 | Dral | 7887 |
| SexAl | 711 | Dral | 1426 | BsaAl | 8144 |
| Pacl | 722 | BsaAl | 3546 | BsaAl | 8164 |
| Sgfl | 730 | Dral | 4551 | Dral | 8394 |
| Sfil | 741 | Dral | 4570 | Bglll | 8582 |
| Ascl | 748 | BsaAl | 5766 | EcoRl | 8606 |
| Sbfl | 760 | | | | |

TABLE 25

RESTRICTION SITES FROM FIG. 18

| ENZYME | CUT SITE | ENZYME | CUT SITE |
|---|---|---|---|
| BsaAl | 411 | EcoRl | 3123 |
| Notl | 878 | Smal | 3141 |
| Dral | 951 | Smal | 3808 |
| Pacl | 1953 | Srfl | 3808 |
| Dral | 2414 | Notl | 3812 |
| BsaAl | 2671 | Dral | 4936 |
| BsaAl | 2691 | Dral | 4955 |
| Dral | 2921 | Dral | 5647 |
| Bglll | 3109 | | |

TABLE 26

RESTRICTION SITES FROM FIG. 19

| ENZYME | CUT SITE | ENZYME | CUT SITE |
|---|---|---|---|
| BsaAl | 411 | BsaAl | 3753 |
| Notl | 878 | EcoRl | 4662 |
| Dral | 951 | Smal | 4680 |
| Pacl | 1953 | Smal | 5347 |
| Dral | 2414 | Srfl | 5347 |
| BsaAl | 2671 | Notl | 5351 |
| BsaAl | 2691 | Dral | 6475 |
| Dral | 2921 | Dral | 6494 |
| Bglll | 3109 | Dral | 7186 |

TABLE 27

RESTRICTION SITES FROM FIG. 20

| ENZYME | CUT SITE | ENZYME | CUT SITE |
|---|---|---|---|
| Notl | 878 | Hindlll | 4691 |
| Hindlll | 889 | EcoRV | 4699 |
| Sphl | 1041 | EcoRl | 4703 |
| Pacl | 1953 | Smal | 4721 |
| BspHl | 2613 | BamHl | 4727 |
| BspHl | 2736 | Smal | 5388 |
| Bglll | 3109 | Notl | 5392 |
| Sphl | 3288 | BspHl | 6477 |
| Sphl | 3378 | BspHl | 7485 |
| Ncol | 4250 | BspHl | 7590 |

TABLE 28

RESTRICTION SITES FROM FIG. 21

| ENZYME | CUT SITE | ENZYME | CUT SITE | ENZYME | CUT SITE |
|---|---|---|---|---|---|
| Xhol | 271 | Dral | 445 | SanDl | 4317 |
| Dral | 280 | Pacl | 1447 | Rsrll | 4324 |
| Swal | 280 | Dral | 1908 | SexAl | 4330 |
| Smal | 288 | BsaAl | 2165 | Pacl | 4341 |
| Srfl | 288 | BsaAl | 2185 | Sgfl | 4349 |
| Sbfl | 298 | Dral | 2415 | Sfil | 4361 |
| Ascl | 302 | Spel | 2609 | Ascl | 4368 |
| Sfil | 316 | Smal | 2867 | Sbfl | 4380 |
| Sgfl | 326 | Sfil | 3315 | Smal | 4386 |
| Pacl | 334 | EcoRl | 3608 | Srfl | 4386 |
| SexAl | 338 | Smal | 3626 | Dral | 4394 |
| Rsrll | 346 | Smal | 4293 | Swal | 4394 |
| SanDl | 353 | Srfl | 4293 | Dral | 5388 |
| BsaAl | 361 | Notl | 4297 | Dral | 5407 |
| Spel | 365 | Spel | 4304 | Dral | 6099 |
| Notl | 372 | BsaAl | 4312 | | |

TABLE 29

RESTRICTION SITES FROM FIG. 22

| ENZYME | CUT SITE | ENZYME | CUT SITE |
|---|---|---|---|
| BsaAl | 411 | BsaAl | 4638 |
| Notl | 878 | EcoRl | 4699 |
| Dral | 951 | BsaAl | 4751 |
| Pacl | 1953 | Smal | 5597 |
| Dral | 2414 | Srfl | 5597 |
| BsaAl | 2671 | Notl | 5601 |
| BsaAl | 2691 | Dral | 6725 |
| Dral | 2921 | Dral | 6744 |
| Bglll | 3109 | Dral | 7436 |

TABLE 30

RESTRICTION SITES FROM FIG. 23

| ENZYME | CUT SITE | ENZYME | CUT SITE | ENZYME | CUT SITE |
|---|---|---|---|---|---|
| Notl | 678 | Spel | 7388 | Notl | 11596 |
| Hindlll | 689 | EcoRV | 7413 | BspHl | 15339 |
| Sphl | 841 | Sphl | 7573 | BspHl | 15839 |
| Pacl | 1753 | Smal | 7646 | Sphl | 17032 |
| BspHl | 2413 | Sfil | 8094 | Hindlll | 17189 |
| BspHl | 2536 | Ncol | 8142 | Sphl | 17341 |
| Bglll | 2909 | EcoRl | 8387 | Pacl | 18253 |
| Sphl | 3088 | Smal | 8405 | BspHl | 18913 |
| Sphl | 3178 | BamHl | 8411 | BspHl | 19036 |
| Ncol | 3183 | BamHl | 9358 | Bglll | 19409 |
| Apal | 4061 | EcoRl | 9376 | Sphl | 19588 |
| EcoRl | 4462 | BspHl | 10162 | Sphl | 19678 |

TABLE 30-continued

RESTRICTION SITES FROM FIG. 23

| ENZYME | CUT SITE | ENZYME | CUT SITE | ENZYME | CUT SITE |
|---|---|---|---|---|---|
| SmaI | 4480 | NcoI | 10435 | NcoI | 19683 |
| BamHI | 4486 | BamHI | 10546 | EcoRV | 19894 |
| SmaI | 5147 | NcoI | 10558 | NcoI | 19938 |
| NotI | 5151 | SfiI | 10569 | BglII | 20265 |
| HindIII | 5162 | SphI | 10757 | SexAI | 20886 |
| SphI | 5314 | BglII | 10980 | SfiI | 21356 |
| PacI | 6226 | EcoRI | 11052 | EcoRI | 21563 |
| BspHI | 6886 | EcoRI | 11455 | BamHI | 21581 |
| BspHI | 7009 | HindIII | 11585 | | |

TABLE 31

RESTRICTION SITES FROM FIG. 24

| ENZYME | CUT SITE | ENZYME | CUT SITE | ENZYME | CUT SITE |
|---|---|---|---|---|---|
| NotI | 678 | BspHI | 7050 | HindIII | 11626 |
| HindIII | 689 | SpeI | 7429 | NotI | 11637 |
| SphI | 841 | EcoRV | 7454 | BspHI | 15380 |
| PacI | 1753 | SphI | 7614 | BspHI | 15880 |
| BspHI | 2413 | SmaI | 7687 | SphI | 17073 |
| BspHI | 2536 | SfiI | 8135 | HindIII | 17230 |
| BglII | 2909 | NcoI | 8183 | SphI | 17382 |
| SphI | 3088 | EcoRI | 8428 | PacI | 18294 |
| SphI | 3178 | SmaI | 8446 | BspHI | 18954 |
| NcoI | 4050 | BamHI | 8452 | BspHI | 19077 |
| HindIII | 4491 | BamHI | 9399 | BglII | 19450 |
| EcoRV | 4499 | EcoRI | 9417 | SphI | 19629 |
| EcoRI | 4503 | BspHI | 10203 | SphI | 19719 |
| SmaI | 4521 | NcoI | 10476 | NcoI | 19724 |
| BamHI | 4527 | BamHI | 10587 | EcoRV | 19935 |
| SmaI | 5188 | NcoI | 10599 | NcoI | 19979 |
| NotI | 5192 | SfiI | 10610 | BglII | 20306 |
| HindIII | 5203 | SphI | 10798 | SexAI | 20927 |
| SphI | 5355 | BglII | 11021 | SfiI | 21397 |
| PacI | 6267 | EcoRI | 11093 | EcoRI | 21604 |
| BspHI | 6927 | EcoRI | 11496 | BamHI | 21622 |

TABLE 32

RESTRICTION SITES FROM FIG. 25

| ENZYME | CUT SITE | ENZYME | CUT SITE | ENZYME | CUT SITE |
|---|---|---|---|---|---|
| NotI | 678 | EcoRI | 9013 | SphI | 15521 |
| HindIII | 689 | EcoRV | 9246 | BglII | 15744 |
| SphI | 841 | BamHI | 9250 | EcoRI | 15816 |
| PacI | 1753 | SmaI | 9911 | EcoRI | 16219 |
| BspHI | 2413 | NotI | 9915 | HindIII | 16349 |
| BspHI | 2536 | HindIII | 9926 | NotI | 16360 |
| BglII | 2909 | SphI | 10078 | BspHI | 20103 |
| SphI | 3088 | PacI | 10990 | BspHI | 20603 |
| SphI | 3178 | BspHI | 11650 | SphI | 21796 |
| NcoI | 4050 | BspHI | 11773 | HindIII | 21953 |
| HindIII | 4491 | SpeI | 12152 | SphI | 22105 |
| EcoRV | 4499 | EcoRV | 12177 | PacI | 23017 |
| EcoRI | 4503 | SphI | 12337 | BspHI | 23677 |
| SmaI | 4521 | SmaI | 12410 | BspHI | 23800 |
| BamHI | 4527 | SfiI | 12858 | BglII | 24173 |
| SmaI | 5188 | NcoI | 12906 | SphI | 24352 |
| NotI | 5192 | EcoRI | 13151 | SphI | 24442 |
| HindIII | 5203 | SmaI | 13169 | NcoI | 24447 |
| SphI | 5355 | BamHI | 13175 | EcoRV | 24658 |
| PacI | 6267 | BamHI | 14122 | NcoI | 24702 |
| BspHI | 6927 | EcoRI | 14140 | BglII | 25029 |
| BspHI | 7050 | BspHI | 14926 | SexAI | 25650 |
| BglII | 7423 | NcoI | 15199 | SfiI | 26120 |
| SphI | 7602 | BamHI | 15310 | EcoRI | 26327 |

TABLE 32-continued

RESTRICTION SITES FROM FIG. 25

| ENZYME | CUT SITE | ENZYME | CUT SITE | ENZYME | CUT SITE |
|---|---|---|---|---|---|
| SphI | 7692 | NcoI | 15322 | BamHI | 26345 |
| NcoI | 7697 | SfiI | 15333 | | |

TABLE 33

RESTRICTION SITES FROM FIG. 26

| ENZYME | CUT SITE | ENZYME | CUT SITE | ENZYME | CUT SITE |
|---|---|---|---|---|---|
| BglII | 649 | EcoRI | 6440 | DraI | 8098 |
| DraI | 1202 | SmaI | 6712 | BsaAI | 8190 |
| DraI | 1278 | NotI | 6717 | BsaAI | 8731 |
| BsaAI | 1370 | SpeI | 6724 | RsrII | 8943 |
| SfiI | 2185 | BsaAI | 6732 | EcoRI | 9280 |
| EcoRI | 2529 | SanDI | 6737 | DraI | 10201 |
| SmaI | 2801 | RsrII | 6744 | BsaAI | 12321 |
| NotI | 2806 | SexAI | 6750 | DraI | 13326 |
| BglII | 3468 | PacI | 6761 | DraI | 13345 |
| DraI | 4021 | SgfI | 6769 | BsaAI | 14541 |
| DraI | 4097 | SfiI | 6780 | DraI | 15023 |
| BsaAI | 4189 | AscI | 6787 | DraI | 15100 |
| RsrII | 4844 | SbfI | 6799 | BglII | 15786 |
| BglII | 5142 | SmaI | 6805 | DraI | 16339 |
| AscI | 5697 | SrfI | 6805 | DraI | 16415 |
| SexAI | 5763 | DraI | 6813 | BsaAI | 16507 |
| BsaAI | 5779 | SwaI | 6813 | BsaAI | 17248 |
| SfiI | 6233 | BglII | 7469 | EcoRI | 18157 |
| SbfI | 6381 | DraI | 8022 | | |

TABLE 34

RESTRICTION SITES FROM FIG. 27

| ENZYME | CUT SITE | ENZYME | CUT SITE |
|---|---|---|---|
| EcoRV | 637 | EcoRV | 15257 |
| BglII | 752 | NotI | 15268 |
| EcoRV | 2829 | BglII | 16310 |
| HindIII | 8420 | EcoRV | 17613 |
| BglII | 9445 | BglII | 17984 |
| EcoRV | 12082 | EcoRV | 19548 |
| HindIII | 12086 | NotI | 19559 |
| BglIII | 13111 | | |

TABLE 35

RESTRICTION SITES FROM FIG. 28

| ENZYME | CUT SITE | ENZYME | CUT SITE |
|---|---|---|---|
| EcoRV | 637 | EcoRV | 14937 |
| EcoRV | 2829 | NotI | 14948 |
| HindIII | 8420 | EcoRV | 17133 |
| EcoRV | 11922 | EcoRV | 19068 |
| HindIII | 11926 | NotI | 19079 |

TABLE 36

RESTRICTION SITES FROM FIG. 29

| ENZYME | CUT SITE | ENZYME | CUT SITE | ENZYME | CUT SITE |
|---|---|---|---|---|---|
| NotI | 678 | AscI | 748 | BsaAI | 3546 |
| SpeI | 685 | SbfI | 760 | DraI | 4551 |
| BsaAI | 693 | SmaI | 766 | DraI | 4570 |
| SanDI | 698 | SrfI | 766 | BsaAI | 5766 |

TABLE 36-continued

RESTRICTION SITES FROM FIG. 29

| ENZYME | CUT SITE | ENZYME | CUT SITE | ENZYME | CUT SITE |
|---|---|---|---|---|---|
| RsrII | 705 | DraI | 774 | DraI | 6248 |
| SexAI | 711 | SwaI | 774 | DraI | 6325 |
| PacI | 722 | XhoI | 779 | BglII | 7011 |
| SgfI | 730 | DraI | 1426 | EcoRI | 7035 |
| SfiI | 741 | | | | |

TABLE 37

RESTRICTION SITES FROM FIG. 30

| ENZYME | CUT SITE | ENZYME | CUT SITE | ENZYME | CUT SITE |
|---|---|---|---|---|---|
| XhoI | 271 | BsaAI | 361 | SexAI | 1771 |
| DraI | 280 | SpeI | 365 | PacI | 1782 |
| SwaI | 280 | NotI | 372 | SgfI | 1790 |
| SmaI | 288 | SmaI | 380 | SfiI | 1802 |
| SrfI | 288 | SrfI | 380 | AscI | 1809 |
| SbfI | 298 | SmaI | 1047 | SbfI | 1821 |
| AscI | 302 | EcoRI | 1061 | SmaI | 1827 |
| SfiI | 316 | BglII | 1075 | SrfI | 1827 |
| SgfI | 326 | NotI | 1738 | DraI | 1835 |
| PacI | 334 | SpeI | 1745 | SwaI | 1835 |
| SexAI | 338 | BsaAI | 1753 | DraI | 2829 |
| RsrII | 346 | SanDI | 1758 | DraI | 2848 |
| SanDI | 353 | RsrII | 1765 | DraI | 3540 |

What is claimed is:

1. A recombinant vector comprising operatively linked in the 5' to 3' direction:
   a promoter functional in plants that directs transcription of a first nucleic acid sequence, a second nucleic acid sequence, and a third nucleic acid sequence;
   a nucleic acid sequence;
   a second nucleic acid sequence;
   a third nucleic acid sequence;
   a 3' transcription terminator; and
   a 3' polyadenylation signal sequence;
   wherein:
      the first nucleic acid sequence, second nucleic acid sequence, and third nucleic acid sequence encode different proteins; and
      the first nucleic acid sequence, second nucleic acid sequence, and third nucleic acid sequence are independently selected from the group consisting of a nucleic acid sequence encoding a polyhydroxyalkanoate synthase protein, a nucleic acid sequence encoding a β-ketoacyl reductase protein, and a nucleic acid sequence encoding a β-ketothiolase protein.

2. The recombinant vector of claim 1, wherein the promoter is a viral promoter.

3. The recombinant vector of claim 1, wherein the promoter is a CaMV 35S promoter, an enhanced CaMV 35S promoter, or an FMV 35S promoter.

4. The recombinant vector of claim 1, wherein the promoter is an enhanced CaMV 35S promoter.

5. The recombinant vector of claim 1, wherein the promoter is a tissue specific promoter.

6. The recombinant vector of claim 1, wherein the promoter is a Lesquerella hydroxylase promoter or a 7S conglycinin promoter.

7. The recombinant vector of claim 1, wherein the promoter is a Lesquerella hydroxylase promoter.

8. The recombinant vector of claim 1, wherein:
   the first nucleic acid sequence further encodes a chloroplast transit peptide;
   the second nucleic acid sequence further encodes a chloroplast transit peptide; and
   the third nucleic acid sequence further encodes a chloroplast transit peptide.

9. A recombinant vector comprising:
   a first element comprising operatively linked in the 5' to 3' direction:
      a first promoter that directs transcription in plants of a first nucleic acid sequence;
      a first nucleic acid sequence encoding a polyhydroxyalkanoate synthase protein;
      a first 3' transcription terminator; and
      a first 3' polyadenylation signal sequence;
   a second element comprising operatively linked in the 5' to 3' direction:
      a second promoter that directs transcription in plants of a second nucleic acid sequence;
      a second nucleic acid sequence encoding a β-ketoacyl reductase protein;
      a second 3' transcription terminator; and
      a second 3' polyadenylation signal sequence; and
   a third element comprising operatively linked in the 5' to 3' direction:
      a third promoter that directs transcription in plants of a third nucleic acid sequence;
      a third nucleic acid sequence encoding a β-ketothiolase protein;
      a third 3' transcription terminator; and
      a third 3' polyadenylation signal sequence.

10. The recombinant vector of claim 9, wherein the β-ketothiolase protein:
    catalyzes the condensation of two molecules of acetyl-CoA to produce acetoacetyl-CoA; and
    catalyzes the condensation of acetyl-CoA and propionyl-CoA to produce β-ketovaleryl-CoA.

11. The recombinant vector of claim 9, wherein the β-ketoacyl reductase protein:
    catalyzes the reduction of acetoacetyl-CoA to β-hydroxybutyryl-CoA; and
    catalyzes the reduction of β-ketovaleryl-CoA to β-hydroxyvaleryl-CoA.

12. The recombinant vector of claim 9, wherein the polyhydroxyalkanoate synthase protein is selected from the group consisting of:
    a polyhydroxyalkanoate synthase protein that catalyzes the incorporation of β-hydroxybutyryl-CoA into P(3HB) polymer; and
    a polyhydroxyalkanoate synthase protein that catalyzes the incorporation of β-hydroxybutyryl-CoA and β-hydroxyvaleryl-CoA into P(3HB-co-3HV) copolymer.

13. The recombinant vector of claim 9, wherein:
    the β-ketothiolase protein comprises a transit peptide sequence that directs transport of the β-ketothiolase protein to the plastid;
    the β-ketoacyl reductase protein comprises a transit peptide sequence that directs transport of the β-ketoacyl reductase protein to the plastid; and
    the polyhydroxyalkanoate synthase protein comprises a transit peptide sequence that directs transport of the polyhydroxyalkanoate synthase protein to the plastid.

14. The recombinant vector of claim 9, further comprising a nucleic acid sequence encoding a threonine deaminase protein.

15. The recombinant vector of claim 9, further comprising a nucleic acid sequence encoding a deregulated threonine deaminase protein.

16. The recombinant vector of claim 9, wherein:
the first promoter directs transcription of the first nucleic acid sequence in plants;
the second promoter directs transcription of the second nucleic acid sequence in plants; and
the third promoter directs transcription of the third nucleic acid sequence in plants.

17. The recombinant vector of claim 9, wherein the first promoter, second promoter, and third promoter are viral promoters.

18. The recombinant vector of claim 9, wherein:
the first promoter is a CaMV 35S promoter, an enhanced CaMV 35S promoter, or an FMV 35S promoter;
the second promoter is a CaMV 35S promoter, an enhanced CaMV 35S promoter, or an FMV 35S promoter; and
the third promoter is a CaMV 35S promoter, an enhanced CaMV 35S promoter, or an FMV 35S promoter.

19. The recombinant vector of claim 9, wherein:
the first promoter is an enhanced CaMV 35S promoter;
the second promoter is an enhanced CaMV 35S promoter; and
the third promoter is an enhanced CaMV 35S promoter.

20. The recombinant vector of claim 9, wherein:
the first promoter is a tissue specific promoter;
the second promoter is a tissue specific promoter; and
the third promoter is a tissue specific promoter.

21. The recombinant vector of claim 9, wherein:
the first promoter is a Lesquerella hydroxylase promoter or a 7S conglycinin promoter;
the second promoter is a Lesquerella hydroxylase promoter or a 7S conglycinin promoter; and
the third promoter is a Lesquerella hydroxylase promoter or a 7S conglycinin promoter.

22. The recombinant vector of claim 9, wherein:
the first promoter is a Lesquerella hydroxylase promoter;
the second promoter is a Lesquerella hydroxylase promoter; and
the third promoter is a Lesquerella hydroxylase promoter.

23. The recombinant vector of claim 9, wherein:
the first nucleic acid sequence further encodes a chloroplast transit peptide;
the second nucleic acid sequence further encodes a chloroplast transit peptide; and
the third nucleic acid sequence further encodes a chloroplast transit peptide.

24. A transformed host plant cell comprising a recombinant vector, wherein the recombinant vector comprises:
a first element comprising operatively linked in the 5' to 3' direction:
a first promoter that directs transcription of a first nucleic acid sequence;
a first nucleic acid sequence encoding a polyhydroxyalkanoate synthase protein;
a first 3' transcription terminator; and
a first 3' polyadenylation signal sequence;
a second element comprising operatively linked in the 5' to 3' direction:
a second promoter that directs transcription of a second nucleic acid sequence;
a second nucleic acid sequence encoding a β-ketoacyl reductase protein;
a second 3' transcription terminator; and
a second 3' polyadenylation signal sequence; and
a third element comprising operatively linked in the 5' to 3' direction:
a third promoter that directs transcription of a third nucleic acid sequence;
a third nucleic acid sequence encoding a β-ketothiolase protein;
a third 3' transcription terminator; and
a third 3' polyadenylation signal sequence.

25. The transformed host plant cell of claim 24, wherein:
the first nucleic acid sequence further encodes a chloroplast transit peptide;
the second nucleic acid sequence farther encodes a chloroplast transit peptide; and
the third nucleic acid sequence further encodes a chloroplast transit peptide.

26. A transformed host plant cell comprising:
a first element comprising operatively linked in the 5' to 3' direction:
a first promoter that directs transcription of a first nucleic acid sequence;
a first nucleic acid sequence encoding a polyhydroxyalkanoate synthase protein;
a first 3' transcription terminator; and
a first 3' polyadenylation signal sequence;
a second element comprising operatively linked in the 5' to 3' direction:
a second promoter that directs transcription of a second nucleic acid sequence;
a second nucleic acid sequence encoding a β-ketoacyl reductase protein;
a second 3' transcription terminator; and
a second 3' polyadenylation signal sequence; and
a third element comprising operatively linked in the 5' to 3' direction:
a third promoter that directs transcription of a third nucleic acid sequence;
a third nucleic acid sequence encoding a β-ketothiolase protein;
a third 3' transcription terminator; and
a third 3' polyadenylation signal sequence;
wherein the first element, second element, and third element are cointegrated between a single left Ti border sequence and a single right Ti border sequence.

27. The transformed host plant cell of claim 26, wherein the transformed host plant cell is a tobacco, wheat, potato, Arabidopsis, corn, soybean, canola, oil seed rape, sunflower, flax, peanut, sugarcane, switchgrass, or alfalfa cell.

28. The transformed host plant cell of claim 26, wherein:
the first nucleic acid sequence further encodes a chloroplast transit peptide;
the second nucleic acid sequence further encodes a chloroplast transit peptide; and
the third nucleic acid sequence further encodes a chloroplast transit peptide.

29. A transformed plant comprising:
a first element comprising operatively linked in the 5' to 3' direction:
a first promoter that directs transcription of a first nucleic acid sequence;

a first nucleic acid sequence encoding a polyhydroxyalkanoate synthase protein;
a first 3' transcription terminator; and
a first 3' polyadenylation signal sequence;
a second element comprising operatively linked in the 5' to 3' direction:
  a second promoter that directs transcription of a second nucleic acid sequence;
  a second nucleic acid sequence encoding a β-ketoacyl reductase protein;
  a second 3' transcription terminator; and
  a second 3' polyadenylation signal sequence; and
a third element comprising operatively linked in the 5' to 3' direction:
  a third promoter that directs transcription of a third nucleic acid sequence;
  a third nucleic acid sequence encoding a β-ketothiolase protein;
  a third 3' transcription terminator; and
  a third 3' polyadenylation signal sequence;
wherein the first element, second element, and third element are cointegrated between a single left Ti border sequence and a single right Ti border sequence.

30. The transformed plant of claim 29, wherein the transformed plant is a tobacco, wheat, potato, Arabidopsis, corn, soybean, canola, oil seed rape, sunflower, flax, peanut, sugarcane, switchgrass, or alfalfa plant.

31. The transformed plant of claim 29, wherein:
the first nucleic acid sequence further encodes a chloroplast transit peptide;
the second nucleic acid sequence further encodes a chloroplast transit peptide; and
the third nucleic acid sequence further encodes a chloroplast transit peptide.

32. A method of preparing transformed host plant cells, the method comprising:
selecting a host plant cell;
transforming the selected host plant cell with a recombinant vector comprising:
  a first element comprising operatively linked in the 5' to 3' direction:
    a first promoter that directs transcription of the first nucleic acid sequence;
    a first nucleic acid sequence encoding a polyhydroxyalkanoate synthase protein;
    a first 3' transcription terminator; and
    a first 3' polyadenylation signal sequence;
  a second element comprising operatively linked in the 5' to 3' direction:
    a second promoter that directs transcription of the second nucleic acid sequence;
    a second nucleic acid sequence encoding a β-ketoacyl reductase protein;
    a second 3' transcription terminator; and
    a second 3' polyadenylation signal sequence; and
  a third element comprising operatively linked in the 5' to 3' direction:
    a third promoter that directs transcription of the third nucleic acid sequence;
    a third, nucleic acid sequence encoding a β-ketothiolase protein;
    a third 3' transcription terminator; and
    a third: 3' polyadenylation signal sequence; and
obtaining transformed host plant cells; wherein the transformed host plant cells produce polyhydroxyalkanoate polymer.

33. A method of preparing transformed host plant cells, the method comprising:
selecting a host plant cell;
transforming the selected host plant cell with a recombinant vector comprising operatively linked in the 5' to 3' direction:
  a promoter that directs transcription of a first nucleic acid sequence, second nucleic acid sequence, and third nucleic acid sequence;
  a first nucleic acid sequence;
  a second nucleic acid sequence;
  a third nucleic acid sequence;
  a 3' transcription terminator; and
  a 3' polyadenylation signal sequence; and
obtaining transformed host plant cells; wherein:
  the first nucleic acid sequence, second nucleic acid sequence, and third nucleic acid sequence encode different proteins;
  the first nucleic acid sequence, second nucleic acid sequence, and third nucleic acid sequence are independently selected from the group consisting of a nucleic acid sequence encoding a polyhydroxyalkanoate synthase protein, a nucleic acid sequence encoding a β-ketoacyl reductase protein, and a nucleic acid sequence encoding a β-ketothiolase protein; and
  the transformed host plant cells produce polyhydroxyalkanoate polymer.

34. A method of preparing transformed plants, the method comprising:
selecting a host plant cell;
transforming the selected host plant cell with a recombinant vector comprising:
  a first element comprising operatively linked in the 5' to 3' direction:
    a first promoter that directs transcription of a first nucleic acid sequence;
    a first nucleic acid sequence encoding a polyhydroxyalkanoate synthase protein;
    a first 3' transcription terminator; and
    a first 3' polyadenylation signal sequence;
  a second element comprising operatively linked in the 5' to 3' direction:
    a second promoter that directs transcription of a second nucleic acid sequence;
    a second nucleic acid sequence encoding a β-ketoacyl reductase protein;
    a second 3' transcription terminator; and
    a second 3' polyadenylation signal sequence; and
  a third element comprising operatively linked in the 5' to 3' direction:
    a third promoter that directs transcription of a third nucleic acid sequence;
    a third nucleic acid sequence encoding a β-ketothiolase protein;
    a third 3' transcription terminator; and
    a third 3' polyadenylation signal sequence;
obtaining transformed host plant cells; and
regenerating the transformed host plant cells to produce transformed plants, wherein the transformed plants produce polyhydroxyalkanoate polymer.

35. A method of preparing transformed plants, the method comprising:
selecting a host plant cell;
transforming the selected host plant cell with a recombinant vector comprising operatively linked in the 5' to 3' direction:
  a promoter that directs transcription of a first nucleic acid sequence, second nucleic acid sequence, and third nucleic acid sequence;
  a first nucleic acid sequence;
  a second nucleic acid sequence;
  a third nucleic acid sequence;
  a 3' transcription terminator; and
  a 3' polyadenylation signal sequence;
obtaining transformed host plant cells; and
regenerating the transformed host plant cells to produce transformed plants;
wherein:
  the first nucleic acid sequence, second nucleic acid sequence, and third nucleic acid sequence encode different proteins;
  the first nucleic acid sequence, second nucleic acid sequence, and third nucleic acid sequence are independently selected from the group consisting of a nucleic acid sequence encoding a polyhydroxyalkanoate synthase protein, a nucleic acid sequence encoding a β-ketoacyl reductase protein, and a nucleic acid sequence encoding a β-ketothiolase protein; and
  the transformed plants produce polyhydroxyalkanoate polymer.

36. A method of producing polyhydroxyalkanoate comprising:
  obtaining the transformed host cell of claim 24 or claim 26;
  culturing the transformed host cell under conditions suitable for the production of polyhydroxyalkanoate; and
  recovering polyhydroxyalkanoate from the transformed host cell.

37. The method of claim 36, wherein the polyhydroxyalkanoate is poly(3-hydroxybutyrate), poly(4-hydroxybutyrate), or poly(3-hydroxybutyrate-co-4-hydroxybutyrate).

38. A method of producing polyhydroxyalkanoate comprising:
  obtaining the transformed plant of claim 29;
  growing the transformed plant under conditions suitable for the production of polyhydroxyalkanoate; and
  recovering polyhydroxyalkanoate from the transformed plant.

39. The method of claim 38, wherein the polyhydroxyalkanoate is poly(3-hydroxybutyrate), poly(3-hydroxyvalerate), or poly(3-hydroxybutyrate-co-3-hydroxyvalerate).

* * * * *

UNITED STATES PATENT AND TRADEMARK OFFICE
CERTIFICATE OF CORRECTION

PATENT NO. : 6,448,473 B1
DATED : September 10, 2002
INVENTOR(S) : Timothy A. Mitsky, Steven C. Slater, Steven E. Reiser, Ming Hao and Kathryn L. Houmiel It is certified that error appears in the above-identified patent and that said Letters Patent is hereby corrected as shown below:

<u>Column 49,</u>
Line 34, cancel "nuclcic" and insert -- nucleic --.
Line 36, cancel "nucleic:" and insert -- first nucleic --.

<u>Column 52,</u>
Line 18, cancel "farther" and insert -- further --.

Signed and Sealed this

Twenty-fourth Day of December, 2002

JAMES E. ROGAN
*Director of the United States Patent and Trademark Office*